(12) United States Patent
Steiner et al.

(10) Patent No.: US 8,178,547 B2
(45) Date of Patent: May 15, 2012

(54) HETEROCYCLIC ANTIVIRAL COMPOUNDS

(75) Inventors: Sandra Steiner, Little Falls, NJ (US); Jim Li, San Francisco, CA (US); Ryan Craig Schoenfeld, San Jose, CA (US); Francisco Xavier Talamas, Mountain View, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 254 days.

(21) Appl. No.: 12/636,999

(22) Filed: Dec. 14, 2009

(65) Prior Publication Data

US 2010/0158860 A1 Jun. 24, 2010

Related U.S. Application Data

(60) Provisional application No. 61/139,982, filed on Dec. 22, 2008, provisional application No. 61/156,442, filed on Feb. 27, 2009.

(51) Int. Cl.
*A01N 43/54* (2006.01)
(52) U.S. Cl. ........................ 514/269; 544/319
(58) Field of Classification Search .................... 544/319
See application file for complete search history.

(56) References Cited

U.S. PATENT DOCUMENTS

| | | | | |
|---|---|---|---|---|
| 4,783,466 A * | 11/1988 | Katoh et al. | ............... | 514/256 |
| 6,048,823 A | 4/2000 | Yamaguchi et al. | | |
| 8,063,072 B2 * | 11/2011 | Li et al. | ............... | 514/332 |
| 2010/0272677 A1 * | 10/2010 | Lee et al. | ............... | 424/85.2 |
| 2010/0330032 A1 * | 12/2010 | Chin et al. | ............... | 424/85.2 |
| 2011/0123490 A1 * | 5/2011 | Schoenfeld et al. | ......... | 424/85.2 |

FOREIGN PATENT DOCUMENTS

| | | |
|---|---|---|
| JP | 11140054 A1 | 5/1999 |
| WO | WO00/09543 A2 | 2/2000 |
| WO | WO01/85172 A1 | 11/2001 |
| WO | 2008082484 A1 | 7/2008 |
| WO | 2008082488 A1 | 7/2008 |
| WO | 2008104473 A2 | 9/2008 |
| WO | WO2009/039135 A1 | 3/2009 |
| WO | WO2010/111436 A2 | 9/2010 |
| WO | WO2010/111437 A1 | 9/2010 |

* cited by examiner

*Primary Examiner* — James O Wilson
*Assistant Examiner* — Alexander R Pagano
(74) *Attorney, Agent, or Firm* — Brian L. Buckwalter

(57) ABSTRACT

Compounds having the formula I wherein A, $R^1$, $R^2$, $R^3$, $R^{4a}$, $R^{4b}$, $R^{4c}$, $R^5$, $R^6$, $R^{7a}$, $R^{7b}$, $Ar^1$, $R^c$, $R^d$, $R^e$, $R^f$, X, n and p are as defined herein are Hepatitis C virus NS5b polymerase inhibitors. Also disclosed are compositions and methods for treating an HCV infection and inhibiting HCV replication.

I

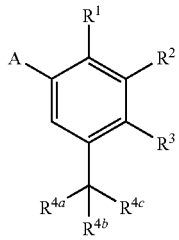

7 Claims, No Drawings

HETEROCYCLIC ANTIVIRAL COMPOUNDS

CROSS-REFERENCE TO PRIOR APPLICATIONS

This application claims the benefit of priority to U.S. Ser. No. 61/139,982 filed Dec. 22, 2008 and U.S. Ser. No. 61/156,442 filed Feb. 27, 2009 both of which are hereby incorporated by reference in their entirety

FIELD OF THE INVENTION

The present invention provides non-nucleoside compounds of formula I, and certain derivatives thereof, which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., Flaviviridae: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forms and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.*, 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.*, 1999 19:5; Di Besceglie, A. M. and Bacon, B. R., *Scientific American*, October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investig. Drugs* 2003 12(8): 1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.—Infect. Dis.* 2003 3(3):207-219.

Ribavirin (1-((2R,3R,4S,5R)-3,4-Dihydroxy-5-hydroxymethyl-tetrahydro-furan-2-yl)-1H[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release* 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase.

The RNA-dependent RNA polymerase is absolutely essential for replication of the single-stranded, positive sense, RNA genome. This enzyme has elicited significant interest among medicinal chemists.

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons.

Combination therapy with of ribavirin and interferon is the current standard of care for HCV therapy. Compounds of the present invention may be administered as an additional combination therapy with interferon and ribavirin. Viramidine is a newly introduce prodrug of ribavirin which also may prove valuable.

Other interferons currently in development include albinterferon-α-2b (Albuferon), IFN-omega with DUROS, LOCTERON™ and interferon-α-2b XL. As these and other interferons reach the marketplace their use in combination therapy with compounds of the present invention is anticipated.

HCV polymerase inhibitors are another target for drug discovery and compounds in development include R-1626, R-7128, IDX184/IDX102, PF-868554 (Pfizer), VCH-759 (ViroChem), GS-9190 (Gilead), A-837093 and A-848837 (Abbot), MK-3281 (Merck), GSK949614 and GSK625433 (Glaxo), ANA598 (Anadys), VBY 708 (ViroBay).

Inhibitors of the HCV NS3 protease also have been identified as potentially useful for treatment of HCV. Protease inhibitors in clinical trials include VX-950 (Telaprevir, Vertex), SCH503034 (Broceprevir, Schering), TMC435350 (Tibotec/Medivir) and ITMN-191 (Intermune/Roche). Other protease inhibitors in earlier stages of development include MK7009 (Merck), BMS-790052 (Bristol Myers Squibb), VBY-376 (Virobay), IDXSCA/IDXSCB (Idenix), BI12202 (Boehringer), VX-500 (Vertex), PHX1766 Phenomix).

Other targets for anti-HCV therapy under investigation include cyclophilin inhibitors which inhibit RNA binding to NS5b, nitazoxanide, Celgosivir (Migenix), an inhibitor of α-glucosidase-1, caspase inhibitors, Toll-like receptor agonists and immunostimulants such as Zadaxin (SciClone).

SUMMARY OF THE INVENTION

There is currently no preventive treatment of Hepatitis C virus (HCV) and currently approved therapies, which exist only against HCV, are limited. Design and development of new pharmaceutical compounds is essential.

The present invention provides a compound according to formula I, or a pharmaceutically acceptable salt thereof, wherein:

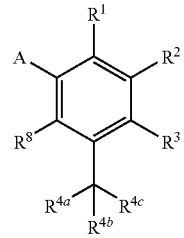

A is a heteroaryl radical selected from the group consisting of 3-oxo-3,4-dihydro-pyrazin-2-yl, 3-oxo-2,3-dihydro-pyridazin-4-yl, 6-oxo-1,6-dihydro-pyrimidin-5-yl, 6-oxo-1,6-dihydro-[1,2,4]triazin-5-yl, 2,4-dioxo-1,2,3,4-tetrahydro-pyrimidin-5-yl and 4,6-dioxo-1,4,5,6-tetrahydro-pyrimidin-5-yl said heteroaryl being optionally substituted by halogen, $C_{1-6}$ alkyl, $C_{1-3}$ haloalkyl, $C_{1-3}$ dialkylamino or $C_{1-6}$ alkoxy.

$R^1$ is hydrogen, hydroxy, $C_{1-3}$ hydroxyalkyl, COX or cyano.

$R^2$ is (a) —[$C(R^6)_2$]$_p$—$Ar^1$, (b) $CR^{7a}$=$CR^{7b}Ar^1$, (c) naphthyl optionally substituted by one to three groups independently selected from the group consisting of $C_{1-6}$ alkoxy, $C_{1-6}$ alkyl, $C_{1-6}$ hydroxyalkyl, halogen, $(CH_2)_nNR^cR^d$, cyano, $C_{1-6}$ alkoxycarbonyl, and carboxyl (d) —$NR^5COAr^1$ or (e) $CONR^5Ar^1$.

$R^3$ alone is hydrogen, $C_{1-6}$ alkyl, $C_{1-6}$ haloalkyl, $C_{1-6}$ alkoxy, $C_{1-6}$ haloalkoxy, or halogen or $R^3$ and $R^{4a}$ together are $CH_2$—O and together with atoms to which they are attached form a 2,3-dihydrobenzofuran.

$R^{4a}$, $R^{4b}$ and $R^{4c}$ (i) when taken independently are selected independently from $C_{1-3}$ alkyl, $C_{1-2}$ alkoxy, $C_{1-2}$ fluoroalkyl, hydroxy or halogen or (ii) when taken together, $R^{4a}$ and $R^{4b}$ together are $C_{2-4}$ methylene and $R^{4c}$ is $C_{1-3}$ alkyl, $C_{1-2}$ alkoxy, $C_{1-2}$ fluoroalkyl or halogen, or (iii) either $R^8$ or $R^3$ and $R^{4a}$ together are $CH_2$—O and together with atoms to which they are attached for a 2,3-dihydro-benzofuran and $R^{4b}$ and $R^{4c}$ are $C_{1-3}$ alkyl, or (iv) $R^{4a}$ and $R^{4b}$ together are ethylene and $R^{4c}$ is hydrogen, or (v) $R^{4a}$, $R^{4b}$ and $R^{4c}$ together with the carbon to which they are attached are $C_{1-6}$ fluoroalkyl.

$R^8$ alone is hydrogen, fluorine, or $R^8$ and $R^{4a}$ together are $CH_2$—O and together with atoms to which they are attached form a 2,3-dihydrobenzofuran.

$R^5$ is hydrogen or $C_{1-6}$ alkyl.

$R^6$ is independently in each occurrence hydrogen, $C_{1-6}$ alkyl, carboxy, $C_{1-6}$ alkoxycarbonyl or $C_{1-6}$ hydroxyalkyl.

$R^{7a}$ and $R^{7b}$ are independently hydrogen or $C_{1-6}$ alkyl.

$Ar^1$ is phenyl or pyridinyl optionally independently substituted with one to three substituents selected from the group consisting of hydroxy, $C_{1-6}$ alkoxy, $C_{1-6}$ alkyl, $C_{1-6}$ hydroxyalkyl, halogen, $(CH_2)_nNR^cR^d$, cyano, $C_{1-6}$ alkoxycarbonyl, carbamoyl, N-alkylcarbamoyl, N,N-dialkylcarbamoyl and carboxyl.

$R^c$ and $R^d$ are independently in hydrogen, $C_{1-6}$ alkyl, $C_{1-6}$ haloalkyl, $C_{1-6}$ acyl, $C_{1-6}$ sulfonyl, sulfamoyl $C_{1-3}$ alkylsulfamoyl, $C_{1-3}$ dialkylsulfamoyl, carbamoyl, $C_{1-3}$ alkylcarbamoyl, $C_{1-3}$ dialkylcarbamoyl.

X is OH, $C_{1-6}$ alkoxy or $NR^eR^f$.

$R^e$ and $R^f$ are independently hydrogen or $C_{1-6}$ alkyl.

n is zero or 1.

p is zero to three; or,

The present invention further includes pharmaceutically acceptable salts of compounds according to formula I which are with the scope of the claims.

The present invention also provides a method for treating a disease a Hepatitis C Virus (HCV) virus infection by administering a therapeutically effective quantity of a compound according to formula I to a patient in need thereof. The compound can be administered alone or co-administered with other antiviral compounds or immunomodulators.

The present invention also provides a method for inhibiting replication of HCV in a cell by administering a compound according to formula I in an amount effective to inhibit HCV.

The present invention also provides a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "- - -" drawn through a bond each refer to the point of attachment of a functional group or other chemical moiety to the rest of the molecule of which it is a part. Thus, for example:

MeC(=O)OR$^4$ wherein R$^4$=

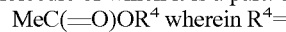

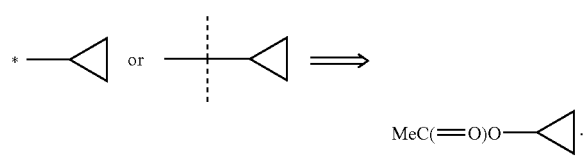

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— $\leftrightarrows$ —C(—OH)=CH—), amide/imidic acid (—C(=O)—NH— $\leftrightarrows$ —C(—OH)=N—) and amidine (—C(=NR)—NH— $\leftrightarrows$ —C(—NHR)=N—) tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formulae I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, .alpha.-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxillary) to produce diastereomers which can be separated by chromatography or by fractional crystallization after which time the chiral auxiliary is chemically removed to afford the pure enantiomers.

When compounds of formula I contain a basic center and suitable acid addition salts may be formed from acids which form non-toxic salts. Examples of salts of inorganic acids include the hydrochloride, hydrobromide, hydroiodide, chloride, bromide, iodide, sulphate, bisulphate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

In an embodiment of the present invention there is provided a compound according to formula I wherein A is a heteroaryl radical selected from the group consisting of 3-oxo-3,4-dihydro-pyrazin-2-yl, 3-oxo-2,3-dihydro-pyridazin-4-yl, 6-oxo-1,6-dihydro-pyrimidin-5-yl, 6-oxo-1,6-dihydro-[1,2,4]triazin-5-yl and 2,4-dioxo-1,2,3,4-tetrahydro-pyrimidin-5-yl said heteroaryl radical optionally substituted by halogen, $C_{1-6}$ alkyl, $C_{1-3}$ haloalkyl, $C_{1-6}$ alkoxy or benzyloxy. $R^1$ is hydrogen, hydroxy, $C_{1-3}$ hydroxyalkyl, COX or cyano. $R^2$ is (a) $-[C(R^6)_2]_p-Ar^1$, (b) $CR^{7a}=CR^{7b}Ar^1$; (c) $-NR^5COAr^1$ or (d) $CONR^5Ar^1$. $R^3$ is hydrogen, $C_{1-6}$ alkyl, $C_{1-6}$ haloalkyl, $C_{1-6}$ alkoxy, $C_{1-6}$ haloalkoxy, halogen or $R^3$ and $R^{4a}$ together are $CH_2-O$ and together with atoms to which they are attached form a 2,3-dihydrobenzofuran. $R^{4a}$, $R^{4b}$ and $R^{4c}$ (i) when taken independently are selected independently from $C_{1-3}$ alkyl, $C_{1-2}$ alkoxy, $C_{1-2}$ fluoroalkyl, hydroxy or halogen or (ii) when taken together, $R^{4a}$ and $R^{4b}$ together are $CH_{2-4}$ methylene and $R^{4c}$ is $C_{1-3}$ alkyl, $C_{1-2}$ alkoxy, $C_{1-2}$ fluoroalkyl or halogen, or (iii) either $R^8$ or $R^3$ and $R^{4a}$ together are $CH_2-O$ and together with atoms to which they are attached for a 2,3-dihydro-benzofuran and $R^{4b}$ and $R^{4c}$ are $C_{1-3}$ alkyl. $R^8$ is hydrogen, fluorine or $R^8$ and $R^{4a}$ together are $CH_2-O$ and together with atoms to which they are attached form a 2,3-dihydrobenzofuran. $R^5$ is hydrogen or $C_{1-6}$ alkyl. $R^6$ is independently in each occurrence hydrogen, $C_{1-6}$ alkyl, carboxy, $C_{1-6}$ alkoxycarbonyl or $C_{1-6}$ hydroxyalkyl. $R^{7a}$ and $R^{7b}$ are independently hydrogen or $C_{1-6}$ alkyl. $Ar^1$ is phenyl or pyridinyl, pyrimidinyl, pyrazinyl or pyridazinyl optionally independently substituted with one to three substituents selected from the group consisting of hydroxy, $C_{1-6}$ alkoxy, $C_{1-6}$ alkyl, $C_{1-6}$ hydroxyalkyl, halogen, $(CH_2)_nNR^cR^d$, cyano, $C_{1-6}$ alkoxycarbonyl, carbamoyl, N-alkylcarbamoyl, N,N-dialkylcarbamoyl, carboxyl, $SO_2NH_2$, $C_{1-6}$ alkylsulfinyl and $C_{1-6}$ alkylsulfonyl. $R^c$ and $R^d$ are independently in hydrogen, $C_{1-6}$ alkyl, $C_{1-6}$ haloalkyl, $C_{1-6}$ acyl, $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl, $C_{1-6}$ alkoxy-$C_{1-6}$ alkylsulfonyl, sulfamoyl, $C_{1-3}$ alkylsulfamoyl, $C_{1-3}$ dialkylsulfamoyl, carbamoyl, $C_{1-3}$ alkylcarbamoyl or $C_{1-3}$ dialkylcarbamoyl. X is OH, $C_{1-6}$ alkoxy or $NR^eR^f$. $R^e$ and $R^f$ are independently hydrogen or $C_{1-6}$ alkyl. n is zero or 1. p is zero to three. The embodiment further comprises a pharmaceutically acceptable salt of compounds according to formula I.

In one embodiment of the present invention there is provided a compound according to formula I where A, $R^1$, $R^2$, $R^3$, $R^{4a}$, $R^{4b}$, $R^{4c}$, $R^5$, $R^6$, $R^{7a}$, $R^{7b}$, $R^8$, $Ar^1$, $R^c$, $R^d$, $R^e$, $R^f$, X, n and p are as defined hereinabove. In all other embodiments provided below, substituents which can be present in each embodiment and which are not explicitly defined retain the broadest definition provided in the Summary of the Invention.

In a another embodiment of the present invention there is provided a compound according to formula I wherein A is 3-oxo-2,3-dihydro-pyridazin-4-yl.

In a another embodiment of the present invention there is provided a compound according to formula I wherein A is 3-oxo-2,3-dihydro-pyridazin-4-yl; $R^1$ is hydrogen or hydroxy; $R^2$ is (a) $-[C(R^6)_2]_p-Ar^1$, (b) $CR^{7a}=CR^{7b}Ar^1$ or (c) $-NR^5COAr^1$; $R^{4a}$, $R^{4b}$ and $R^{4c}$ are independently $C_{1-3}$ alkyl; $R^6$, $R^{7a}$ and $R^{7b}$ are hydrogen; and $Ar^1$ is phenyl optionally independently substituted with one to three substituents selected from the group consisting of hydroxy, $C_{1-6}$ alkoxy, $C_{1-6}$ alkyl, $C_{1-6}$ hydroxyalkyl, halogen, $(CH_2)_nNR^cR^d$.

In a another embodiment of the present invention there is provided a compound according to formula I wherein A is 3-oxo-2,3-dihydro-pyridazin-4-yl; $R^1$ is hydrogen or hydroxy; $R^2$ is (a) $-[C(R^6)_2]_p-Ar^1$, (b) $CR^{7a}=CR^{7b}Ar^1$ or (c) $-NR^5COAr^1$; either $R^8$ or $R^3$ and $R^{4a}$ together are $CH_2-O$ and together with atoms to which they are attached for a 2,3-dihydro-benzofuran and $R^{4b}$ and $R^{4c}$ are $C_{1-3}$ alkyl; $R^6$, $R^{7a}$ and $R^{7b}$ are hydrogen; and $Ar^1$ is phenyl or pyridinyl either optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_nNR^cR^d$.

In a another embodiment of the present invention there is provided a compound according to formula I wherein A is 3-oxo-2,3-dihydro-pyridazin-4-yl; $R^1$ is hydrogen; $R^2$ is $CR^{7a}=CR^{7b}Ar^1$; $R^{4a}$, $R^{4b}$ and $R^{4c}$ are and independently $C_{1-3}$ alkyl; $R^6$, $R^{7a}$ and $R^{7b}$ are hydrogen; $Ar^1$ is phenyl optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_nNR^cR^d$.

In a another embodiment of the present invention there is provided a compound according to formula I wherein A is 3-oxo-2,3-dihydro-pyridazin-4-yl; $R^1$ is hydrogen; $R^2$ is (a) —$[C(R^6)_2]_p$—$Ar^1$, (b) $CR^{7a}=CR^{7b}Ar^1$, $R^{4a}$, $R^{4b}$ and $R^{4c}$ are independently $C_{1-3}$ alkyl; $R^6$, $R^{7a}$ and $R^{7b}$ are hydrogen; and $Ar^1$ is phenyl substituted at least by $(CH_2)_nNR^cR^d$; $R^c$ is hydrogen or $C_{1-3}$ alkyl and $R^d$ is $C_{1-6}$ alkylsulfonyl.

In a another embodiment of the present invention there is provided a compound according to formula I wherein A is 3-oxo-2,3-dihydro-pyridazin-4-yl; $R^2$ is —$NR^5COAr^1$; $Ar^1$ is phenyl substituted at least by $(CH_2)_nNR^cR^d$, $R^c$ is hydrogen or $C_{1-3}$ alkyl and $R^d$ is $C_{1-6}$ alkylsulfonyl.

In a another embodiment of the present invention there is provided a compound according to formula I wherein A is 3-oxo-3,4-dihydro-pyrazin-2-yl.

In a another embodiment of the present invention there is provided a compound according to the formula I wherein A is 3-oxo-3,4-dihydro-pyrazin-2-yl; $R^1$ is hydrogen or hydroxy; $R^2$ is (a) —$[C(R^6)_2]_p$—$Ar^1$, (b) $CR^{7a}=CR^{7b}Ar^1$ or (c) —$NR^5COAr^1$; $R^{4a}$, $R^{4b}$ and $R^{4c}$ are independently $C_{1-3}$ alkyl; $R^6$, $R^{7a}$ and $R^{7b}$ are hydrogen; and $Ar^1$ is phenyl optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_nNR^cR^d$.

In a another embodiment of the present invention there is provided a compound according to the formula I wherein A is 3-oxo-3,4-dihydro-pyrazin-2-yl; $R^1$ is hydrogen; $R^2$ is $CR^{7a}=CR^{7b}Ar^1$; $R^{4a}$, $R^{4b}$ and $R^{4c}$ are independently $C_{1-3}$ alkyl; $R^6$, $R^{7a}$ and $R^{7b}$ are hydrogen; and $Ar^1$ is phenyl optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_nNR^cR^d$.

In a tenth embodiment of the present invention there is provided a compound according to the formula I wherein A is 3-oxo-3,4-dihydro-pyrazin-2-yl; $R^1$ is hydrogen or hydroxy; $R^2$ is (b) $CR^{7a}=CR^{7b}Ar^1$; $R^{4a}$, $R^{4b}$ and $R^{4c}$ are independently $C_{1-3}$ alkyl; $R^6$, $R^{7a}$ and $R^{7b}$ are hydrogen; $Ar^1$ is phenyl substituted at least by $(CH_2)_nNR^cR^d$, $R^c$ is hydrogen or $C_{1-3}$ alkyl and $R^d$ is $C_{1-6}$ alkylsulfonyl.

In another embodiment of the present invention there is provided a compound according to the formula I wherein A is 3-oxo-3,4-dihydro-pyrazin-2-yl; $R^1$ is hydrogen or hydroxy; $R^2$ is (c) —$NR^5COAr^1$; $R^{4a}$, $R^{4b}$ and $R^{4c}$ are independently $C_{1-3}$ alkyl; $R^6$ is hydrogen; $Ar^1$ is phenyl substituted at least by $(CH_2)_nNR^cR^d$, $R^c$ is hydrogen or $C_{1-3}$ alkyl and $R^d$ is $C_{1-6}$ alkylsulfonyl.

In a another embodiment of the present invention there is provided a compound according to formula I wherein A is optionally substituted 6-oxo-1,6-dihydro-pyrimidin-5-yl.

In another embodiment of the present invention there is provided a compound according to formula I wherein A is optionally substituted 6-oxo-1,6-dihydro-pyrimidin-5-yl and $R^2$ is optionally substituted naphthyl.

In another embodiment of the present invention there is provided a compound according to formula I wherein A is optionally substituted 6-oxo-1,6-dihydro-pyrimidin-5-yl; $R^2$ is optionally substituted 6-$((CH_2)_nNR^cR^d)$-naphth-2-yl, $R^c$ is hydrogen or $C_{1-3}$ alkyl and $R^d$ is $C_{1-6}$ alkylsulfonyl.

In another embodiment of the present invention there is provided a compound according to formula I wherein A is optionally substituted 6-oxo-1,6-dihydro-pyrimidin-5-yl, $R^{4a}$, $R^{4b}$ and $R^{4c}$ are independently $C_{1-3}$ alkyl; $R^2$ is optionally substituted 6-$((CH_2)_nNR^cR^d)$— naphth-2-yl, $R^c$ is hydrogen or $C_{1-3}$ alkyl and $R^d$ is $C_{1-6}$ alkylsulfonyl-naphthyl.

In another embodiment of the present invention there is provided a compound according to formula I wherein A is optionally substituted 6-oxo-1,6-dihydro-pyrimidin-5-yl, $R^8$ or $R^3$ and $R^{4a}$ together are $CH_2$—O and together with atoms to which they are attached for a 2,3-dihydro-benzofuran; $R^2$ is optionally substituted 6-$((CH_2)_nNR^cR^d)$-naphth-2-yl, $R^c$ is hydrogen or $C_{1-3}$ alkyl and $R^d$ is $C_{1-6}$ alkylsulfonyl.

In another embodiment of the present invention there is provided a compound according to formula I wherein A is optionally substituted 6-oxo-1,6-dihydro-pyrimidin-5-yl, either $R^{4a}$, $R^{4b}$ and $R^{4c}$ are fluoro or $R^{4a}$ is trifluoromethyl and $R^{4b}$ and $R^{4c}$ are hydrogen; $R^2$ is optionally substituted 6-$((CH_2)_nNR^cR^d)$-naphth-2-yl, $R^c$ is hydrogen or $C_{1-3}$ alkyl and $R^d$ is $C_{1-6}$ alkylsulfonyl.

In another embodiment of the present invention there is provided a compound according to the formula I wherein A is optionally substituted 6-oxo-1,6-dihydro-pyrimidin-5-yl; $R^1$ is hydrogen or hydroxy; $R^2$ is (a) $CR^{7a}=CR^{7b}Ar^1$ or (b) —$NR^5COAr^1$; $R^{4a}$, $R^{4b}$ and $R^{4c}$ are independently $C_{1-3}$ alkyl; $R^6$, $R^{7a}$ and $R^{4b}$ are hydrogen; and $Ar^1$ is phenyl or pyridinyl either optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_nNR^cR^d$.

In another embodiment of the present invention there is provided a compound according to formula I wherein A is 6-oxo-1,6-dihydro-[1,2,4]triazin-5-yl.

In another embodiment of the present invention there is provided a compound according to the formula I wherein A is optionally substituted 6-oxo-1,6-dihydro-[1,2,4]triazin-5-yl; $R^1$ is hydrogen; $R^2$ is $CR^{7a}=CR^{7b}Ar^1$; $R^{4a}$, $R^{4b}$ and $R^{4c}$ are independently $C_{1-3}$ alkyl; $R^6$, $R^{7a}$ and $R^{7b}$ are hydrogen; and $Ar^1$ is phenyl optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_nNR^cR^d$.

In another embodiment of the present invention there is provided a compound according to formula I wherein A is optionally substituted 6-oxo-1,6-dihydro-[1,2,4]triazin-5-yl; $R^1$ is hydrogen or hydroxy; $R^2$ is optionally substituted naphthyl; $R^{4a}$, $R^{4b}$ and $R^{4c}$ are independently $C_{1-3}$ alkyl; $R^6$, $R^{7a}$ and $R^{7b}$ are hydrogen; and $Ar^1$ is phenyl optionally independently substituted with one to three substituents selected from the group consisting of hydroxy, $C_{1-6}$ alkoxy, $C_{1-6}$ alkyl, $C_{1-6}$ hydroxyalkyl, halogen, $(CH_2)_nNR^cR^d$.

In an another embodiment of the present invention there is provided a compound according to formula I wherein A is 2,4-dioxo-1,2,3,4-tetrahydro-pyrimidin-5-yl.

In another embodiment of the present invention there is provided a compound according to the formula I wherein A is optionally substituted 2,4-dioxo-1,2,3,4-tetrahydro-pyrimidin-5-yl; $R^1$ is hydrogen; $R^2$ is $CR^{7a}=CR^{7b}Ar^1$; $R^{4a}$, $R^{4b}$ and $R^{4c}$ are independently $C_{1-3}$ alkyl; $R^6$, $R^{7a}$ and $R^{7b}$ are hydrogen; and $Ar^1$ is phenyl optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_nNR^cR^d$.

In another embodiment of the present invention there is provided a compound according to formula I wherein A is 4,6-dioxo-2-methyl-1,4,5,6-tetrahydro-pyrimidin-5-yl.

In another embodiment of the present invention there is provided a compound according to the formula I wherein A is optionally substituted 4,6-dioxo-2-methyl-1,4,5,6-tetrahydro-pyrimidin-5-ylw; $R^2$ is hydrogen; $R^2$ is $CR^{7a}=CR^{7b}Ar^1$; $R^{4a}$, $R^{4b}$ and $R^{4c}$ are independently $C_{1-3}$ alkyl; $R^6$, $R^{7a}$ and $R^{7b}$ are hydrogen; and $Ar^1$ is phenyl optionally independently substituted with one to three substituents selected from the group consisting of hydroxy, $C_{1-6}$ alkoxy, $C_{1-6}$ alkyl, $C_{1-6}$ hydroxyalkyl, halogen, $(CH_2)_n NR^c R^d$.

In another embodiment of the present invention there is provided a compound according to formula I where A, $R^1$, $R^2$, $R^3$, $R^{4a}$, $R^{4b}$, $R^{4c}$, $R^5$, $R^6$, $R^{7a}$, $R^{7b}$, $R^8$, $Ar^1$, $R^c$, $R^d$, $R^e$, $R^f$, X, n and p are as defined hereinabove which compound is selected from compounds I-1 to I-41 and I-43 in TABLE 1.

In another embodiment of the present invention there is provided a method of treating a HCV infection in a patient in need thereof comprising administering a therapeutically effective amount of a compound according to formula I wherein A, $R^1$, $R^2$, $R^3$, $R^{4a}$, $R^{4b}$, $R^{4c}$, $R^5$, $R^6$, $R^{7a}$, $R^{7b}$, $R^8$, $Ar^1$, $R^c$, $R^d$, $R^f$, X, n and p are as defined hereinabove.

In another embodiment of the present invention there is provide a method of treating a HCV infection in a patient in need thereof comprising co-administering a therapeutically effective amount of a compound according to formula I wherein A, $R^1$, $R^2$, $R^3$, $R^{4a}$, $R^{4b}$, $R^{4c}$, $R^5$, $R^6$, $R^{7a}$, $R^{7b}$, $R^8$, $Ar^1$, $R^c$, $R^d$, $R^e$, $R^f$, X, n and p are as defined herein above and at least one immune system modulator and/or at least one antiviral agent that inhibits replication of HCV.

In another second embodiment of the present invention there is provide a method of treating a disease caused by HCV in a patient in need thereof comprising co-administering a therapeutically effective amount of a compound according to formula I wherein A, $R^1$, $R^2$, $R^3$, $R^{4a}$, $R^{4b}$, $R^{4c}$, $R^5$, $R^6$, $R^{7a}$, $R^{7b}$, $R^8$, $Ar^1$, $R^c$, $R^d$, $R^e$, $R^f$, X, n and p are as defined herein above and at least one immune system modulator selected from interferon, a chemically derivatized interferon, interleukin, tumor necrosis factor or colony stimulating factor.

In another embodiment of the present invention there is provide a method of treating a HCV infection in a patient in need thereof comprising co-administering a therapeutically effective amount of a compound according to formula I wherein A, $R^1$, $R^2$, $R^3$, $R^{4a}$, $R^{4b}$, $R^{4c}$, $R^5$, $R^6$, $R^{7a}$, $R^{7b}$, $R^8$, $Ar^1$, $R^c$, $R^d$, $R^e$, $R^f$, X, n and p are as defined herein above and an interferon or a chemically derivatized interferon.

In another embodiment of the present invention there is provide a method of treating a HCV infection in a patient in need thereof comprising co-administering a therapeutically effective amount of a compound according to formula I wherein A, $R^1$, $R^2$, $R^3$, $R^{4a}$, $R^{4b}$, $R^{4c}$, $R^5$, $R^6$, $R^{7a}$, $R^{7b}$, $R^8$, $Ar^1$, $R^c$, $R^d$, $R^e$, $R^f$, X, n and p are as defined herein above and at least one other antiviral compound selected from the group consisting of a HCV protease inhibitor, another HCV polymerase inhibitor, a HCV helicase inhibitor, a HCV primase inhibitor and a HCV fusion inhibitor.

In another embodiment of the present invention there is provided a method for inhibiting replication of HCV in a cell by delivering a compound according to formula I wherein A, $R^1$, $R^2$, $R^3$, $R^{4a}$, $R^{4b}$, $R^{4c}$, $R^5$, $R^6$, $R^{7a}$, $R^{7b}$, $R^8$, $Ar^1R^c$, $R^d$, $R^e$, $R^f$, X, n and p are as defined herein above.

In another embodiment of the present invention there is provided a composition comprising a compound according to formula I wherein A, $R^1$, $R^2$, $R^3$, $R^{4a}$, $R^{4b}$, $R^{4c}$, $R^5$, $R^6$, $R^{7a}$, $R^{7b}$, $R^8$, $Ar^1R^c$, $R^d$, $R^e$, $R^f$, X, n and p are as defined herein above admixed with at least one pharmaceutically acceptable carrier, diluent or excipient.

The term "alkyl" as used herein without further limitation alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, lower alkyl groups include methyl, ethyl, propyl, iso-propyl, n-butyl, tert-butyl, tert-butyl, neopentyl, hexyl, and octyl.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (hetero)aryl refers to either an aryl or a heteroaryl group.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —$CH_2$CH(i-Pr)$CH_2$—), unless otherwise indicated. $C_{0-4}$ alkylene refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 12-fluoroethyl, 2-chloroethyl, 2-bromoethyl, 2,2-dichloroethyl, 3-bromopropyl or 2,2,2-trifluoroethyl. The term "fluoroalkyl" as used herein refers to a haloalkyl moiety wherein fluorine is the halogen.

The term "halogen" or "halo" as used herein means fluorine, chlorine, bromine, or iodine.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The terms "alkoxycarbonyl" and "aryloxycarbonyl" as used herein denotes a group of formula —C(═O)OR wherein R is alkyl or aryl respectively and alkyl and aryl are as defined herein.

The term "cyano" as used herein refers to a carbon linked to a nitrogen by a triple bond, i.e., —C≡N. The term "nitro" as used herein refers to a group —$NO_2$. The term "carboxy" as used herein refers to a group $CO_2H$.

The term "acyl" (or "alkanoyl") as used herein denotes a group of formula —C(═O)R wherein R is hydrogen or lower alkyl as defined herein. The term or "alkylcarbonyl" as used herein denotes a group of formula C(═O)R wherein R is alkyl as defined herein. The term $C_{1-6}$ acyl or "alkanoyl" refers to a group —C(═O)R contain 1 to 6 carbon atoms. The $C_1$ acyl group is the formyl group wherein R═H and a $C_6$ acyl group refers to hexanoyl when the alkyl chain is unbranched. The term "arylcarbonyl" or "aroyl" as used herein means a group of formula C(═O)R wherein R is an aryl group; the term "benzoyl" as used herein an "arylcarbonyl" or "aroyl" group wherein R is phenyl.

The term "cyclic amine" as used herein refers to a saturated carbon ring, containing from 3 to 6 carbon atoms as defined above, and wherein at least one of the carbon atoms is replaced by a heteroatom selected from the group consisting of N, O or S for example, piperidine, piperazine, morpholine, thiomorpholine, di-oxo-thiomorpholine, pyrrolidine, pyrazoline, imidazolidine, azetidine wherein the cyclic carbon atoms are optionally substituted by one or more substituents, selected from the group consisting of halogen, hydroxy, phenyl, lower alkyl, lower alkoxy or 2-hydrogen atoms on a carbon are both replace by oxo (═O). When the cyclic amine is a piperazine, one nitrogen atom can be optionally substituted by $C_{1-6}$ alkyl, $C_{1-6}$ acyl, $C_{1-6}$ alkylsulfonyl.

The terms "alkylsulfonyl" and "arylsulfonyl" as used herein denotes a group of formula —S(═O)$_2$R wherein R is alkyl or aryl respectively and alkyl and aryl are as defined herein. The term $C_{1-3}$ alkylsulfonylamino as used herein refers to a group $RSO_2NH$— wherein R is a $C_{1-3}$ alkyl group as defined herein. The term "sulfonylamino" may be use as a prefix while "sulfonylamide" is the corresponding suffix. The terms $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl refer to a compound, S(═O)$_2$R wherein R is $C_{1-6}$ haloalkyl, $C_{3-7}$ cycloalkyl, $C_{3-7}$ cycloalkyl-$C_{1-3}$ alkyl and $C_{1-6}$ alkoxy-$C_{1-6}$ alkyl, respectively The term "sulfamoyl" as herein refers to the radical —S(O)$_2$NH$_2$. The terms "N-alkylsulfamoyl" and "N,N-dialkylsulfamoyl" as used herein refers to the radical —S(O)$_2$NR'R'', wherein R' and R'' are hydrogen and lower alkyl and R' and R'' are independently lower alkyl respectively. Examples of N-alkylsulfamoyl substituents include, but are not limited to methylaminosulfonyl, iso-propylaminosulfonyl. Examples of N,N-dialkylsulfamoyl substituents include, but are not limited to dimethylaminosulfonyl, iso-propyl-methylaminosulfonyl.

The term "carbamoyl" as used herein means the radical —CONH$_2$. The prefix "N-alkylcabamoyl" and "N,N-dialkylcarbamoyl" means a radical CONHR' or CONR'R'' respectively wherein the R' and R'' groups are independently alkyl as defined herein. The prefix N-arylcabamoyl" denotes the radical CONHR' wherein R' is an aryl radical as defined herein.

The term "pyridine" ("pyridinyl") refers to a six-membered heteroaromatic ring with one nitrogen atom. The terms "pyrimidine" (pyrimidinyl), "pyrazine" ("pyrazinyl") and "pyridazine" ("pyridazinyl") refer to a six-membered non-fused heteroaromatic ring with two nitrogen atoms disposed in a 1,3, a 1,4 and a 1,2 relationship respectively. The respective radical names are in parentheses.

To avoid any ambiguity, as used herein the terms (i) 3-oxo-3,4-dihydro-pyrazin-2-yl, (ii) 3-oxo-2,3-dihydro-pyridazin-4-yl, (iii) 6-oxo-1,6-dihydro-pyrimidin-5-yl, (iv) 6-oxo-1,6-dihydro-[1,2,4]triazin-5-yl, (v) 2,4-dioxo-1,2,3,4-tetrahydro-pyrimidin-5-yl and (vi) 4,6-dioxo-1,4,5,6-tetrahydro-pyrimidin-5-yl refer to the following moieties

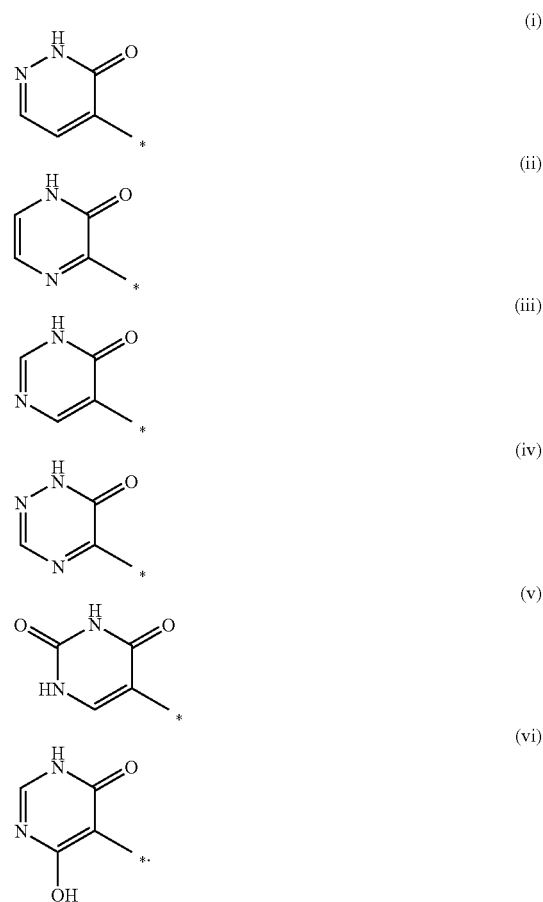

The phrase "substituted at least by (CH$_2$)NR$^c$R$^{d}$" simply indicates the ring is substituted by (CH$_2$)$_n$NR$_c$R$^d$ but other additional optional substitutions within the scope of the claim are permitted.

In one embodiment, the compounds of the present invention according to formula I are used in combination with other active therapeutic ingredients or agents to treat patients with an HCV viral infection. According to the present invention, the active therapeutic ingredient used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, nucleoside inhibitors of HCV polymerase, non-nucleoside inhibitors of HCV polymerase, and other drugs for treating HCV, or mixtures thereof.

Examples of the nucleoside NS5b polymerase inhibitors include, but are not limited to NM-283, valopicitabine, R1626, PSI-6130 (R1656), IDX184 and IDX102 (Idenix) BILB 1941.

Examples of the non-nucleoside NS5b polymerase inhibitors include, but are not limited to HCV-796 (ViroPharma and Wyeth), MK-0608, MK-3281 (Merck), NM-107, R7128 (R4048), VCH-759, GSK625433 and GSK625433 (Glaxo), PF-868554 (Pfizer), GS-9190 (Gilead), A-837093 and A848837 (Abbot Laboratories), ANA598 (Anadys Pharmaceuticals); GL100597 (GNLB/NVS), VBY 708 (ViroBay), benzimidazole derivatives (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1), benzo-1,2,4-thiadiazine derivatives (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed Oct. 31, 2003), 1,1-dioxo-4H-benzo[1,4]thiazin-3-yl derivatives (J. F. Blake et al. in U.S. Patent Publication US20060252785 and 1,1-dioxo-benzo[d]isothazol-3-yl compounds (J. F. Blake et al. in U.S. Patent Publication 2006040927).

Examples of the HCV NS3 protease inhibitors include, but are not limited to SCH-503034 (Schering, SCH-7), VX-950 (telaprevir, Vertex), BILN-2065 (Boehringer-Ingelheim, BMS-605339 (Bristo Myers Squibb), and ITMN-191 (Intermune).

Examples of the interferons include, but are not limited to pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen and actimmune, IFN-omega with DUROS, albuferon, locteron, Albuferon, Rebif, oral interferon alpha, IFNalpha-2b XL, AVI-005, PEG-Infergen, and pegylated IFN-beta.

Ribavirin analogs and the ribavirin prodrug viramidine (taribavirin) have been administered with interferons to control HCV. Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride ($Boc_2O$), benzyl (Bn), butyl (Bu), Chemical Abstracts Registration Number (CASRN), benzyloxycarbonyl (CBZ or Z), carbonyl diimidazole (CDI), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), $MeSO_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-$BuMe_2Si$ (TBDMS), triethylamine (TEA or $Et_3N$), triflate or $CF_3SO_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n-), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

Compounds encompassed by the present invention are substituted 3-phenyl-1H-pyridin-2-one derivatives. The following numbering scheme is used to refer to the substitution sites on the core substructure.

TABLE I

| Cpd. No. | Structure | ms[1] | mp | NS5B pol inhibition[2] IC$_{50}$ |
|---|---|---|---|---|
| I-1 | 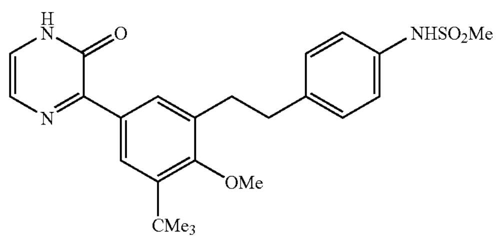 | 456 | 238.0-240.0 | 0.015 |
| I-2 | 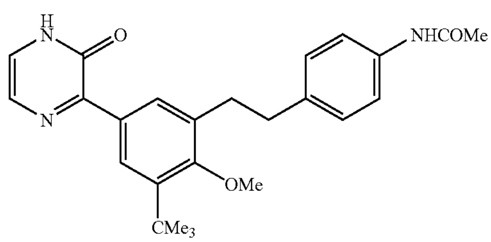 | 420 | 181.0-185.0 | 0.71 |
| I-3 | 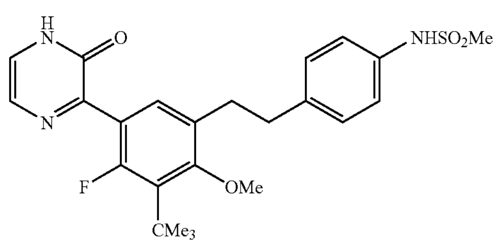 | 474 | 130.0-132.0 | 0.041 |
| I-4 | 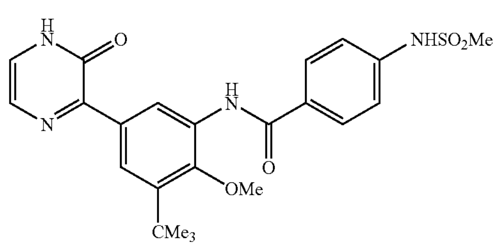 | 471 | | 0.006 |
| I-5 | 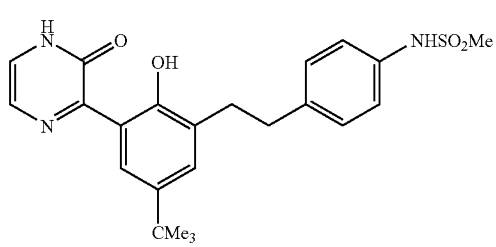 | 442 | | 0.092 |

TABLE I-continued

| Cpd. No. | Structure | ms[1] | mp | NS5B pol inhibition[2] IC$_{50}$ |
|---|---|---|---|---|
| I-6 | (pyrazinone with 3-(2-hydroxy-5-tert-butyl-3-styryl)phenyl, stilbene to 4-NHSO$_2$Me phenyl) | 440 | 280.0-282.0 | 0.454 |
| I-7 | (uracil-5-yl with 3-tert-butyl-4-methoxy-5-styryl-phenyl, stilbene to 2-fluoro-4-NHSO$_2$Me phenyl) | 488 | | 0.0003 |
| I-8 | (N1-methyluracil-5-yl with 3-tert-butyl-4-methoxy-5-styryl-phenyl, stilbene to 4-NHSO$_2$Me phenyl) | 484 | >300 | 0.0013 |
| I-9 | (pyridazinone-4-yl with 3-tert-butyl-4-methoxy-5-styryl-phenyl, stilbene to 2-CO$_2$H-4-NHSO$_2$Me phenyl) | 496 | | 0.0002 |
| I-10 | (pyrazinone-3-yl with 3-tert-butyl-5-styryl-phenyl, stilbene to 4-NHSO$_2$Me phenyl) | 424 | 283.0-285.0 | 0.007 |

TABLE I-continued

| Cpd. No. | Structure | ms[1] | mp | NS5B pol inhibition[2] IC$_{50}$ |
|---|---|---|---|---|
| I-11 | 3-(pyrazin-2(1H)-one-3-yl)-5-[(E)-2-(4-methanesulfonamidophenyl)vinyl]-4-methoxy-3-tert-butylphenyl | 454 | | 0.004 |
| I-12 | 4-(3-methyl-5-tert-butylphenyl)pyridazin-3(2H)-one | 243 | 175.0-176.0 | 0.390 |
| I-13 | 4-{3-[(E)-2-(4-methanesulfonamidophenyl)vinyl]-4-methoxy-5-tert-butylphenyl}pyridazin-3(2H)-one | 454 | 240.0-242.0 | 0.004 |
| I-14 | 4-{3-[(E)-2-phenylvinyl]-4-methoxy-5-tert-butylphenyl}pyridazin-3(2H)-one | 361 | 100.0-102.0 | 0.007 |
| I-15 | 4-{3-[(E)-2-(4-methanesulfonamidophenyl)vinyl]-5-tert-butylphenyl}pyridazin-3(2H)-one | 424 | | 0.003 |

TABLE I-continued

| Cpd. No. | Structure | ms[1] | mp | NS5B pol inhibition[2] IC$_{50}$ |
|---|---|---|---|---|
| I-16 | 4-(4-methoxy-3-tert-butylphenyl)pyridazin-3(2H)-one | 259 | 202.0-204.0 | 0.132 |
| I-17 | 6-methyl-4-[3-((E)-2-(4-methanesulfonylaminophenyl)vinyl)-5-tert-butyl-4-methoxyphenyl]pyridazin-3(2H)-one | 468 | 292.0-294.0 | 0.01 |
| I-18 | 5-chloro-4-[3-((E)-2-(4-methanesulfonylaminophenyl)vinyl)-5-tert-butyl-4-methoxyphenyl]pyridazin-3(2H)-one | 458 | 234.0-236.0 | |
| I-19 | 4-amino-N-[5-(6-oxo-1,6-dihydropyridazin-4-yl)-3-tert-butyl-2-methoxyphenyl]benzamide | 393 | 174.0-176.0 | 0.015 |
| I-20 | 4-(2,2,2-trifluoroethylamino)-N-[5-(6-oxo-1,6-dihydropyridazin-4-yl)-3-tert-butyl-2-methoxyphenyl]benzamide | 475 | 250.0-252.0 | 0.005<br>0.003[2] |

TABLE I-continued

| Cpd. No. | Structure | ms[1] | mp | NS5B pol inhibition[2] IC$_{50}$ |
|---|---|---|---|---|
| I-21 | pyridazinone-dimethylbenzofuran-stilbene-NHSO$_2$Me | 438 | 255.0-257.0 | 0.002[2] |
| I-22 | pyrimidinone-(OMe,CMe$_3$)phenyl-stilbene-NHSO$_2$Me | 454 | 253.0-255.0 | 0.002[2] |
| I-23 | pyrazinone-dimethylbenzofuran-stilbene-NHSO$_2$Me | 438 | 302.0-304.0 | 0.019[2] |
| I-24 | BnO-pyrimidinone-(OMe,CMe$_3$)phenyl-stilbene-(CO$_2$Me)-NHSO$_2$Me | 618 | | 0.011[2] |
| I-25 | uracil-(OMe,CMe$_3$)phenyl-stilbene-NHSO$_2$Me | 470 | >300 | 0.0011 |

TABLE I-continued

| Cpd. No. | Structure | ms[1] | mp | NS5B pol inhibition[2] IC$_{50}$ |
|---|---|---|---|---|
| I-26 | 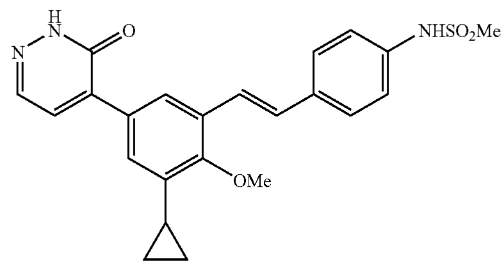 | 428 | 269.0-271.0 | 0.0021 |
| I-27 | 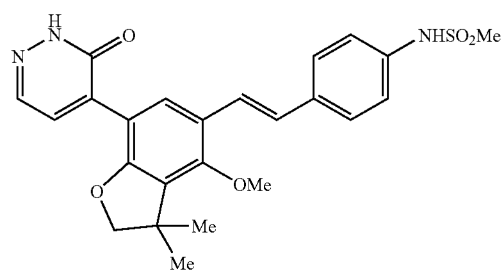 | 468 | | 0.0003 |
| I-28 | 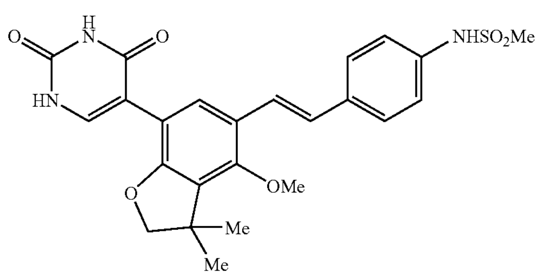 | 484 | >300 | 0.0006 |
| I-29 | 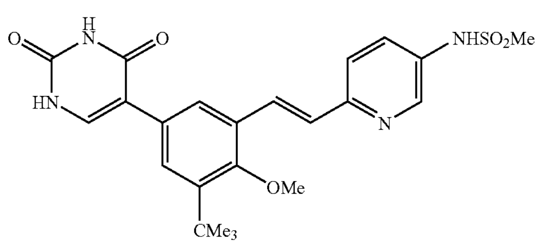 | 471 | | 0.0012 |
| I-30 | 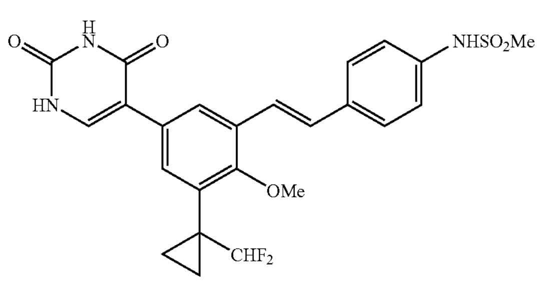 | 504 | 292.0-295.0 | 0.0003 |

TABLE I-continued

| Cpd. No. | Structure | ms[1] | mp | NS5B pol inhibition[2] IC$_{50}$ |
|---|---|---|---|---|
| I-31 | 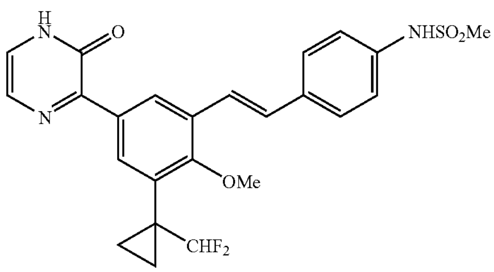 | 488 | 241.0-243.0 | 0.0003 |
| I-32 | 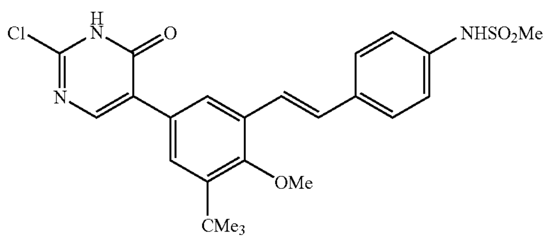 | | >300 | 0.005 |
| I-33 | 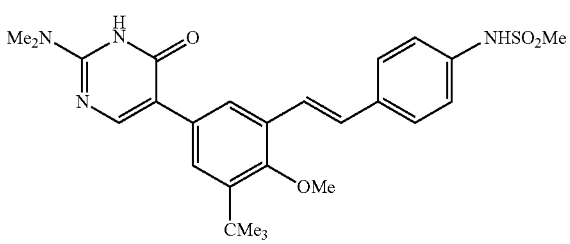 | 497 | >300 | 0.0026 |
| I-34 | 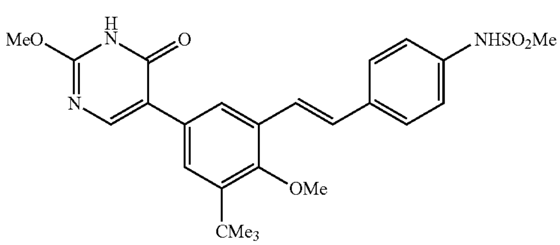 | 484 | 296.0-299.0 | 0.0006 |
| I-35 | 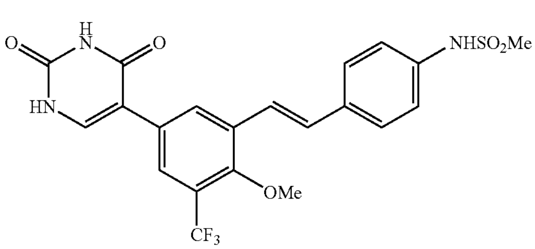 | 480 [M − H] | 255.0-258.0 | 0.0005 |

TABLE I-continued

| Cpd. No. | Structure | ms[1] | mp | NS5B pol inhibition[2] IC$_{50}$ |
|---|---|---|---|---|
| I-36 | 5-aryl-1,2,4-triazin-6(1H)-one with styryl-NHSO$_2$Me, OMe, CMe$_3$ substituents | 455 | 253.0-256.0 | 0.0004 |
| I-37 | 5-aryl-1,2,4-triazin-6(1H)-one with naphthyl-NHSO$_2$Me, OMe, CMe$_3$ | 478 [M − H] | 478 | 0.0007 |
| I-38 | uracil-5-yl with styryl-NHSO$_2$Me, OMe, CH$_2$CF$_3$ | 494 [M − H] | | 0.0014 |
| I-39 | 2-methoxypyrimidin-4(3H)-one-5-yl with styryl-NHSO$_2$Me, CH$_2$OMe, OMe, CMe$_3$ | 528 | | 0.0009 |

TABLE I-continued

| Cpd. No. | Structure | ms[1] | mp | NS5B pol inhibition[2] IC$_{50}$ |
|---|---|---|---|---|
| I-40 | 5-[3-methoxy-5-tert-butyl-phenyl with (E)-styryl-NHSO$_2$Me, CH$_2$OMe substituent] uracil | | 172.0-175.0 | 0.0028 |
| I-41 | 2-methyl-6-hydroxy-pyrimidinone with 3-methoxy-5-tert-butyl-phenyl (E)-styryl-NHSO$_2$Me | 484 | | 0.0004 |
| I-42 | uracil-5-yl with 3-methoxy-5-OCF$_3$-phenyl (E)-styryl-NHSO$_2$Me | 496 [M − H] | 202-205 | 0.0067 |
| I-43 | 2-methyl-pyrimidinone with 3-methoxy-5-tert-butyl-phenyl (E)-styryl-NHSO$_2$Me | | | 0.0011 |

[1] mass spectra reported as (M + H)$^+$
[2] IC$_{50}$ for inhibition of HCV NS5B polymerase (μM). See example 32
[3] IC$_{50}$ for inhibition of HCV NS5B polymerase (μM) as in Example 32 except RNA template concentration was 3 nM Compounds in following schemes are frequently depicted with generalized substituents to exemplify the general nature of the methodology. One skilled in the art will immediately appreciate that the nature of the R groups can be varied to afford the various compounds contemplated in this invention. Moreover, the reaction conditions are exemplary and alternative conditions are well known which can be substituted for the conditions described herein. The reaction sequences in the following examples are not meant to limit the scope of the invention as set forth in the claims.

SCHEME A

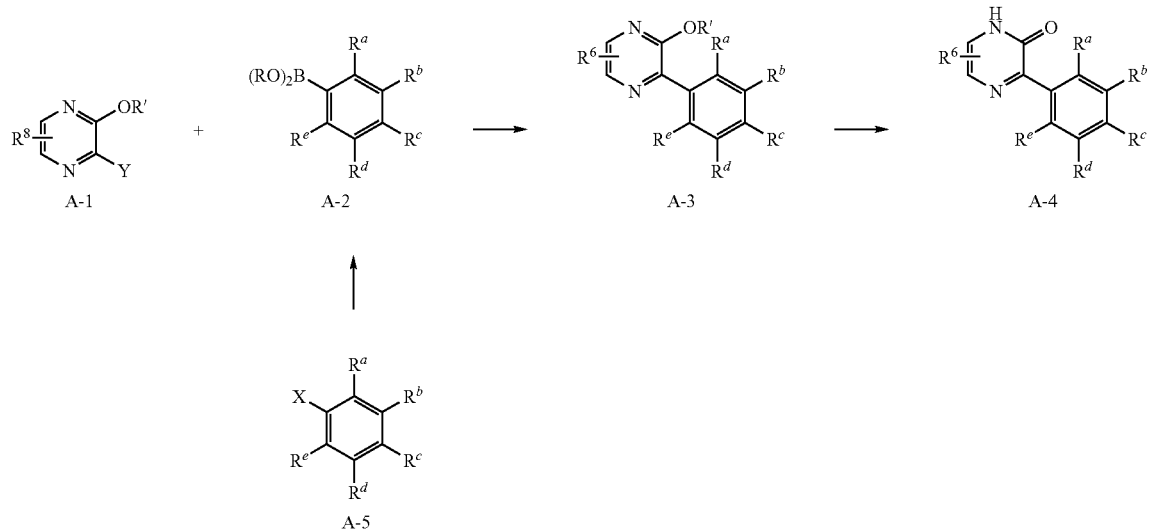

3-Aryl-1H-pyrazin-2-ones (A-4) can generally be prepared by a palladium-catalyzed Suzuki coupling of a 2-halo-3-alkoxy-pyrazine or 2-halo-3-aralkoxy-pyrazine (A-1) and a boronic acid or a pinacol-boronic acid esters [B(OR)$_2$ derivatives wherein both OR radicals taken together represent —OC(Me)$_2$CC(Me)$_2$O—] (A-2). The boronic esters are generally prepared by metallation of the corresponding aryl halide (A-5) and condensation with a suitable reactive boronic acid ester or dialkoxyboron halide or by Pd-catalyzed coupling with bis-(pincolato)diboron. Cleavage of either the 2-alkoxypyrazine (HBr/HOAc) or the 2-benzyloxy-pyrazine (catalytic hydrogenolysis or HBr/HOAc) affords the 1H-pyrazin-2-one.

The Suzuki coupling is a palladium-catalyzed coupling of a boronic acid with an aryl or vinyl halide or triflate. Typical catalysts include Pd(PPh$_3$)$_4$, PdCl$_2$(PPh$_3$)$_2$, Pd(OAc)$_2$ and PdCl$_2$(dppf). With PdCl$_2$(dppf), primary alkyl borane compounds can be coupled to aryl or vinyl halide or triflate without beta-elimination. The reaction can be carried out in a variety of organic solvents including toluene, THF, dioxane, DCE, DMF, DMSO, PhMe, MeOH and MeCN, aqueous solvents and under biphasic conditions. Reactions are typically run from about RT to about 150° C. Additives (e.g., CsF, KF, TlOH, NaOEt and KOH) frequently accelerate the coupling. Although there are numerous components in the Suzuki reaction including the particular palladium catalyst, the ligand, additives, solvent, temperature, etc., numerous protocols have been identified. Highly active catalysts have been described (see, e.g., R. Martin and S. L. Buchwald, Acc. Chem. Res. 2008 41(11):1461-73, J. P. Wolfe et al., J. Am. Chem. Soc. 1999 121(41):9550-9561 and A. F. Littke et al., J. Am. Chem. Soc. 2000 122(17):4020-4028). One skilled in the art will be able to identify a satisfactory protocol without undue experimentation.

Compounds of the present invention wherein R$^b$ is an optionally substituted (E)-styryl- or (E)-2-heteroarylvinyl radical are prepared from precursors wherein R$^b$ is an aldehyde utilizing a Wittig reaction or variant thereof. The requisite aldehyde can be prepared by formylation of an appropriately substituted phenol. The Wittig reaction is the reaction of an aldehyde or ketone with a triphenyl phosphonium ylide to afford an alkene and triphenylphosphine oxide. (A. Maercker, Org. React. 1965, 14, 270-490; A. W. Carruthers, Some Modern Methods of Organic Synthesis, Cambridge University Press, Cambridge, UK, 1971, pp 81-90) Wittig reactions are most commonly used to couple aldehydes and ketones to singly substituted phosphine ylides. The Wittig reagent is usually prepared from a phosphonium salt, which is in turn made by the reaction of Ph$_3$P with an alkyl or aralkyl halide. To form the Wittig reagent (ylide), the phosphonium salt is suspended in a solvent such as Et$_2$O or THF and a strong base such as phenyl lithium or n-butyl lithium is added. With simple ylides, the product is usually mainly the Z-isomer, although a lesser amount of the E-isomer also is often formed. This is particularly true when ketones are used. If the reaction is performed in DMF in the presence of LiI or NaI, the product is almost exclusively the Z-isomer. If the E-isomer is the desired product, the Schlosser modification may be used. Alternatively the Horner-Wadsworth-Emmons reaction (B. E. Maryanoff and A. B. Reitz, Chem. Rev. 1989 89:863-927) is the chemical reaction of stabilized phosphonate carbanions with aldehydes (or ketones) to produce predominantly E-alkenes. In contrast to phosphonium ylides used in the Wittig reaction, phosphonate-stabilized carbanions are more nucleophilic and more basic. Optionally substituted (E)-2-aryl ethyl- or (E)-2-heteroaryl-ethyl derivatives can be prepared by hydrogen of the olefinic linkage. Introduction of substituted aryl and substituted heteroaryl moieties is easily achieved by the Wittig and related olefination procedures.

Compounds of formula I wherein R$^2$ is CONR$^5$Ar$^1$ are prepared by oxidation of the corresponding aldehyde to the carboxylic acid. Oxidation of aldehydes to carboxylic acids is an extraordinarily common transformation in organic synthesis and a correspondingly large number of alternative procedures, conditions and reagents are available which permit the oxidation of almost any alcohol. Among the commonly used reagents are potassium or sodium permanganate in acidic, basic or neutral solution (A. J. Fatiadi, Synthesis 1987 85-127), chromium (IV) (S. V. Ley and A. Machlin, In Comprehensive Organic Synthesis, B. M. Trost and I. Fleming Eds, Pergamon Press, NY 1981, v. 7, pp. 251-289), silver oxide and sodium chlorite (G. A. Kraus and B. Roth, J. Org. Chem. 1980 45:4825).

Transformation of a carboxylic acid into an amide can be effected by preparing an activated carboxylic acid such as an acid chloride or a symmetrical or mixed acid anhydride and reacting the activated derivative with an amines in a solvent such as DMF, DCM, THF, with or without water as a co-solvent, and the like at temperatures between 0° and 60° C. generally in the presence of a base such as $Na_2CO_3$, $NaHCO_3$, $K_2CO_3$, DIPEA, TEA or pyridine and the like to afford an amide. Carboxylic acids are converted into their acid chlorides using standard reagents well known to one skilled in the art, such as thionyl chloride, oxalyl chloride, phosphoryl chloride and the like. Those reagents can be used in presence of bases such as DIPEA, TEA or pyridine in inert solvent such as dichloromethane or dimethylformamide.

Alternatively a carboxylic acid can be converted in situ into activated acids by different procedures developed for peptide coupling and well-known to those skilled in the art. These activated acids were reacted directly with the amines to afford amides. Said activation can involve the use of an activating agent like EDIC, DCC, HOBt, BOP, PyBrOP or 2-fluoro-1-methylpyridinium p-toluenesulphonate (Mukaiyama's reagent) and the like with or without a base such NMM, TEA or DIPEA in an inert solvent such as DMF or DCM at temperatures between 0° C. and 60° C. The reaction may alternatively be carried out in presence of O-(7-azabenzotriazol-1-yl)-N,N,N',N'-tetramethyluronium hexafluorophosphate (HATU) or 1-hydroxy-7-azabenzotriazole (HOAt) and TEA or DIPEA in DMF, DCM or THF. (*Organic Synthesis*, E. Winterfeldt, ed., vol. 6, Pergamon Press, Oxford 1991 pp. 381-411; see R. C. Larock, *Comprehensive Organic Transformations—A Guide to Functional Group Preparations* 1989, VCH Publishers Inc., New York; pp. 972-976)

Compounds of formula wherein $R^2$ is $NR^5COAr^1$ are prepared from the corresponding nitrobenzene (A-2, $R^b = NO_2$) which, in turn, are available by nitration of an appropriately substituted phenol or anisole. Reduction of a nitro group to an amine can be accomplished with a metal reducing agent such as Fe, Sn or Zn, in a reaction inert solvent, e.g. MeOH, EtOH, EtOAc, benzene, toluene, xylene, o-dichlorobenzene, DCM, DCE, THF, dioxane, or mixtures thereof. If desired, when the reducing reagent is Fe, Sn or Zn, the reaction is carried out under acidic conditions in the presence of water. The reduction may be carried out by hydrogenation in the presence of a metal catalyst, e.g. nickel catalysts such as Raney nickel, palladium catalysts such as Pd/C, platinum catalysts such as $PtO_2$, or ruthenium catalysts such as $RuCl_2(Ph_3P)_3$ under $H_2$ atmosphere or in the presence of hydrogen sources such as hydrazine or formic acid. If desired, the reaction is carried out under acidic conditions, e.g., in the presence of HCl or HOAc. The reduction may also be carried out in the presence of a suitable hydride reducing agent such as $LiAlH_4$ or $LiBH_4$ in an inert solvent. For the preparation of stilbene derivatives, reduction of the nitro group with Sn, Fe or Zn can be used to preserve the olefinic linkage. Formation of the amide can then carried out as described above.

Alternatively, compounds of formula I wherein $R^2$ is $NR^5COAr^1$ are prepared from the corresponding bromobenzene (A-2, $R^b = Br$) by a copper-catalyzed amidation of an aryl halide. (C. P. Jones et al., *J. Org. Chem.* 2007 72(21): 7968-7973; A. Klapars et al., *J. Am. Chem. Soc.* 2002 124 (25):7421-7428) The couplings can be carried out with an amide and an aryl iodide, chloride or bromide in the presence of CuI and 1,2-diamine ligands.

One skilled in the art will appreciate that the sequence of the transformations is not critical and, e.g., the $R^b$ substituent can be elaborated prior to coupling with the pyrazine fragment. (SCHEME B)

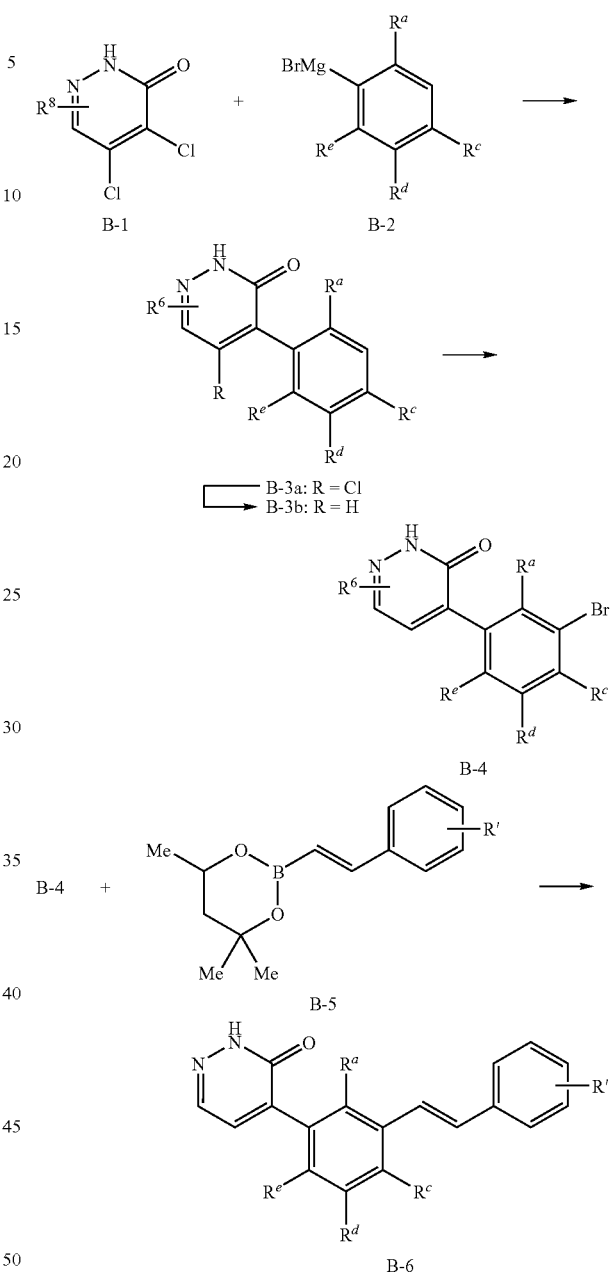

SCHEME B

4-Aryl-2H-pyridazin-3-one (B-3b) are prepared by condensation of an optionally substituted 4,5-dichloro-2H-pyridazin-3-one (B-1) and an aryl Grignard reagent to afford the 5-chloro-4-aryl-2H-pyridazin-3-one (B-3a) which is reductively dechlorinated to yield B-3b and subsequently brominated to afford B-4. The 2-(hetero)arylvinyl radical is introduced by a palladium-catalyzed Suzuki coupling using a 2 (hetero)aryl-vinyl boronate ester B-5. Alternatively, a 3-oxo-2,3-dihydro-pyridazin-4-yl boronic acid or an ester thereof (e.g. 108, example 9) may be coupled with an aryl halide such as A-5 wherein X is bromo or iodo.

5-Aryl-3H-pyrimidin-4-one derivatives can be by condensation of an arylacetonitrile, formamide and ammonia to afford a 4-amino-5-aryl-pyrimidine which can be hydrolyzed to the pyrimidine with aqueous hydrochloric acid. (W. H.

Davies and H. A. Piggott, *J. Chem. Soc.* 1945 347-351) Elaboration of the remaining substituents can then be carried out as described below. Alternatively 2-alkoxy-pyrimidin-5-yl boronic acids or an ester thereof such as B-(4-methoxy-5-pyrimidinyl)-boronic acid (CASRN 909187-37-7) may be coupled with an aryl halide such as A-5 wherein X is bromo or iodo. Substituted pyrimidinyl boronic acids also have been described and are commercially available such as B-(2,4-dimethoxy-5-pyrimidinyl)-boronic acid (CASRN 89641-18-9), 2-chloro-4-(phenylmethoxy)-5-(4,4,5,5-tetramethyl-1,3,2-dioxaborolan-2-yl)-pyrimidine (CASRN 1073354-22-9).

Compounds of formula I wherein A is 2,4-dioxo-1,2,3,4-tetrahydro-pyrimidin-5-yl are prepared using an analogous palladium-catalyzed of an aryl halide (A-5, X is bromo or iodo) utilizing B-(1,2,3,4-tetrahydro-2,4-dioxo-5-pyrimidinyl)-boronic acid (CASRN 70523-22-7). The isomeric 4,6-dioxo-1,4,5,6-tetrahydro-pyrimidin-5-yl moiety was introduced by a palladium-catalyzed coupling of dimethyl malonate to insert the C—C link to the phenyl core and subsequently completing the ring by condensing the diester with acetamidine (see, e.g., example 26).

Compounds of formula I wherein A is 6-oxo-1,6-dihydro-[1,2,4]triazin-5-yl are prepared by introduction of an α-amino-acetic substituent which is subsequently condensed sequentially with dimethoxymethyl-dimethyl-amine and hydrazine to elaborate the 6-oxo-1,6-dihydro-[1,2,4]triazinyl ring.

fords C-2a which can be O-alkylated with iodomethane in the presence of base to afford C-2b which can be further transformed by procedures described previously. 5-Bromo-3-(1-difluoromethyl-cyclopropyl)-2-methoxy-benzaldehyde was prepared from 5-bromo-salicylaldehyde (162a). The phenolic oxygen is protected and the formyl substitutent is converted to a cyano methyl by reduction to the benzyl alcohol, mesylation and displacement of the mesyl group by sodium cyanide. Dialkylation of the methylene with ethylene dibromide introduces the cyclopropyl ring. Conversion of the nitrile to a desired difluoromethyl was accomplished by reduction of the nitrile to the aldehyde and fluorination of the aldehyde with an electrophilic fluorinating agent such as DAST. Sequential formylation and O-alkylation with iodomethane in the presence of base affords 170. In these two examples the stilbene is introduced utilizing a Horner-Wadsworth-Emmons reaction followed by palladium catalyzed coupling to introduce the heteroaryl substituent. 5,7-Diiodo-4-methoxy-3,3-dimethyl-2,3-dihydro-benzofuran is prepared by O-alkylation of 2,6-dibromo-phenol with 3-bromo-2-methyl-propene to afford 148 and subjecting resulting ether to a free-radical cyclization to afford 4-hydroxy-3,3-dimethyl-2,3-dihydro-benzofuran (150). Sequential dihalogentation and O-alkylation of the phenol affords 152b. Sequential palladium-catalyzed coupling 108 and 156 affords compounds of the present invention. 5,7-Dibromo-3,3-dimethyl-

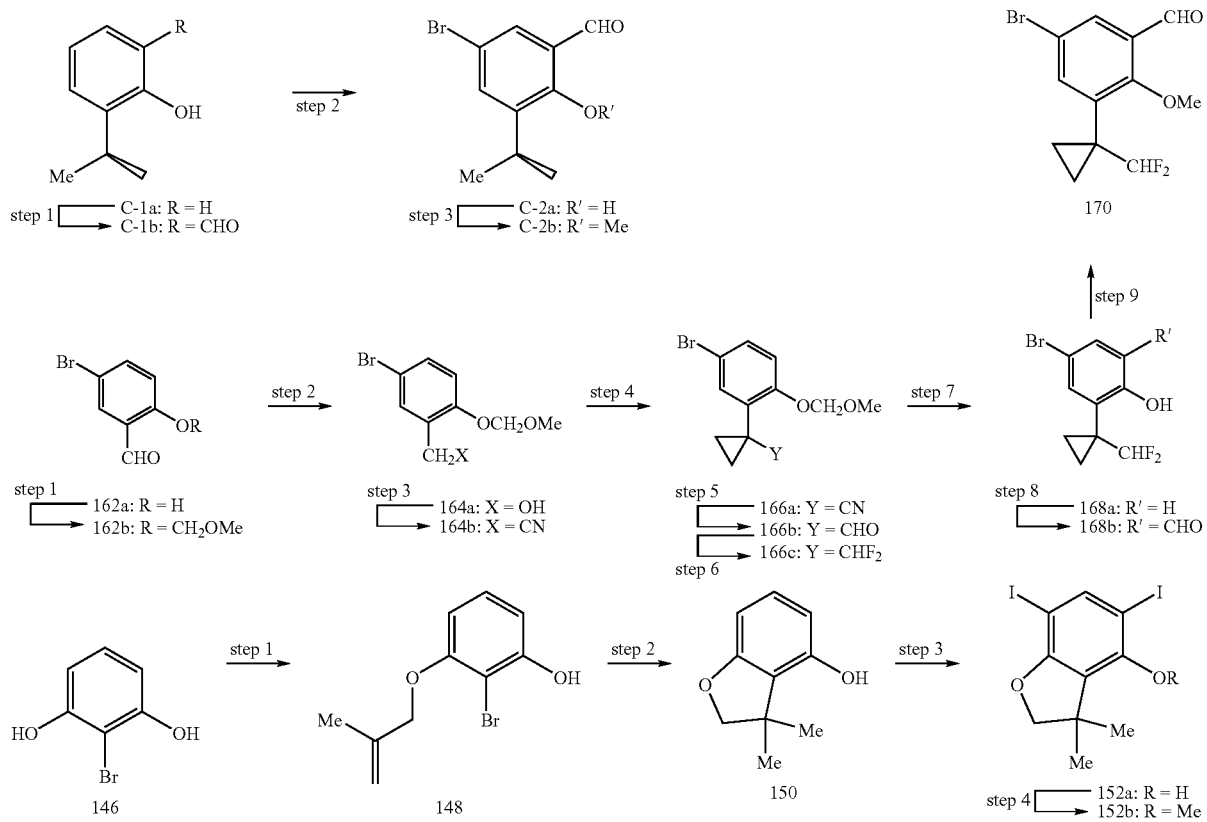

SCHEME C

Compounds of the present invention with a 1-methyl-cyclopropyl substituent were prepared from 2-(1-methyl-cyclopropyl)-phenol (CASRN 4333684-77-6) as depicted in SCHEME C. Sequential formylation and bromination-affords 2,3-dihydro-benzofuran is prepared analogously except 2,6-dibromo-phenol is replaced by 2-bromo-phenol to afford 3,3-dimethyl-2,3-dihydro-benzofuran which subsequently is dihalogenated to produce 102.

Anti-Viral Activity

The activity of the inventive compounds as inhibitors of HCV activity may be measured by any of the suitable methods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 8. Cell-based replicon systems for HCV have been developed, in which the nonstructural proteins stably replicate subgenomic viral RNA in Huh7 cells (V. Lohmann et al., *Science* 1999 285:110 and K. J. Blight et al., *Science* 2000 290:1972. The cell-based replicon assay conditions used for compounds of the present invention are described in Example 4. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system. Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays.

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate. The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

A therapeutically effective amount of a compound of the present invention, and optionally one or more additional antiviral agents, is an amount effective to reduce the viral load or achieve a sustained viral response to therapy. Useful indicators for a sustained response, in addition to the viral load, include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Example 1

N-(4-{(E)-2-[5-tert-Butyl-2-hydroxy-3-(3-oxo-3,4-dihydro-pyrazin-2-yl)-phenyl]-vinyl}-phenyl)-methanesulfonamide (I-6) and N-(4-{2-[5-tert-butyl-2-hydroxy-3-(3-oxo-3,4-dihydro-pyrazin-2-yl)-phenyl]-ethyl}-phenyl)-methanesulfonamide (I-5)

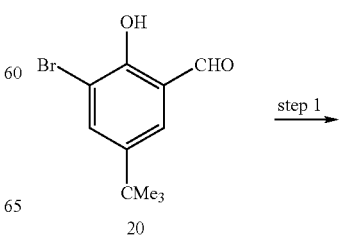

20

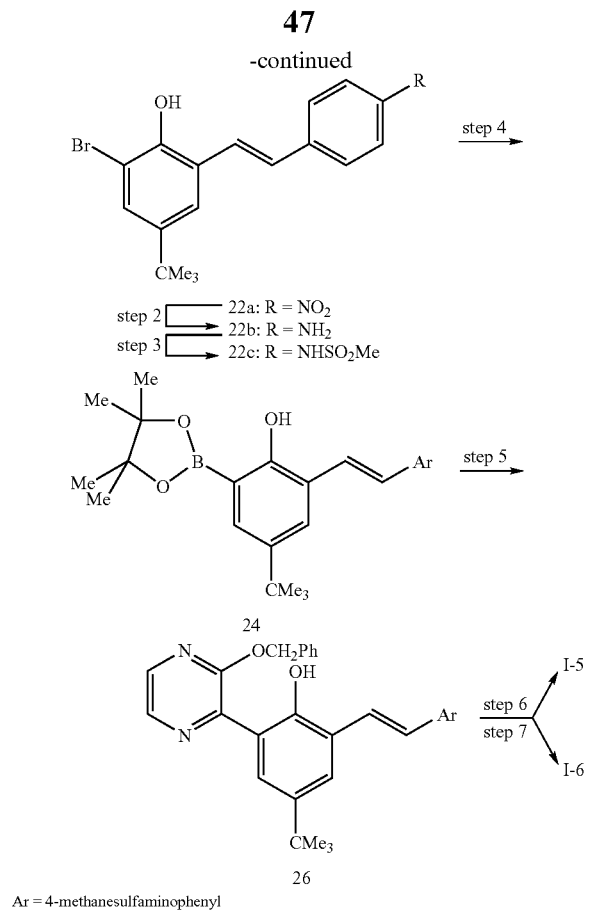

Ar = 4-methanesulfaminophenyl step 1—To a solution of 15-crown-5 (1.72 g) in THF (20 mL) cooled to 0° C. was added NaH (1.56 g, 3.9 mmol, 60% mineral oil dispersion) and a solution of diethyl (4-nitrobenzyl)-phosphonate (10.65 g, 3.9 mmol) and THF (20 mL). After stirring for 10 min at 0° C., a solution of 20 (5.0 g) and THF (30 mL) was added slowly. After an additional 10 min the reaction was warmed to RT then heated at reflux for 6 h. The reaction was cooled to RT, quenched with 1 N HCl and extracted with EtOAc. The combined extracts were dried, filtered and concentrated in vacuo. The crude product was purified by $SiO_2$ chromatography eluting with 5% EtOAc to afford 9.5 g of 22a.

step 2—To a solution of 22a (0.070 g, 0.19 mmol) in EtOAc (40 mL) was added $SnCl_2.2H_2O$ (210 mg). The reaction was heated at reflux for 2 h then cooled and slowly poured into ice-cold aq. $NaHCO_3$. The resulting mixture was extracted with EtOAc and the combined extracts were dried, filtered and evaporated. The crude product was purified by $SiO_2$ chromatography eluting with 15% EtOAc to afford 22b.

step 3—To a solution of 22b (0.042 g, 0.12 mmol) and pyridine (20 mL) cooled to 0° C. was added methanesulfonyl chloride (9.4 µL, 0.12 mmol). After stirring for 40 min at 0° C., the reaction mixture was diluted with EtOAc and the resulting solution was poured into 1 N HCl. The combined organic extracts were dried, filtered and concentrated in vacuo. The crude product was purified by $SiO_2$ chromatography eluting with 25% EtOAc/hexane to afford 22c.

step 4—A mixture of 22c (0.100 g, 0.24 mmol), bis-(pinacolato)diboron (0.0901 g, 0.35 mmol), $PdCl_2(PPh_3)_2$ (0.0135 g) and KOAc (0.070 g) under an Ar atmosphere was dissolved in dioxane (3.0 mL). The reaction mixture was then heated to 110° C. for 3 h, cooled to RT and partitioned between EtOAc and aq. $NH_4Cl$. The aqueous phase was extracted with EtOAc and the combined extracts were dried, filtered and evaporated. The crude product was purified by $SiO_2$ chromatography eluting with 25% EtOAc/hexane to afford 24.

step 5—A tube was charged with 24 (0.055 g, 0.12 mmol), 2-benzyloxy-3-chloro-pyrazine (0.0386 g, 0.017 mmol), $Pd(PPh_3)_4$ (0.0202 g, 0.017 mmol), $Na_2CO_3$ (0.038 g, 0.36 mmol), MeOH (0.3 mL) and DCM (0.9 mL). The tube and solution were sparged with Ar, sealed and heated at 115° C. for 35 min. The solution was cooled, filtered through CELITE, and the filtrate concentrated in vacuo. The crude product was purified by $SiO_2$ chromatography eluting with 20% EtOAc/hexane to afford 26.

step 6—To a solution of 26 (0.034 g, 0.064 mmol) in EtOAc (2 ml)/MeOH (1 mL) was added $Pd(OH)_2$ (0.0135 g) and the resulting mixture stirred overnight under a hydrogen atmosphere (balloon). The reaction mixture was filtered and concentrated. The crude product was purified on a preparative $SiO_2$ TLC plate developed with 50% EtOAc/hexane to afford I-5.

step 7—To a solution of 26 (0.075 g, 0.14 mmol) and HOAc (2.0 mL) at RT was added HBr (47.5 µL). The reaction was sealed and heated to 60° C. for 45 min. The solution was cooled to RT, diluted with EtOAc and poured into satd. $NaHCO_3$. The aqueous layer was extracted with EtOAc and the combined extracts dried, filtered and evaporated. The crude product was purified by $SiO_2$ chromatography eluting with 5% MeOH/DCM to afford I-6.

Example 2

N-(4-{2-[3-tert-Butyl-2-methoxy-5-(3-oxo-3,4-dihydro-pyrazin-2-yl)-phenyl]-ethyl}-phenyl)-methanesulfonamide (I-1) and N-(4-{2-[3-tert-Butyl-2-methoxy-5-(3-oxo-3,4-dihydro-pyrazin-2-yl)-phenyl]-ethyl}-phenyl)-acetamide (I-2)

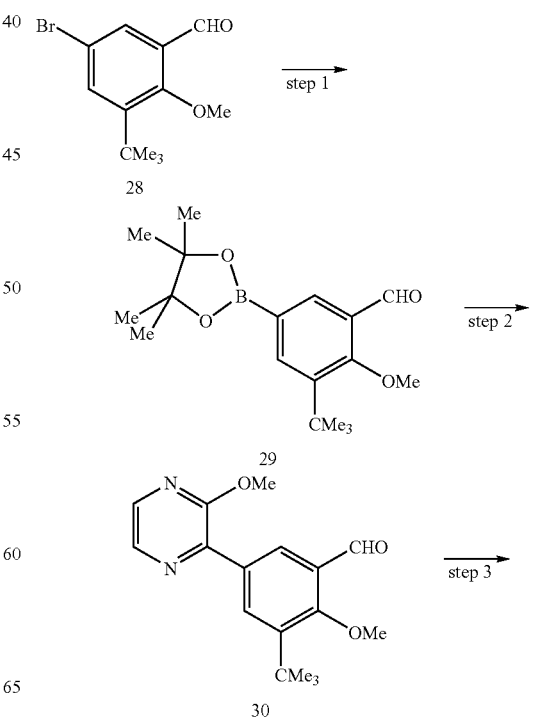

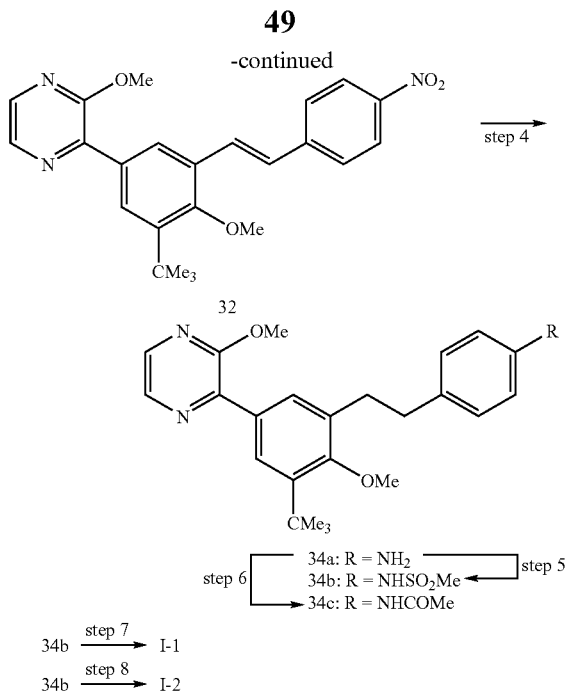

5-bromo-3-tert-butyl-2-methoxybenzaldehyde (28)—To a solution of 3-tert-butyl-2-hydroxybenzaldehyde (CASRN 24623-65-2, 5.00 g) DCM (20 mL) at 0° C. was added dropwise a solution of $Br_2$ (1.45 mL) in DCM (15 mL) over a period of 30 min. After the addition was complete the reaction was stirred for 1 h before the organic volatiles were removed under reduced pressure to afford 7.23 g of 5-bromo-3-tert-butyl-2-hydroxybenzaldehyde (27) as a light yellowish solid.

A mixture of 27 (3.83 g), MeI (2.32 mL) and $K_2CO_3$ (6.18 g) in DMF (50 mL) was heated at 50° C. for 1 h then cooled to RT and diluted with ether and water. The organic layer was thrice washed with water then brine, dried ($MgSO_4$) and concentrated to afford 3.99 g of 5-bromo-3-tert-butyl-2-methoxybenzaldehyde (28) as a yellow solid.

step 1—A mixture 28 (0.60 g CASRN 417715-878), bis-(pinacolato)diboron (31, 0.69 g), Pd(dppf)$_2$Cl$_2$ (54 mg) and KOAc (542 mg) in DME (30 mL) under an argon atmosphere was heated at 70° C. for 14 h and then at 90° C. for additional 7 h. The reaction was cooled to RT, and diluted with water and ether. The organic layer was washed with brine, dried ($MgSO_4$), filtered and concentrated. The crude residue was purified by $SiO_2$ chromatography eluting with a EtOAc/hexane gradient (0 to 12% EtOAc) to afford 478 mg of 29 contaminated with a small amount of 31.

step 2—A vial was charged with 29 (0.365 g 1.48 mmol), 2-chloro-3-methoxy-pyrazine (0.198 g, 1.370 mmol), Pd(Ph$_3$)$_4$ (0.106 g, 0.092 mmol) Na$_2$CO$_3$ (0.313 g, 2.953 mmol), MeOH (6 mL) and DCM (2 mL), sealed and irradiated in a microwave synthesizer at 115° C. for 30 min. The reaction mixture was cooled to RT, diluted with EtOAc, washed with brine, dried (Na$_2$SO$_4$), filtered and concentrated in vacuo. The crude product was purified by SiO$_2$ chromatography eluting with a EtOAc/hexane gradient (2 to 10% EtOAc) to afford 0.275 g of 30.

step 3—To a solution of 4-nitro-benzylphosphonium bromide (1.23 g, 2.573 mmol) and DMF (10 mL) cooled to 0° C. was added NaH (0.211 g, 5.275 mmol, 60% mineral oil dispersion). The solution was stirred for 30 min then a solution of 30 (0.251 g, 0.857 mmol) and DMF (5 mL) was added and the resulting solution stirred overnight at RT. The reaction was quenched by addition of 1N HCl (8 mL) and the resulting solution diluted with EtOAc. The EtOAc solution was separated and twice washed with brine, dried (Na$_2$SO$_4$), filtered and concentrated in vacuo. The crude product was purified by SiO$_2$ chromatography eluting with a EtOAc/hexane gradient (5 to 10% EtOAc) to afford 317 mg of 32.

step 4—A stream of hydrogen was bubbled through a mixture of 32 (0.317 g, 0.757 mmol), Pd(OH)$_2$ (0.109 g), EtOAc (15 mL) and MeOH (15 mL). After 30 min no starting material remained and the resulting solution was filtered to remove the catalyst and evaporated. The crude product was purified by SiO$_2$ chromatography eluting with a EtOAc/hexane gradient (15 to 30% EtOAc) to afford 0.210 g (71%) of 34a.

step 5—To a solution of 34a (0.0786 g, 0.201 mmol) in dry pyridine cooled to 0° C. was added mesyl chloride (20 μL, 0.257 mmol) and the resulting solution stirred at RT overnight. The solution was diluted with EtOAc, sequentially washed with aqueous CuSO$_4$, 1N HCl, dried (Na$_2$SO$_4$), filtered and evaporated to afford 0.102 g of crude product. The crude product was purified by SiO$_2$ chromatography eluting with a EtOAc/hexane gradient (5 to 30% EtOAc) to afford 0.081 g of 34b.

step 7—A vial was charged with 34b (0.081 g, 0.173 mmol), HBr (35 μL) and HOAc (4 mL), sealed and irradiated in a microwave synthesizer at 60° C. The solution was cooled to RT and poured into ice and aqueous NaHCO$_3$. The resulting mixture was extracted with EtOAc, dried (Na$_2$SO$_4$), filtered and evaporated. Residual HOAc was removed by azeotropic distillation with benzene to afford 0.0595 g of I-1.

step 6—To a solution of 34a (0.0768 g, 0.196 mmol) in dry pyridine cooled to 0° C. was added acetic anhydride (25 μL, 0.264 mmol) and the resulting solution stirred overnight at RT. The resulting solution was diluted with EtOAc and sequentially washed with aqueous CuSO$_4$ and 1N HCl, dried (Na$_2$SO$_4$), filtered and evaporated. The crude product was purified by SiO$_2$ chromatography eluting with a EtOAc/hexane gradient (25 to 50% EtOAc) to afford 0.074 g of 34c.

step 8—A tube was charged with 34c (0.074 g), HBr (75 μL) and HOAc (4 mL), sealed and heated at 60° C. overnight. The solution was cooled and poured into ice and aqueous NaHCO$_3$, extracted with EtOAc, dried (Na$_2$SO$_4$), filtered and concentrated in vacuo. The resulting solid was dried by azeotropic distillation with benzene then dried in vacuo to afford 0.040 g of I-2.

Example 3

N-[3-tert-Butyl-2-methoxy-5-(3-oxo-3,4-dihydro-pyrazin-2-yl)-phenyl]-4-methanesulfonylamino-benzamide (I-4)

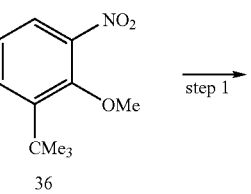

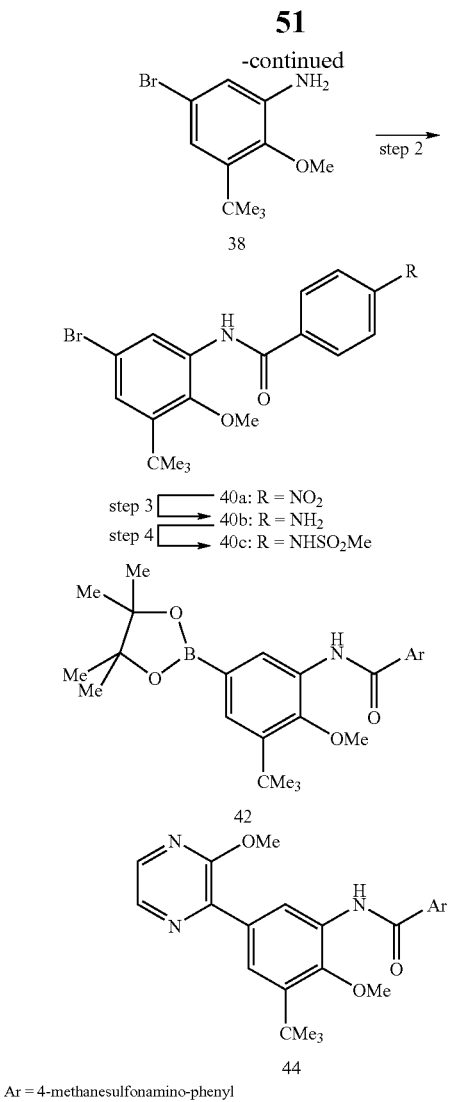

Ar = 4-methanesulfonamino-phenyl step 1—To a solution of 36 (0.41 g, 0.423 mmol, CASRN 474554-50-2) in MeOH (4 mL) and H₂O (4 mL) was added sequentially NH₄Cl (0.76 g, 14.23 mmol) and Fe (0.38 g, 6.83 mmol;) and the resulting mixture heated at reflux for 1 h. The solution was cooled and filtered through a CELITE pad which was washed with MeOH. The filtrate was concentrated in vacuo and the resulting mixture extracted with EtOAc. The extract was washed with brine, dried (Na₂SO₄), filtered and concentrated in vacuo. The crude product was purified by SiO₂ chromatography eluting with an EtOAc/hexane gradient (0 to 20% EtOAc) to afford 0.235 g (64%) of 38.

Acylation of 38 (step 2) with 4-nitro-benzoic acid is carried out with EDCI, HOBt DIPEA in DMF. Reduction of the nitro group (step 3) to afford 40a is carried out with Fe in accord with the procedure in step 1 of the current example. Sulfonylation (step 4) of 40b is carried out as described in step 3 of example 1.

step 5—A flask was charged with 40c (0.15 g, 0.329 mmol), bis-(pinacolato)diboron (0.091 g, 0.36 mmol), KOAc (0.096 g, 0.988 mmol), PdCl₂(PPh₃)₄ (0.015 g) and dioxane (6 mL) and the resulting mixture heated at reflux for 2 h. The solution was cooled to RT and partitioned between H₂O and EtOAc. The organic extract was washed with brine, dried (Na₂SO₄), filtered and evaporated. The crude boronate ester was purified by SiO₂ chromatography eluting with EtOAc/hexane to afford 0.16 g of 42.

step 6—A flask was charged with 42 (0.167 g, 0.332 mmol), 2-chloro-3-methoxy-pyrazine (0.043 g, 0.329 mmol), Na₂CO₃ (0.32 g, 0.997 mmol), Pd(Ph₃)₄ (0.038 g) and DCM/MeOH (3:1) and the resulting solution heated to 110° C. for 30 min. The solution was cooled to RT, filtered and the crude product purified by SiO₂ chromatography to afford 42.

step 7—To a solution 42 (0.090 g) and HOAc (2 mL) was added HBr (63 μL) and the resulting solution was heated to 60° C. overnight. The temperature was elevated to 90° C. for another 24 h, cooled and the resulting solid collected by filtration. The crude product was purified by SiO₂ chromatography to afford 0.010 g of I-4.

Example 4

N-(4-{2-[3-tert-Butyl-4-fluoro-2-methoxy-5-(3-oxo-3,4-dihydro-pyrazin-2-yl)-phenyl]-ethyl}-phenyl)-methanesulfonamide (I-3)

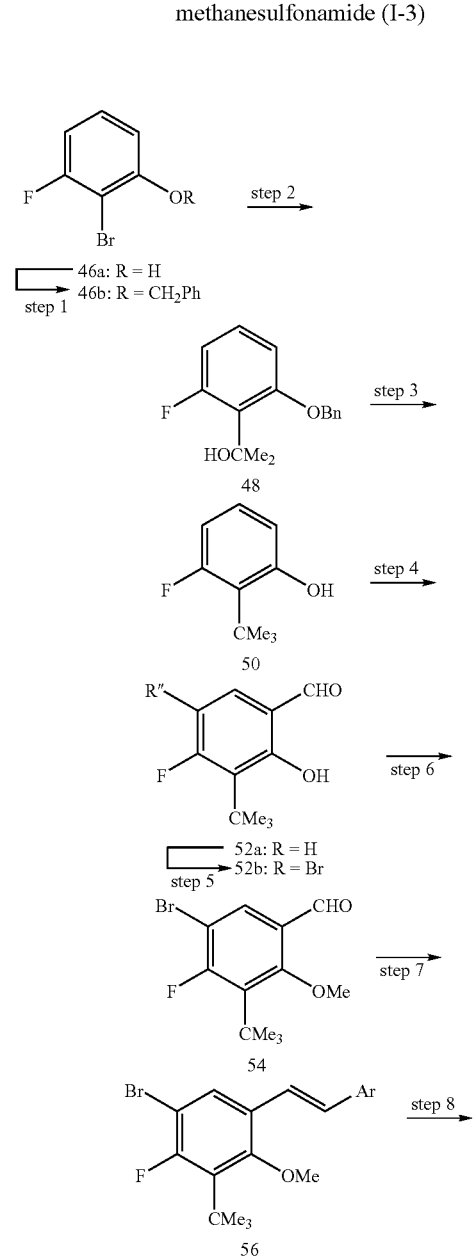

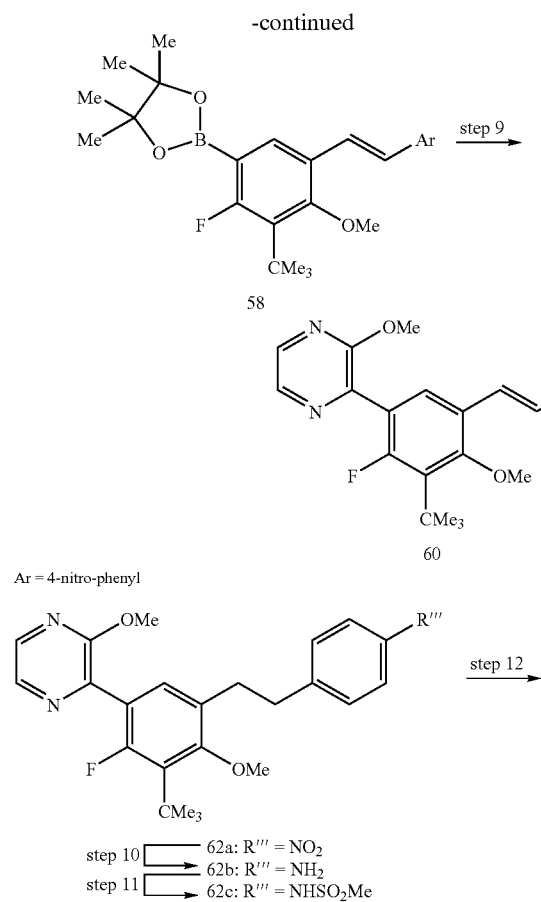

Ar = 4-nitro-phenyl step 10: 62a: R''' = NO₂
step 11: 62b: R''' = NH₂
       62c: R''' = NHSO₂Me step 1—To a solution of 46a (4.0 g, 21 mmol), and benzyl bromide (3.50 mL, 29 mmol) and acetone (100 mL) was added K₂CO₃ (7.236 g, 52 mmol) and the resulting reaction mixture stirred at reflux overnight. The reaction was cooled to RT and the acetone evaporated. The residue was partitioned between EtOAc (200 mL) and H₂O (50 mL). The aqueous layer was extracted with EtOAc and the combined organic extracts were washed sequentially with H₂O (50 mL) and brine (50 mL). The EtOAc solution was dried (Na₂SO₄), filtered and evaporated. The residue was purified by SiO₂ chromatography eluting with a EtOAc/hexane gradient (0 to 10% EtOAc) to afford 5.76 (98%) of 46b.

step 2—A round-bottom flask was charged with 46b (53.865 g, 20 mmol) and dry THF (24 mL). The solution was cooled to −78° C. and a solution of n-butyl lithium/hexane (9.50 mL, 24 mmol, 2.5 M solution in hexanes) was added dropwise and the resulting solution stirred at −78° C. for 1 h. Acetone (1.9 mL, 26 mmol) was added dropwise and the resulting mixture stirred at −78° C. for an additional 15 min. The cooling bath was removed and the reaction stirred at RT for 1 h. The reaction mixture was cooled to 0° C. and quenched by addition of H₂O (30 mL) and the resulting solution extracted with EtOAc (150 mL). The aqueous phase was again extracted with EtOAc (150 mL) and the combined extracts washed sequentially with H₂O and brine. The organic phase was dried (Na₂SO₄), filtered and evaporated. The residue was purified by SiO₂ chromatography eluting with a EtOAc/hexane gradient (0 to 15% EtOAc) to afford 3.70 (72%) of 48.

step 3—To a solution of 48 (3.710 g. 14 mmol) and DCM (3.0 mL) was cooled to −78° C. and Ti(IV) Cl₄ (3.13 mL, 29 mmol) was added dropwise. The reaction was stirred at −78° C. for 1.5 h, then a solution of Me₂Zn and hexane (57 mL, 57 mmol, 1.0M in heptane) was added. After the addition was complete the reaction was warmed to RT and stirred for 3.5 h. The reaction mixture was poured into a mixture of ice and H₂O and the resulting mixture stirred for 30 min. The aqueous phase was extracted with DCM and the resulting extract washed with brine. The aqueous phase was twice extracted with DCM. The combined organic solutions were dried (Na₂SO₄), filtered and evaporated. The resulting product was purified by SiO₂ chromatography eluting with a EtOAc/hexane gradient (0 to 30% EtOAc) which afforded 0.5670 g of 50 and 6-benzyl-2-tert-butyl-3-fluorophenol.

step 4—To a solution of 50 (0.400 g, 2 mmol) and MeCN (5 mL) was added paraformaldehyde (0.409 g (14 mmol), MgCl₂ (0.289 g, 3 mmol) and TEA (1.05 mL, 8 mmol) and the resulting suspension was stirred at reflux overnight. The reaction mixture was cooled to RT and partitioned between DCM (100 mL) and 1M HCl (20 mL). The aqueous phase was extracted with DCM and the combined DCM solutions were dried (Na₂SO₄), filtered and concentrated in vacuo. The crude product was purified by SiO₂ chromatography eluting with a EtOAc/hexane gradient (0 to 5% EtOAc) to afford 0.274 g (62%) of 52a.

step 5—To a solution of 52a (0.270 g, 1 mmol) DCM (7.5 mL) and MeOH (5 mL) was added tetrabutylammonium tribromide (0.627 g, 1.05 mmol) and the resulting solution stirred at RT for 3.5 h. The reaction mixture was concentrated and the residue partitioned between EtOAc (100 mL) and H₂O (20 mL). The aqueous layer was extracted with EtOAc (100 mL) and each organic extract was sequentially washed with H₂O (20 mL) and brine (20 mL). The organic extracts were combined, dried (Na₂SO₄), filtered and evaporated. The residue was purified by SiO₂ chromatography eluting with an EtOAc/hexane gradient (0 to 5% EtOAc) to afford 0.120 g (35%) of 52b.

step 6—To a solution of 52b (0.117 g) in DMF (2 mL) was added K₂CO₃ (0.147 g) and methyl iodide (40 µL) and the resulting suspension stirred at 60° C. for 2 h. The reaction was cooled to RT and quenched with H₂O. The resulting solution was partitioned between Et₂O (50 mL) and H₂O (10 mL). The aqueous layer was extracted with Et₂O. The organic solutions were washed sequentially with H₂O (2×5 mL) and brine, combined, dried (Na₂SO₄), filtered and evaporated to afford 0.117 g of 54 which was sufficiently pure to use directly in the next step.

step 7—To a mixture of NaH (0.024 g, 60% mineral oil dispersion) and THF (1.0 mL) cooled to 0° C. was added 15-crown-5 (0.006 g) and the resulting solution stirred for 5 min. To this mixture was added dropwise a solution of diethyl (4-nitrobenzyl)phosphonate (0.121 g, 1.1 equivalent) and THF (1.0 mL). The resulting reaction mixture was stirred for 5 min after the addition was complete then a solution of 54 (0.116 g. 1.0 equivalent) and THF (3.0 mL) was added dropwise over 10 min while the reaction temperature was maintained at 0° C. The reaction was stirred at 0° C. for 15 min followed by 1.5 h at RT. The reaction was quenched by careful addition of water. The resulting solution was partitioned between EtOAc (50 mL) and H₂O (10 mL) and the aqueous layer was withdrawn and extracted with EtOAc (50 mL). The two organic solutions were separately washed sequentially with water and brine, combined, dried (Na₂SO₄), filtered and evaporated. The crude product was purified by SiO₂ chromatography eluting with an EtOAc/hexane gradient (0 to 10% EtOAc) to afford 0.155 g (94%) of 56.

step 8—A flask was charged with 56 (0.100 g), bis(pinacolato)diboron (0.068 g), PdCl₂(PPh₃)₂ (0.010 g), KOAc (0.072 g) and dioxane (3.0 mL) and stirred at 90° C. overnight. The reaction was cooled to RT and partitioned between EtOAc (50 mL) and H₂O (10 mL) and the organic phase sequentially washed with H₂O and brine. The aqueous layer was re-extracted with EtOAc (50 mL) and the extracts were sequentially washed with H₂O and brine. The combined organic extracts were dried (Na₂SO₄), filtered and concentrated in vacuo. The crude product was purified by SiO₂ chromatography eluting with an EtOAc/hexane gradient (0 to 70% EtOAc) to afford 0.042 g (32%) of 58.

step 9—A microwave tube was charged with 58 (0.042 g), 2-chloro-3-methoxy-pyrazine (0.015 g), Pd(PPh₃)₄ (0.009 g), Na₂CO₃ (0.025 g), MeOH (1.2 mL) and DCM (0.4 mL), sealed and irradiated in a microwave synthesizer at 115° C. for 30 min. The reaction was cooled and concentrated. The residue was partitioned between EtOAc (30 mL) and H₂O. The aqueous layer was withdrawn and re-extracted with EtOAc (30 mL). The extracts were sequentially washed with H₂O and brine. The combined organic extracts were dried (Na₂SO₄), filtered and concentrated in vacuo. The crude product was purified by SiO₂ chromatography eluting with an EtOAc/hexane gradient (0 to 20% EtOAc) to afford 0.02 g (52%) of 60.

Conversion of 60 to I-3 is carried out in accord with the procedures described in steps 4, 5 and 7 of example 2.

Example 5

N-(4-{(E)-2-[3-tert-Butyl-2-methoxy-5-(3-oxo-2,3-dihydro-pyridazin-4-yl)-phenyl]-vinyl}-phenyl)-methanesulfonamide (I-13)

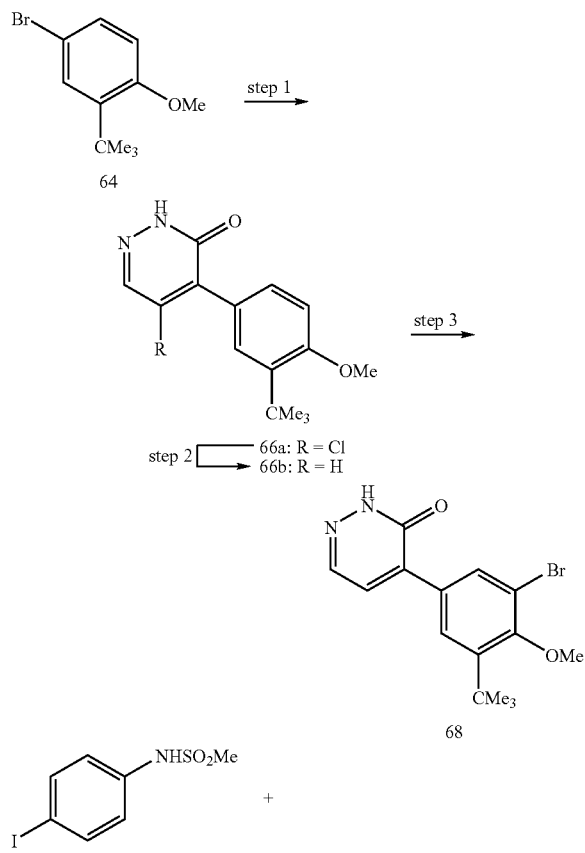

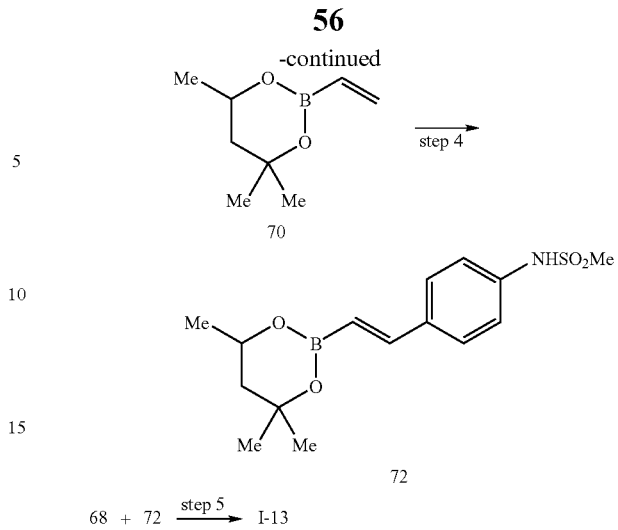

step 1—A dry round-bottom flask was charged with 4-bromo-2-tert-butylanisole (2.933 g, 0.005 mmol, CASRN 14804-34-3), THF (15 mL) and magnesium turnings (0.2 g) were added. The reaction mixture was heated to reflux and stirred for 45 min then cooled to RT. The resulting solution was added dropwise at RT to a stirred solution of 4,5-dichloro-3-hydroxy-pyridazine (0.796 g, CASRN 932-22-9), THF (10 mL) and Et₂O (20 mL). The reaction mixture was then heated at reflux overnight. The reaction was cooled to 0° C. and quenched with sat'd NH₄Cl and extracted with EtOAc (150 mL). The aqueous phase was withdrawn and re-extracted with EtOAc (150 mL). Each extract was washed sequentially with water and brine. The combined organic extracts were dried (Na₂SO₄), filtered and concentrated in vacuo. The residue was triturated with EtOAc/hexane (1:1) to afford 1.0870 g (77%) of 66a.

step 2—A Parr Shaker bottle was charged with 66a (1.080 g), a solution of KOH (0.517 g) and H₂O (11 mL) and DMF (1.3 mL). To this mixture was added 10% Pd/C and the bottle was connected to a Parr shaker and flushed three times with hydrogen then shaken overnight at RT under an atmosphere of ca. 50 psi of hydrogen. To the resulting solution was added 5M KOH to dissolve the precipitate then the solution was filtered through a glass microfiber filter and rinsed with 5M KOH and H₂O. The filtrate was acidified with con HCl and the resulting mixture extracted with DCM (100 mL). The aqueous layer was withdrawn and re-extracted with EtOAc. The combined extracts were dried (Na₂SO₄), filtered and evaporated to afford 0.791 g (83%) of 66b.

step 3—To a solution of 66b (0.100 g) and DMF (2 mL) was added NBS (0.069 g) and the resulting solution stirred art 50° C. overnight. The reaction was concentrated in vacuo and the residue partitioned between Et₂O and H₂O. The aqueous layer was withdrawn and re-extracted with Et₂O. The organic layers were twice washed with H₂O (5 mL) and once with brine (5 mL). The organic layers were combined, dried (Na₂SO₄), filtered and evaporated. The crude product was purified by SiO₂ chromatography eluting with an EtOAc/hexane gradient (0 to 30% EtOAc) to afford 0.068 g (52%) yield of 68.

step 4—To a solution of Pd(OAc)₂ (0.076 g) and tris-(ortho-tolyl)-phosphine (0.246 g, 1 mmol) and toluene (16 mL) were added sequentially N-(4-iodo-phenyl)-methanesulfonamide (2.00 g, 7 mmol, CASRN 102294-59-7), tributyl amine (1.92 mL) and 4,4,6-trimethyl-2-vinyl-[1,3,2]dioxaborinane (1.244 g, 8 mmol, 70) and the reaction was heated at reflux for 72 h. The reaction was cooled to RT and partitioned between Et$_2$O (100 mL) and 1M HCl (20 mL). The aqueous layer was withdrawn and re-extracted with Et$_2$O. The organic phases were washed sequentially with H$_2$O and brine. The extracts were combined, dried (Na$_2$SO$_4$), filtered and evaporated. The residue was purified by SiO$_2$ chromatography eluting with an EtOAc/hexane gradient (0 to 30% EtOAc) to afford 1.4 g (58%) of 72.

step 5—A microwave tube was charged with 68 (0.068 g), 72 (0.078 g), Na$_2$CO$_3$ (0.064 g), Pd(PPh$_3$)$_4$ (0.023 g), MeOH (1.8 mL) and DCM (0.6 mL). The tube was flushed with argon, sealed and irradiated in a microwave synthesizer at 125° C. for 40 min. The reaction mixture was cooled and concentrated in vacuo. The residue was partitioned between DCM (25 mL) and H$_2$O (5 mL). The organic layer was washed with brine (5 mL). The aqueous phase was twice extracted with DCM (25 mL). The organic layers were combined, dried (Na$_2$SO$_4$), filtered and evaporated. The crude product was purified by SiO$_2$ chromatography eluting with a EtOAc/hexane gradient (0 to 60% EtOAc) to afford 0.175 g (18%) of I-13.

I-12 can be prepared in accord with the procedures in step 1 and 2 by coupling of 4,5-dichloro-3-hydroxy-pyridazine and 3-bromo-5-tert-butyl-toluene. I-16 can be prepared in accord with the procedures in step 1 and 2 by coupling of 4,5-dichloro-3-hydroxy-pyridazine and 4-bromo-2-tert-butyl-anisole.

Example 6

N-(4-{(E)-2-[5-(2,4-Dioxo-1,2,3,4-tetrahydro-pyrimidin-5-yl)-2-methoxy-3-trifluoromethyl-phenyl]-vinyl}-phenyl)-methanesulfonamide (I-35)

The title compound was prepared in accord with the sequence described in Example 31 except the starting material was 2-trifluoromethyl-phenol (CASRN 444-30-4). Bromination of 2-hydroxy-3-trifluoromethyl-benzaldehyde (244) was accomplished by stirring 244 with NBS in MeCN at RT. Reduction of the nitro group and sulfonylation of the amine to afford N-{4-[(E)-2-(5-bromo-2-methoxy-3-trifluoromethyl-phenyl)-vinyl]-phenyl}-methanesulfonamide (246) which was subjected to palladium-catalyzed coupling of with 137 to afford I-35.

Example 7

N-(4-{(E)-2-[3-tert-Butyl-2-methoxy-5-(3-oxo-3,4-dihydro-pyrazin-2-yl)-phenyl]-vinyl}-phenyl)-methanesulfonamide (I-11)

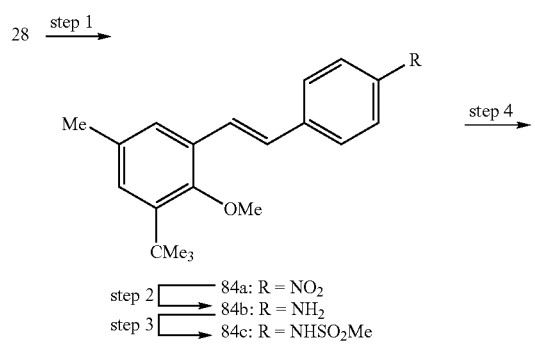

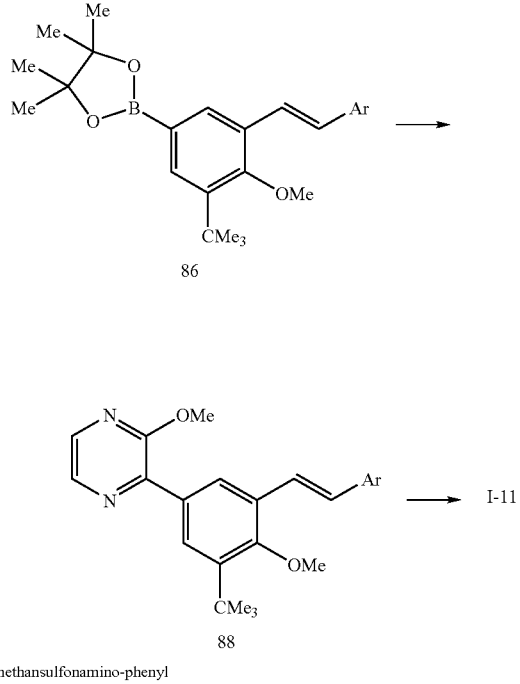

Ar = 4-methansulfonamino-phenyl

The conversion of aldehyde 28 to the stilbene 84a can be carried out by Wadsworth-Horner-Emmons condensation with diethyl (4-nitrobenzyl)-phosphonate as described in step 1 of example 1 step 2—A mixture of 84a (788.3 g, 2.02 mmol), iron (471.2 mg, 8.43 mmol) and NH$_4$Cl (866.7 mg, 16.2 mmol) in MeOH (35 mL) and H$_2$O (30 mL) was heated at reflux for 4 h. The reaction mixture was cooled to RT and filtered. The filtrate was thrice extracted with EtOAc and the combined extracts washed with brine, dried (Na$_2$SO$_4$), filtered and concentrated in vacuo to afford 709 mg (95%) of 84b as a yellow solid.

The remaining steps sulfonylation of the amine (step 3), introduction of the pinacolborane (step 4), Suzuki coupling with 2-chloro-3-methoxy-pyrazine (step 5) and cleavage of the pyrazine ether (step 6) can be carried out according to the procedures in step 3, 4, and 5 of example 1 and step 8 of example 2 respectively.

I-10 can be prepared analogously except in step 1, 28 is replaced with 3-bromo-5-tert-butyl-benzaldehyde [CASRN 241155-25-1].

Example 8

N-(4-{(E)-2-[3-tert-Butyl-5-(5-chloro-3-oxo-2,3-dihydro-pyridazin-4-yl)-phenyl]-vinyl}-phenyl)-methanesulfonamide (I-18)

64 +

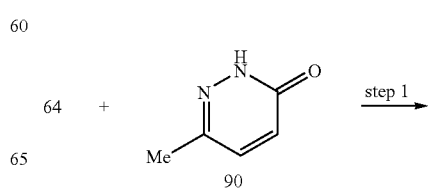

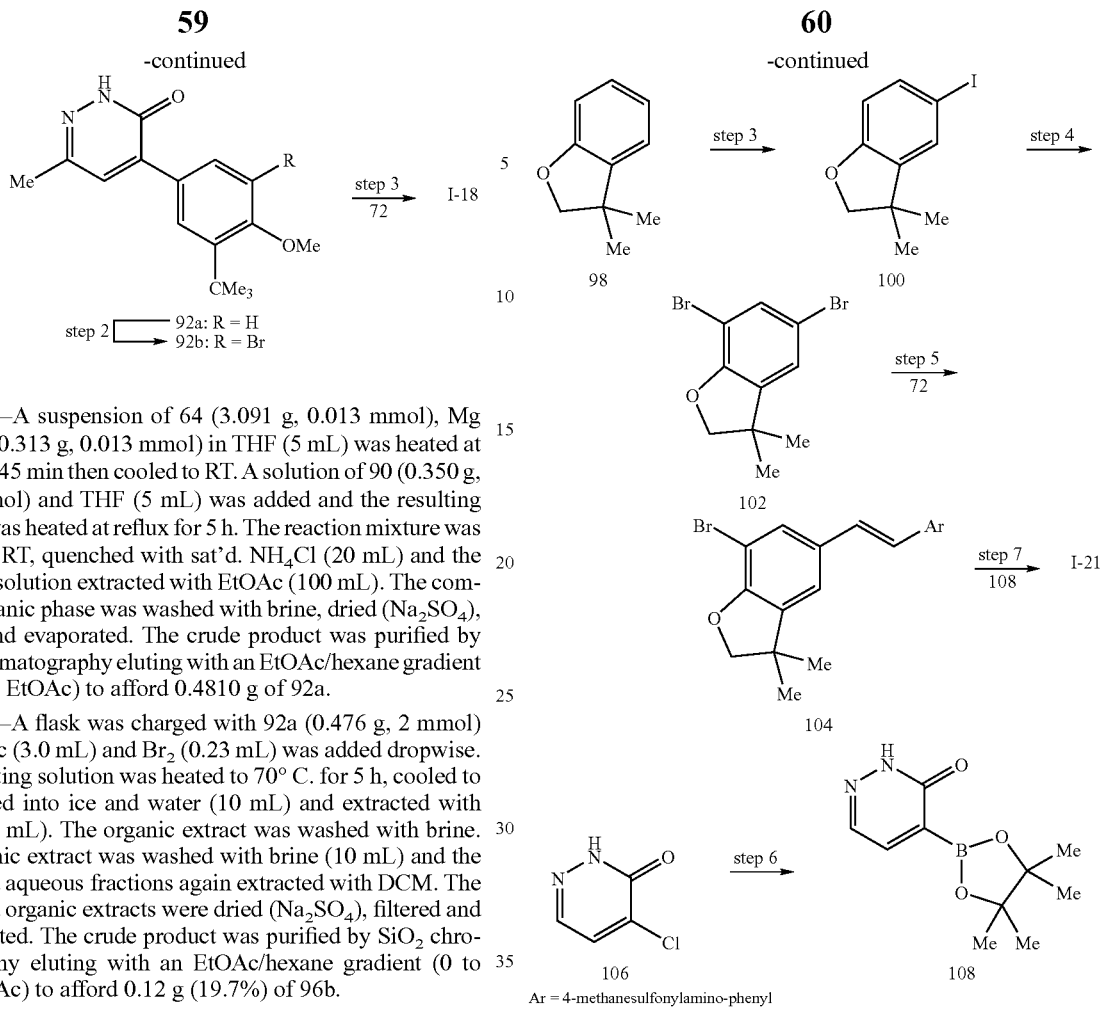

step 1—A suspension of 64 (3.091 g, 0.013 mmol), Mg turnings (0.313 g, 0.013 mmol) in THF (5 mL) was heated at reflux for 45 min then cooled to RT. A solution of 90 (0.350 g, 0.003 mmol) and THF (5 mL) was added and the resulting mixture was heated at reflux for 5 h. The reaction mixture was cooled to RT, quenched with sat'd. NH$_4$Cl (20 mL) and the resulting solution extracted with EtOAc (100 mL). The combined organic phase was washed with brine, dried (Na$_2$SO$_4$), filtered and evaporated. The crude product was purified by SiO$_2$ chromatography eluting with an EtOAc/hexane gradient (0 to 50% EtOAc) to afford 0.4810 g of 92a.

step 2—A flask was charged with 92a (0.476 g, 2 mmol) and HOAc (3.0 mL) and Br$_2$ (0.23 mL) was added dropwise. The resulting solution was heated to 70° C. for 5 h, cooled to RT, poured into ice and water (10 mL) and extracted with DCM (10 mL). The organic extract was washed with brine. The organic extract was washed with brine (10 mL) and the combined aqueous fractions again extracted with DCM. The combined organic extracts were dried (Na$_2$SO$_4$), filtered and concentrated. The crude product was purified by SiO$_2$ chromatography eluting with an EtOAc/hexane gradient (0 to 60% EtOAc) to afford 0.12 g (19.7%) of 96b.

Step 3 was carried out in accord with step 5 of example 5 to afford I-18. The crude product was purified by SiO$_2$ chromatography eluting with an EtOAc/hexane gradient (0 to 60% EtOAc).

Example 9

N-(4-{(E)-2-[3,3-Dimethyl-7-(3-oxo-2,3-dihydro-pyridazin-4-yl)-2,3-dihydro-benzofuran-5-yl]-vinyl}-phenyl)-methanesulfonamide (I-21)

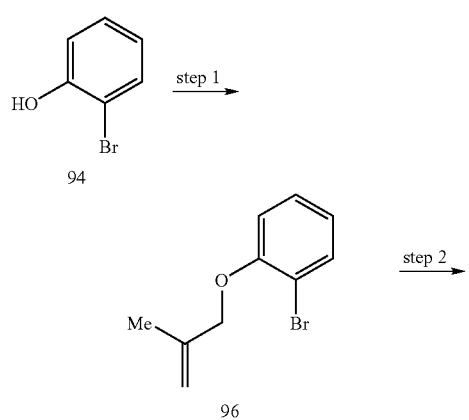

step 1—To a solution of 94 (2.457 g, 14 mmol) and acetone (75 mL) was added K$_2$CO$_3$ (4.907 g, 36 mmol) and 3-bromo-2-methyl propene (2.0 mL, 20 mmol) and the resulting solution was heated at reflux overnight. The reaction mixture was cooled and concentrated in vacuo. The residue was partitioned between EtOAc (150 mL) and H$_2$O (40 mL). The aqueous phase was extracted with EtOAc and the combined organic extracts were sequentially washed with H$_2$O and brine, dried (Na$_2$SO$_4$), filtered and concentrated in vacuo. The residue was purified by SiO$_2$ chromatography eluting with a EtOAc/hexane gradient (0 to 5% EtOAc) to afford 3.34 g (98.5%) of 96.

step 2—To a solution of 96 (3.33 g, 15 mmol) and benzene (150 mL) in a dried flask was added sequentially Bu$_3$SnH (6.625 g, 22 mmol) and AIBN (0.241 g) and the resulting solution heated at reflux overnight. The reaction mixture was cooled to RT, a 10% KF solution was added and the resulting two-phase mixture stirred vigorously for 2 h. The phases were separated and the organic phase was sequentially washed with sat'd. NaHCO$_3$ (50 mL) and brine. The combined organic extracts were dried (Na$_2$SO$_4$), filtered and evaporated. The crude product was purified by SiO$_2$ chromatography eluting with a DCM/hexane gradient (0 to 10% DCM) to afford 1.855 g (85%) of 98.

step 3—To a solution of iodine (2.055 g, 8 mmol) and EtOH (30 mL) was added a solution of silver sulfate (2.525 g, 8 mmol) and a solution of 98 (1.200 g, 8 mmol) in EtOH (10 mL). The brown solution was stirred for 2.5 h at RT. The resulting suspension was filtered through CELITE, the pad rinsed with EtOH and the filtrate concentrated. The crude product was purified by $SiO_2$ chromatography eluting with a DCM/hexane gradient (0 to 10% DCM) to afford 2.001 g (90.5%) of 100.

step 4—To a solution of 100 (2.00 g, 7 mmol) and HOAc (18 mL) in a dried flask was cooled to 0° C. and $Br_2$ was added dropwise over 10 min. The reaction was stirred at RT overnight. Excess bromine was quenched with 10% aq. $Na_2S_2O_3$ (20 mL) and the HOAc was evaporated. The residue was extracted with $Et_2O$ and the organic extract washed with sat'd. $NaHCO_3$. The aqueous phase was back-extracted with $Et_2O$ and the combined extracts washed sequentially with $NaHCO_3$ (2×20 mL), $H_2O$ and brine, dried ($Na_2SO_4$), filtered and concentrated. The residue was purified by $SiO_2$ chromatography eluting with a DCM/hexane gradient (0 to 10% DCM) to afford 1.5960 g (71.5%) of 102.

step 5—A microwave vial was charged with 72 (0.750 g, 2 mmol, assay 95%), 102 (0.708 g, 2 mmol), $K_3PO_4$ (1.404 g, 7 mmol) and $Pd(PPh_3)_4$ (0.127 g, 0.11 mmol) and the tube was evacuated and back-filled with Ar and closed. To the vial was added DMF (10 mL) and the reaction mixture stirred at 80° C. overnight. The reaction mixture was cooled to RT and partitioned between $Et_2O$ (120 mL) and $H_2O$ (20 mL). The aqueous phase was separated and extracted with $Et_2O$. The combined organic extracts were sequentially washed with $H_2O$ (2×20 mL) and brine, dried ($Na_2SO_4$), filtered and concentrated in vacuo. The product was purified by $SiO_2$ chromatography eluting with an EtOAc/hexane gradient (0 to 30% EtOAc) to afford 0.4260 g (45.8%) of 104.

step 7—A microwave vial was charged with 104 (0.120 g, 0.28 mmol), 108 (0.069 g, 0.31 mmol), $Pd(PPh_3)_4$ (0.033 g, 0.028 mmol), $Na_2CO_3$ (0.090 g, 1 mmol), MeOH (3 mL) and DCM (1 mL), flushed with Ar and sealed. The vial was irradiated in a microwave synthesizer for at 115° C. for 30 min. The reaction mixture was cooled, concentrated and the residue partitioned between DCM (50 mL) and aq. acetate buffer at pH 4.6. The aqueous layer was extracted with DCM and the combined extracts dried ($Na_2SO_4$), filtered and evaporated. The crude product was adsorbed onto $SiO_2$ (1 g) and added to a $SiO_2$ column that was eluted with an EtOAc/hexane gradient (0 to 70% EtOAc) and the recovered solid triturated with 1 mL of EtOAc/heptane (1:1) and collected to afford I-21.

4-(4,4,5,5-Tetramethyl-[1,3,2]dioxaborolan-2-yl)-2H-pyridazin-3-one 108)—A 1 L round-bottom flask was charged with 4-chloro-5-hydrazinyl-3(2H)-pyridazinone (8.0 g, 50 mmol), $CuSO_4.5H_2O$ (26.12 g, 10.5 mmol) and $H_2O$ (300 mL) and the mixture was stirred and heated at reflux overnight. The reaction was cooled to 0° C. and an aq. solution of NaOH was added until the pH was 4. The aqueous layer was thrice extracted with EtOAc (500 mL each). The combined extracts were dried ($Na_2SO_4$), filtered and evaporated. The remaining aqueous phase was adjusted to pH of 2 with 37% HCl and the solution extracted six times with EtOAc. The extracts were combined, dried ($Na_2SO_4$), filtered and evaporated to afford 4.75 g of 4-chloro-2H-pyridazin-3-one (110)

step 6—A microwave vial was charged with 110 (0.400 g, 3 mmol), bis-(pinacolato)diboron (0.934 g, 4 mmol), dicyclohexyl[2',4',6'-tris(1-methylethyl)[1,1'-biphenyl]-2-yl]-phosphine (X-Phos, 0.058 g, 0.12 mmol), $Pd_2(dba)_3$ (0.056 g, 0.061 mmol) and KOAc (0.902 g, 9 mmol) and the flask was evacuated and back-filled with Ar and sealed. Dioxane (6 mL) was added and the reaction heated at 110° C. overnight. The reaction mixture was cooled to RT and extracted with EtOAc (120 mL). The organic extract was washed sequentially with $H_2O$ (10 mL) and brine (10 mL), dried ($Na_2SO_4$), filtered and evaporated. The crude product was triturated with $Et_2O$ to afford 0.217 g of 108.

Example 10

N-(4-{(E)-2-[3,3-Dimethyl-7-(3-oxo-3,4-dihydro-pyrazin-2-yl)-2,3-dihydro-benzo furan-5-yl]-vinyl}-phenyl)-methanesulfonamide (I-23)

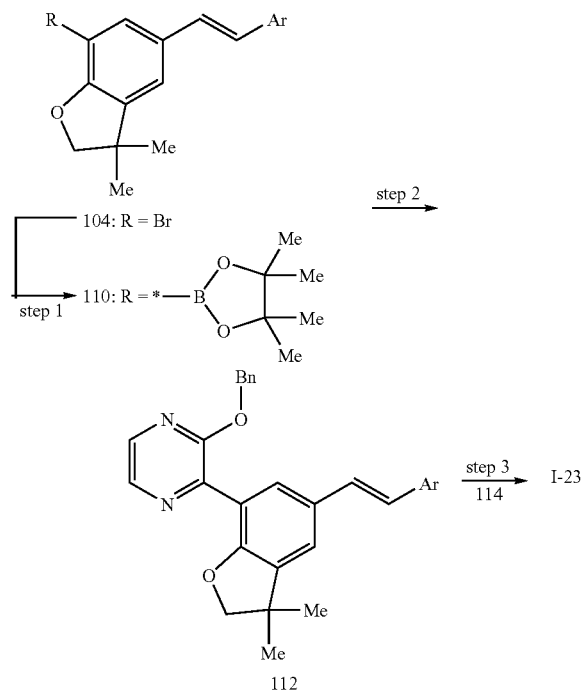

Ar = 4-methanesulfonylamino-phenyl step 1—A dried flask was charged 104 (0.250 g, 1 mmol), bis-(pinacolato)diboron (0.165 g, 1 mmol), $PdCl_2$ (dppf).DCM (0.097 g, 0.12 mmol), KOAc (0.174 g, 1.7 mmol) and DMSO (16 mL) and the flask was heated at 85° C. overnight. The reaction mixture was cooled to RT and partitioned between $H_2O$ (10 mL) and EtOAc (100 mL). The organic layers were washed five times with $H_2O$, then once with brine, dried ($Na_2SO_4$), filtered and evaporated. The crude product was purified on a $SiO_2$ column eluting with an EtOAc/hexane gradient (0 to 30% EtOAc) to afford 0.108 g (39%) of 110.

step 2—A microwave vial was charged 110 (0.099 g, 0.211 mmol), 114 (0.060 g, 0.27 mmol), $Pd(PPh_3)_4$ (0.024 g, 0.12 mmol), $Na_2CO_3$ (0.067 g, 0.631 mmol), MeOH (3 mL) and DCM (1 mL) and the flask was heated at 85° C. overnight. The tube was flushed with Ar, sealed and irradiated in a microwave synthesizer at 115° C. for 40 min. The reaction was cooled to RT and partitioned between DCM and $H_2O$. The combined organic layers were washed with brine, dried ($Na_2SO_4$), filtered and evaporated. The crude product was purified by $SiO_2$ chromatography eluting with an EtOAc/hexane gradient (0 to 40% EtOAc) to afford 0.063 g (56.6%) of 112.

step 3—A round-bottom flask was charged with 112 (0.081 g), HOAc (2.5 mL) and 48% HBr (50 µL) and the resulting solution stirred at RT for 7 h. The reaction mixture was poured into a mixture of ice and H₂O and solid NaHCO₃ was added until the effervescence ceased. The solution was extracted with DCM (50 mL) and the organic extract washed with brine, dried (Na₂SO₄), filtered and evaporated. The residue was adsorbed onto 1 g of SiO₂ which was applied to a SiO₂ column and eluted with a MeOH/DCM gradient (0 to 10% MeOH) to afford 43 mg (64%) of I-23.

2-benzyloxy-3-chloropyrazine (114)—To a solution of 2,3-dichloro-pyrazine (50.0 g, 0.335 mol), benzyl alcohol (39.9 g) and THF (250 mL) was added solid KOH. A slow exotherm occurred which raised the temperature to around 40° C. The reaction was maintained at 40-45° C. until the reaction was complete. The salts were washed with water, the THF evaporated and 114 purified by simple distillation.

Example 11

N-[3-tert-Butyl-2-methoxy-5-(3-oxo-2,3-dihydro-pyridazin-4-yl)-phenyl]-4-(2,2,2-trifluoro-ethylamino)-benzamide (I-20)

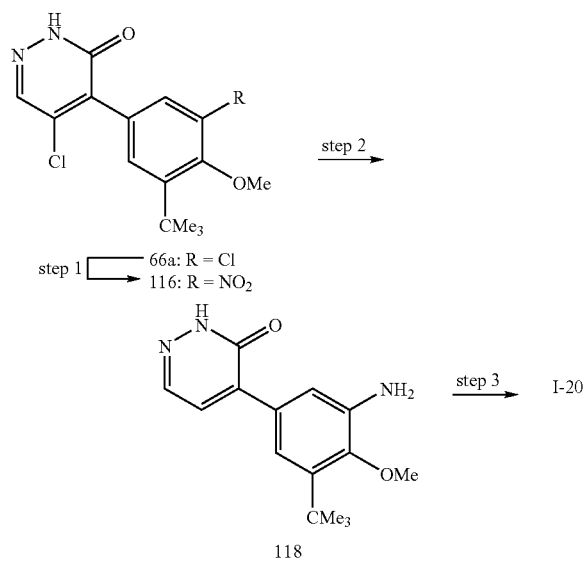

4-(2,2,2-Trifluoro-ethylamino)-benzoic acid (126)

step a—To a solution of 4-amino-benzoic acid (2.9 g, 21.15 mmol) in TFA (10 mL) cooled to 0° C. was added trifluoroacetic anhydride (3 mL, 21.24 mmol) and the resulting solution stirred for 1 h. The reaction mixture was poured onto ice (300 mL) and the white precipitate filtered, washed with H₂O and air dried to afford 4.83 g (98%) of 4-(2,2,2-trifluoro-acetylamino)-benzoic acid (120).

step b To a solution of 120 (4.29 g, 18.40 mmol) in MeOH (50 mL) and toluene (75 mL) was added dropwise trimethylsilyldiazomethane (15.64 mL, 31.3 mmol) until the yellow color persisted. The resulting solution was stirred for 30 min then the reaction was quenched with several drops of HOAc until the yellow color disappeared. The solvents were evaporated to afford methyl 4-(2,2,2-trifluoro-acetylamino)-benzoate (122) which was used in the next reaction without further purification.

step c—A vial was charged with 122 (1.0 g, 4.05 mmol) and DCM (15 mL) then tetrabutylammonium borohydride was added. The vial was capped and heated overnight in an oil bath at 50° C. The reaction mixture was cooled to RT and the DCM was evaporated. HOAc was added dropwise until H₂ evolution ceased. The solvents were evaporated and toluene was added. The mixture was made basic with dilute NaHCO₃, extracted with EtOAc, dried (MgSO₄), filtered and evaporated. The resulting solid was recrystallized from hexane to afford 0.349 g of methyl 4-(2,2,2-trifluoro-ethylamino)-benzoate (124)

step d—To a solution of 124 (0.349 g, 1.497 mmol), MeOH (3 mL), H₂O (1 mL) was added KOH (0.420 g, 7.48 mmol) and the resulting solution was heated at reflux for 1 h. The MeOH was evaporated and the residue diluted with H₂O (15 mL) and acidified to pH of 2 with 6N HCl. The white precipitate was filtered, washed with H₂O and air dried to afford 0.278 g (85%) of 126.

step 1—To a solution of 66a (0.217 g, 0.741 mmol) in HOAc (1.5 mL) is added dropwise, con HNO₃ (0.663 mL, 14.82 mmol) and the reaction stirred at RT for 2 h. The resulting mixture was poured onto a mixture of ice and H₂O, twice extracted with EtOAc. The combined extracts were dried (MgSO₄), filtered and evaporated. The crude product was purified by SiO₂ chromatography eluting with an EtOAc/hexane gradient (0 to 30% EtOAc) to afford 0.067 g (26.8%) of 116.

step 2—A mixture of 116 (0.067 g, 0.198 mmol), KOH (0.014 g, 0.248 mmol), Pd/C (50% H₂O) (0.042 g) and MeOH (5 mL) was stirred under 1 atmosphere of H₂ for 1 h. The catalyst was filtered and evaporated. The residue was partitioned between H₂O and EtOAc. The aqueous phase was again extracted with EtOAc and the combined organic extracts were dried (MgSO₄), filtered and concentrated in vacuo to afford 47 mg of 118 as an orange solid.

step 3—A solution of 118 (0.047 g, 0.172 mmol), 126 (0.041 g, 0.189 mmol) HATU (0.078 g, 0.206 mmol), DIPEA (0.060 mL) and dry DMF (3 mL) was stirred at 60° C. under Ar for 5 d. The reaction was diluted with H₂O and twice extracted with EtOAc. The combined extracts were washed with H₂O, dried (MgSO₄), filtered and evaporated. The crude product was purified on a preparatory SiO₂ TLC plate developed twice with 7% MeOH/DCM to afford 13 mg of I-20 as a yellow foam.

Example 12

4-Amino-N-[3-tert-butyl-2-methoxy-5-(3-oxo-2,3-dihydro-pyridazin-4-yl)-phenyl]-benzamide (I-19)

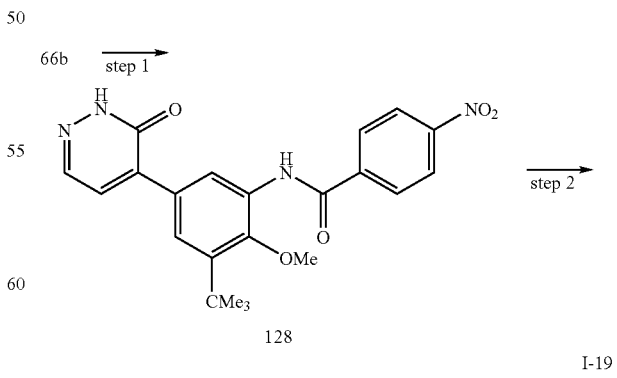

step 1—A microwave vial was charged with 66b (0.10 g, 0.297 mmol), 4-nitro-benzamide (0.049 g, 0.297 mmol), CuI (5365 mg, 0.030 mmol), K$_2$CO$_3$ (0.082 g, 0.593 mmol), N,N'-dimethyl-ethylenediamine (5.23 mg, 0.059 mmol) and toluene (1.5 mL). The vial was flushed with Ar, sealed and heated at 90° C. overnight. The reaction mixture was cooled, diluted with H$_2$O and twice extracted with EtOAc. The combined extracts were dried (MgSO$_4$), filtered and concentrated in vacuo. The crude product was adsorbed on SiO$_2$ and applied to a SiO$_2$ column and eluted with an EtOAc/hexane gradient (0 to 20% EtOAc) to afford 35.8 mg of 128.

step 2—A mixture of 128 (0.052 g, 0.012 mmol), Pd/C (26 mg, 50% H$_2$O), EtOAc (5 mL) and MeOH was hydrogenated at atmospheric pressure overnight. The solution was filtered through CELITE and the filtrate evaporated. The crude product was purified on a preparative SiO$_2$ TLC plate developed with 5% MeOH/DCM to afford 14 mg of I-19.

Example 13

N-(4-{(E)-2-[3-tert-Butyl-2-methoxy-5-(6-oxo-1,6-dihydro-pyrimidin-5-yl)-phenyl]-vinyl}-phenyl)-methanesulfonamide (I-22)

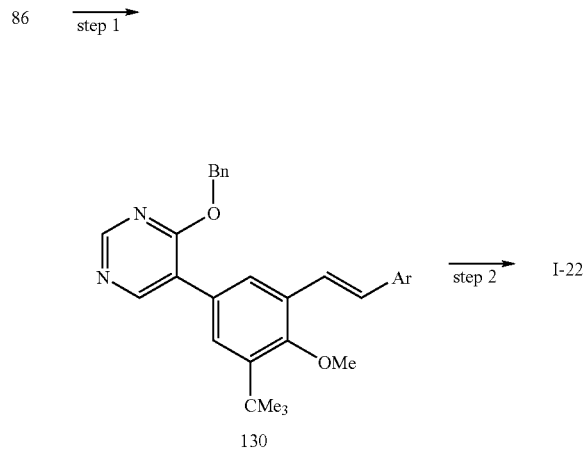

4-benzyloxy-5-bromo-pyrimidine (132)—To a suspension of 5-bromo-4(3H)-pyrimidinone (1.00 g, 5.6 mmol, CASRN 19808-30-1), 50% silver carbonate on CELITE (3.467 g, 6 mmol) and toluene (30 mL) was added benzyl bromide (0.75 mL, 6 mmol) and the resulting mixture heated at 125° C. for 1 h. The reaction was cooled and filtered through a glass microfiber filter which was rinsed with toluene. The filtrate was evaporated and the residue purified by SiO$_2$ chromatography eluting with an EtOAc/hexane gradient (0 to 10% EtOAc) to afford 0.140 g of 132, step 1—Suzuki coupling of 132 and 86 was carried out in accord with the procedure described in step 5 of example 1. The crude product was purified by SiO$_2$ chromatography eluting with an EtOAc/hexane gradient (0 to 50% EtOAc) to afford 130.

step 2 The debenzylation of 130 was carried out in accord with the procedure described in step 7 of example 1. The crude product was triturated with EtOAc/Et$_2$O to afford I-22.

Example 14

2-{2-[3-tert-Butyl-5-(2,4-dioxo-1,2,3,4-tetrahydro-pyrimidin-5-yl)-2-methoxy-phenyl]-ethyl}-5-methanesulfonylamino-benzoic acid methyl ester (I-25)

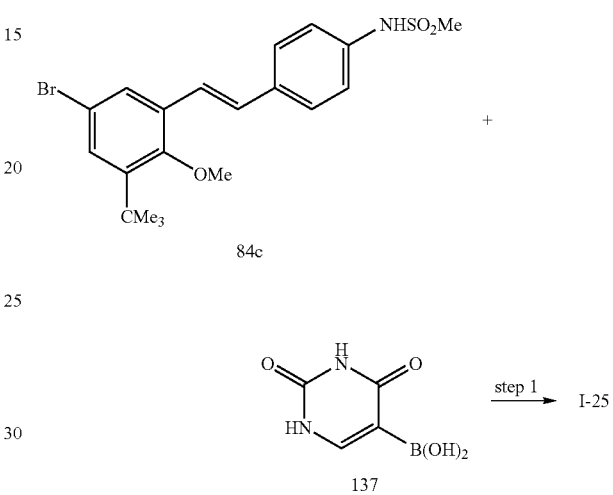

step 1—To a mixture of the 84c (100 mg, 0.23 mmol), 137 (53 mg, 0.34 mmol, CASRN 70523-22-7), Na$_2$CO$_3$ (73 mg, 0.69 mmol) in MeOH (3 mL) and DCM (1 mL) was added the Pd(PPh$_3$)$_4$ (26 mg, 0.023 mmol). The solution mixture was purged with Argon for two min and then irradiated in a microwave synthesizer at 110° C. for 40 min. TLC and LCMS analyses of an aliquot showed product and starting bromide. The reaction mixture was cooled to RT, diluted with DCM and filtered through CELITE. The filtrate was concentrated and the crude mixture was purified on a preparative TLC plate developed with 6% MeOH/DCM to afford 7.4 mg of I-25.

Example 15

N-(4-{(E)-2-[3-Cyclopropyl-2-methoxy-5-(3-oxo-2,3-dihydro-pyridazin-4-yl)-phenyl]-vinyl}-phenyl)-methanesulfonamide (I-26)

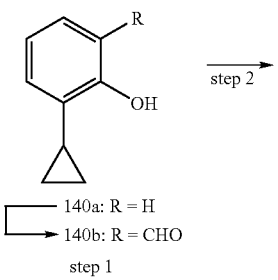

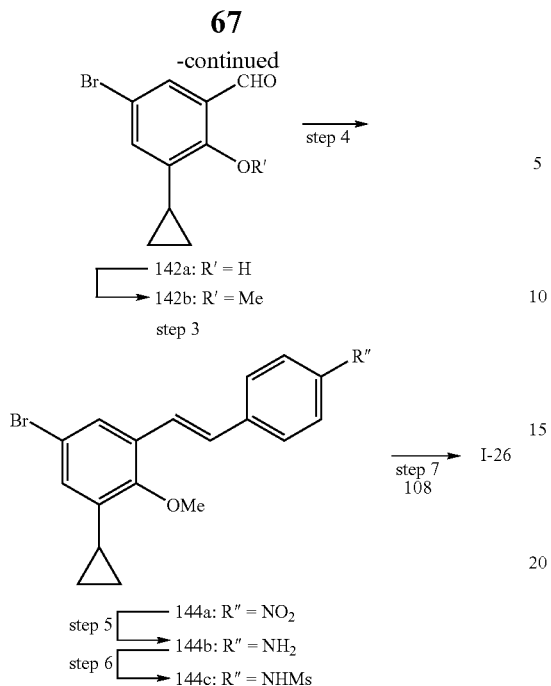

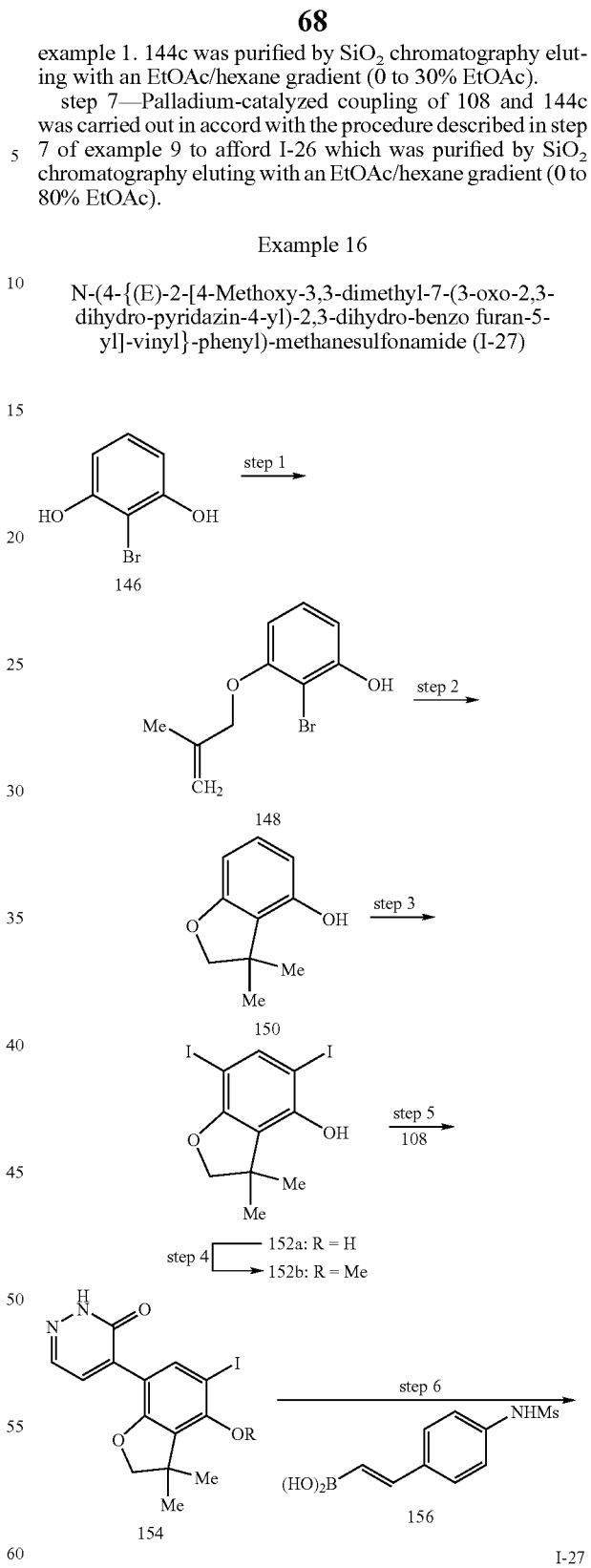

example 1. 144c was purified by SiO₂ chromatography eluting with an EtOAc/hexane gradient (0 to 30% EtOAc).

step 7—Palladium-catalyzed coupling of 108 and 144c was carried out in accord with the procedure described in step 7 of example 9 to afford I-26 which was purified by SiO₂ chromatography eluting with an EtOAc/hexane gradient (0 to 80% EtOAc).

Example 16

N-(4-{(E)-2-[4-Methoxy-3,3-dimethyl-7-(3-oxo-2,3-dihydro-pyridazin-4-yl)-2,3-dihydro-benzo furan-5-yl]-vinyl}-phenyl)-methanesulfonamide (I-27)

step 1—To a solution of 140a (0.438 g, 3.3 mmol) and MeCN (7 mL) was added paraformaldehyde (0.661 g 22 mmol), MgCl₂ (0.466 g, 4.9 mmol) and TEA (1.78 mL, 12 mmol) and the resulting suspension stirred at reflux for 7 h. (N. Gisch et al., *J. Med. Chem.* 2007 50(7):1658) The reaction mixture was cooled to RT and partitioned between DCM (100 mL) and 1N HCl (20 mL). The aqueous layer was extracted with DCM and the combined DCM extracts were dried (Na₂SO₄), filtered and evaporated. The crude product was purified by SiO₂ chromatography eluting with an EtOAc/hexane gradient (0 to 5% EtOAc) to afford 0.3940 (74.4%) of 140b.

step 2—Bromination of 140b was carried out with tetrabutylammonium tribromide in accord with the procedure described in step 5 of example 4 to afford 142a which was purified by SiO₂ chromatography eluting with an EtOAc/hexane gradient (0 to 5% EtOAc).

step 3—O-Methylation of 142a was carried out in accord with the procedure described in step 6 of example 4 to afford 142b which was used without additional purification.

step 4—Condensation of 142b and diethyl 4-nitro-benzylphosphonate was carried out in accord with the procedure described in step 1 of example 1 to afford 144a which was purified by SiO₂ chromatography eluting with an EtOAc/hexane gradient (0 to 10% EtOAc).

step 5—To a suspension of 144a (0.630 g, 1.68 mmol), MeOH (12 mL) and H₂O (12 mL) was added NH₄Cl (0.900 g, 17 mmol) and iron powder (0.451 g, 8.1 mmol, <10 micron) and the resulting mixture was heated and stirred overnight at reflux. The reaction mixture was cooled to RT and filtered through a glass microfiber filter which was rinsed with MeOH/EtOAc/DCM. The filtrate was concentrated and partitioned between DCM (100 mL) and H₂O (15 mL). The organic extract was washed with brine and the brine was back extracted with DCM. The combined DCM extracts were dried (Na₂SO₄), filtered and evaporated to afford 0.55 g (94.9%) of 144b which was used in the next step without additional purification.

step 6—Conversion of 144b to the sulfonamide 144c was carried out in accord with the procedure described in step 3 of step 1—Alkylation of 146 with 3-bromo-2-methyl-propene was carried out in accord with the procedure in step 1 of example 9 to afford 148 which was purified by SiO₂ chromatography eluting with an EtOAc/hexane gradient (0 to 10% EtOAc).

step 2—A dried round-bottom flask was charged with 148 (3.720 g, 15 mmol), benzene (150 mL), tributyltin hydride (6.695 g, 22 mmol) and AIBN (0.251 g, 2 mmol) and the reaction mixture was heated at reflux overnight. The reaction mixture was cooled to RT and a 10% aq. KF solution was added and the resulting two-phase mixture stirred vigorously for 3.5 h. The phases were separated and the aqueous layer was extracted with EtOAc (150 mL). The organic phase was washed with brine, dried ($Na_2SO_4$), filtered and concentrated in vacuo. The crude product was purified by $SiO_2$ chromatography eluting with an EtOAc/hexane gradient (0 to 10% EtOAc) to afford 2.53 g (90.6%) of 150.

step 3—To a solution of iodine (3.091 g, 12 mmol) and EtOH (40 mL) was added $Ag_2SO_4$ (3.798 g, 0.12 mmol) and 150 (1.00 g, 6 mmol). The brown suspension was stirred at RT for 2 h. The mixture was filtered through a pad of CELITE and pad was washed with EtOAc/EtOH. The filtrate was concentrated in vacuo. The crude product was purified by $SiO_2$ chromatography eluting with an EtOAc/hexane gradient (0 to 10% EtOAc) to afford 1.71 g (68%) of 152a.

step 4-O-Methylation of 152a was carried out in accord with the procedure described in step 6 of example 4 to afford 152b which was used without additional purification.

step 5-Palladium-catalyzed coupling of 108 and 152b was carried out in accord with the procedure described in step 7 of example 9. The crude product was purified by $SiO_2$ chromatography eluting with an EtOAc/hexane gradient (0 to 40% EtOAc) to afford 49 mg (15%) of 154.

step 6—A microwave vial was charged with 154 (0.049 g, 0.12 mmol), 156 (0.039 g, 0.16 mmol, CASRN 1132942-08-5), $Na_2CO_3$ (0.039 g, 0.37 mmol), $Pd(PPh_3)_4$ (0.014 g, 0.012 mmol), MeOH (1.4 mL) and toluene (0.7 mL). The vial was flushed with argon, sealed and irradiated in a microwave synthesizer at 120° C. for 1 h. The reaction mixture was cooled and partition between DCM (50 mL) and NaOAc buffer adjusted to pH 4.6. The aqueous buffer was extracted with DCM and the combined organic extracts were dried ($Na_2SO_4$), filtered and concentrated in vacuo. The crude product was purified by $SiO_2$ chromatography eluting with an EtOAc/hexane gradient (0 to 60% EtOAc) to afford 43 mg (74.7%) of I-27.

I-28 was prepared analogously except in step 5, 108 was replaced with 137 to afford N-(4-{(E)-2-[7-(2,4-dioxo-1,2,3,4-tetrahydro-pyrimidin-5-yl)-4-methoxy-3,3-dimethyl-2,3-dihydro-benzofuran-5-yl]-vinyl}-phenyl)-methanesulfonamide which was purified by $SiO_2$ chromatography and eluted with a gradient of DCM and a solution of 10% MeOH/DCM/ 0.5% $NH_4OH$ (0 to 50%). The recovered product was rechromatographed using the same gradient then recovered and triturated with MeOH to afford I-28.

Example 17

N-(6-{(E)-2-[3-tert-Butyl-5-(2,4-dioxo-1,2,3,4-tetrahydro-pyrimidin-5-yl)-2-methoxy-phenyl]-vinyl}-pyridin-3-yl)-methanesulfonamide (I-29)

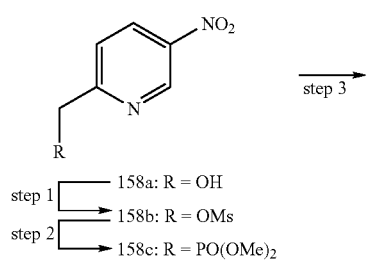

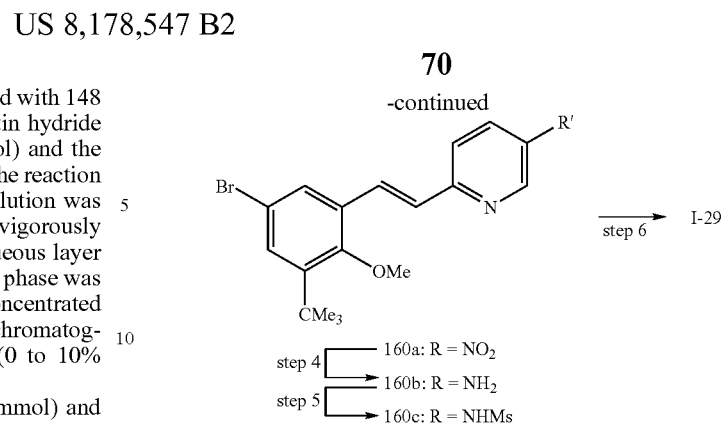

step 1—To a solution of 158a (1.0 g, 6.553 mmol, CASRN 36625-57-7) in DCM (40 mL) cooled to 0° C. was added sequentially TEA (1.2 mL, 8.518 mmol) and methanesulfonyl chloride (0.56 mL, 7.208 mmol). After 30 min the solution was washed with $H_2O$ and the organic phase dried ($Na_2SO_4$), filtered and concentrated in vacuo. The crude product was purified by $SiO_2$ chromatography eluting with 40% EtOAc/hexane to afford 1.44 g (95%) of 158b as a yellow solid.

step 2—To a solution of 158b (1.44 g, 6.218 mmol) in THF (20 mL) was added LiBr (0.594 g, 6.840 mmol) After stirring for 2 h at RT the reaction mixture was diluted with EtOAc, washed sequentially with $H_2O$ and brine. The organic extract was dried ($Na_2SO_4$), filtered and concentrated in vacuo to afford an orange oil which was dissolved in THF (5 mL) and trimethylphosphite (5 mL) was added. The solution was warmed to 100° C. for 5 h the concentrated. The crude product was purified by $SiO_2$ chromatography eluting with an EtOAc/MeOH gradient (0 to 5% MeOH) to afford 1.72 g of 158c as an orange oil.

Condensation of 158c and 28 (step 3) was carried out in accord with the procedure described in step 1 of example 1 to afford 160a. Reduction of the nitro group (step 4) was carried out with iron powder as described in step 5 of example 15 and the product was purified by $SiO_2$ chromatography eluting with 40% EtOAc/hexane to afford 160b. Sulfonylation of 160b (step 5) was carried out as described in step 3 of example 1 and the crude product was purified by $SiO_2$ chromatography eluting with an EtOAc/hexane gradient (20 to 80% EtOAc) to afford 160c.

Palladium-catalyzed coupling of 160c and 137 was carried out in accord with the procedure described in example 14. The crude product was purified by $SiO_2$ chromatography eluting with 10% MeOH/DCM. The product co-eluted with uracil and the solid was stirred in hot $H_2O$ for several hours. The hot slurry was filtered and washed with $Et_2O$ and dried in vacuo overnight to afford N-(6-{(E)-2-[3-tert-butyl-5-(2,4-dioxo-1, 2,3,4-tetrahydro-pyrimidin-5-yl)-2-methoxy-phenyl]-vinyl}-pyridin-3-yl)-methanesulfonamide (I-29).

Example 18

N-(4-{(E)-2-[3-(1-Difluoromethyl-cyclopropyl)-5-(2,4-dioxo-1,2,3,4-tetrahydro-pyrimidin-5-yl)-2-methoxy-phenyl]-vinyl}-phenyl)-methanesulfonamide (I-30)

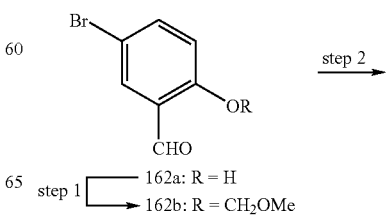

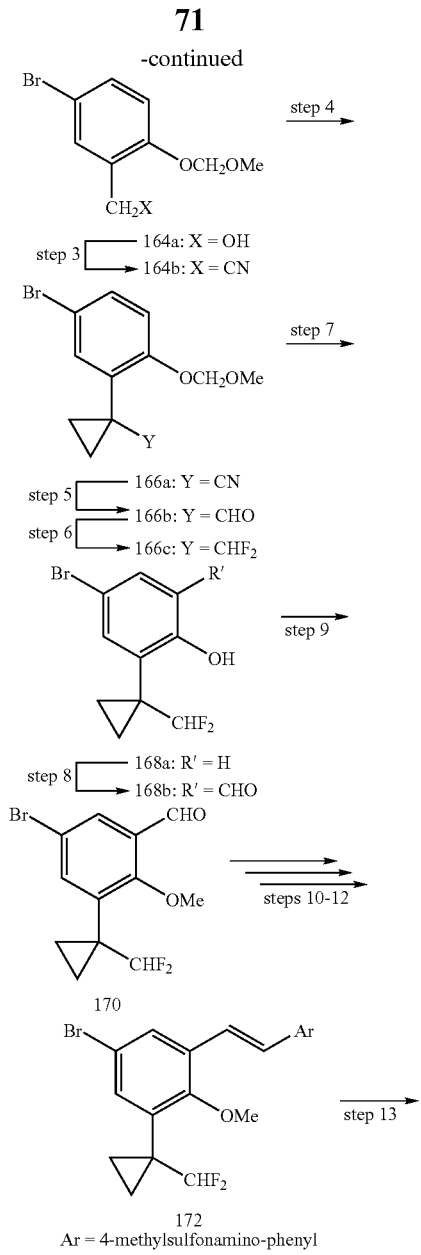

Ar = 4-methylsulfonamino-phenyl step 1—To a solution of 5-bromosalicylaldehyde (162a, 10.0 g, 49.7 mmol) in DMF (100 mL) at RT was added K$_2$CO$_3$ (13.7 g, 99.4 mmol) followed by chloromethyl methyl ether (tech grade, 5.2 mL, 54.7 mmol). The reaction mixture was stirred at RT overnight then quenched with H$_2$O and thrice extracted with EtOAc. The organic phase was thrice washed with H$_2$O, dried (MgSO$_4$) and concentrated to afford 11.6 g (96%) of 162b as a yellow oil.

step 2—To a solution of 162b (11.6 g, 47.3 mmol) in MeOH (100 mL) at 0° C. was slowly added NaBH$_4$ (1.87 g, 49.6 mmol). The reaction mixture was stirred at 0° C. for 1 h then quenched with H$_2$O and brine. The organic phase was thrice extracted with EtOAc, dried (MgSO$_4$), filtered and concentrated to afford 11.3 g (97%) of 164a as a pale yellow oil.

step 3—To a solution of alcohol 164a (10.0 g, 40.5 mmol) in DCM (80 mL) cooled to 0° C. was added TEA (7.3 mL, 52.6 mmol) and methanesulfonyl chloride (3.4 mL, 44.5 mmol). The reaction mixture was stirred for 1 h then quenched with H$_2$O and extracted with DCM. The organic extracts were dried (MgSO$_4$), filtered and concentrated to a light yellow oil. To a solution of this oil in DMF (50 mL) was added LiBr (3.9 g, 44.5 mmol) and the reaction mixture was stirred at RT for 1 h. A solution of NaCN (3.0 g, 60.7 mmol) in H$_2$O (5 mL) was slowly added, using an ice bath to control the exothermic reaction. After the addition was complete, the reaction mixture was stirred at RT for 1 h then quenched with H$_2$O and thrice extracted with EtOAc. The organic phase was thrice washed with H$_2$O then dried (MgSO$_4$), filtered and concentrated to afford 10.5 g of 164b as a yellow oil.

step 4—To a solution of 164b (2.6 g, 10.1 mmol) in DMF (25 mL) cooled to 0° C. was added NaH (60% in mineral oil, 0.89 g, 22.2 mmol). The reaction mixture was stirred at 0° C. for 0.5 h then 1,2-dibromoethane (0.96 mL, 11.1 mmol) was added dropwise. The reaction mixture was warmed to RT and stirred for 1 h then quenched with H$_2$O and thrice extracted with EtOAc. The combined organic extracts were thrice washed with H$_2$O then dried (MgSO$_4$), filtered and concentrated. The residue was purified by SiO$_2$ chromatography eluting with 10% EtOAc/hexanes to afford 1.83 g (64%) of 166a as a yellow oil.

step 5—To a solution of nitrile 166a (1.83 g, 6.5 mmol) in DCM (40 mL) cooled to −78° C. was added DIBAL-H (1.27 mL, 7.1 mmol) dropwise. The reaction mixture was stirred at −78° C. for 2 h then quenched with MeOH (0.5 mL) and warmed to RT. A saturated solution of Rochelle's salt (40 mL) was added and the biphasic mixture was stirred vigorously for 30 min. The phases were separated and the aqueous phase was extracted with DCM. The combined organic extracts were dried (MgSO$_4$), filtered and concentrated. The crude residue was purified by SiO$_2$ chromatography eluting with 2% EtOAc/DCM to afford 1.49 g (81%) of 166b as a pale yellow oil.

step 6—To a solution of 166b (4.9 g, 17.2 mmol) in DCM (80 mL) was slowly added (diethylamino)sulfur triflouride (6.8 mL, 51.6 mmol). The reaction mixture was stirred at RT overnight then quenched by slowly pouring onto ice. The mixture was diluted with H$_2$O and extracted with DCM. The combined organics were dried (MgSO$_4$), filtered and concentrated. The crude residue was purified by SiO$_2$ chromatography eluting with 10% EtOAc/hexanes to afford 4.07 g (77%) of 166c as a colorless oil.

step 7—To a solution of 166c (4.05 g, 13.2 mmol) in DCM (60 mL) cooled 0° C. was added 4 Å powdered molecular sieves (4 g) followed by bromotrimethylsilane (5.2 mL, 39.6 mmol). The reaction mixture was allowed to warm to RT and stirred overnight then filtered to remove the sieves which were rinsed with DCM. The filtrate was washed sequentially with sat'd. aq. NaHCO$_3$ and H$_2$O then dried (MgSO$_4$), filtered and concentrated. The crude residue was purified by SiO$_2$ chromatography eluting with an EtOAc/hexane gradient (10% to 20% EtOAc) to afford 2.85 g (82%) of 168a as a pale yellow oil.

step 8—To a solution of 168a (2.85 g, 10.8 mmol) in anhydrous MeCN (50 mL) was added TEA (5.6 mL, 40.5 mmol), MgCl$_2$ (1.54 g, 16.2 mmol), and paraformaldehyde (2.27 g, 75.6 mmol). The bright yellow reaction mixture was heated at reflux for 5 h then cooled to RT and quenched with 1.0 M aqueous HCl. The mixture was thrice extracted with EtOAc then the combined organics were dried (MgSO$_4$), filtered and concentrated. The crude residue was purified by SiO$_2$ chromatography eluting with an EtOAc/hexane gradient (10% to 20% EtOAc) to afford 1.04 g (33%) of 168b as an off-white solid.

step 9—To a solution of 168b (1.04 g, 3.6 mmol) in DMF (15 mL) was added K$_2$CO$_3$ (1.0 g, 7.2 mmol) followed by iodomethane (0.27 mL, 4.3 mmol). The reaction mixture was stirred at RT for 4 h then quenched with H₂O and thrice extracted with EtOAc. The combined extracts were thrice washed with H₂O, dried (MgSO₄) filtered and concentrated to afford 1.06 g (97%) of 170 as a pale yellow solid which required no further purification.

steps 10-12—Condensation of 170 with diethyl 4-nitrobenzyl-phosphonate (step 10), reduction of the nitro group (step 11) and sulfonylation of the amine (step 12) can be carried out in accord with the procedures in steps 1-3 of example 1 to afford 172. Palladium-catalyzed coupling of 172 and 137 is carried out in accord with the procedure in example 14.

Example 19

N-(4-{(E)-2-[3-(1-Difluoromethyl-cyclopropyl)-2-methoxy-5-(3-oxo-3,4-dihydro-pyrazin-2-yl)-phenyl]-vinyl}-phenyl)-methanesulfonamide (I-31)

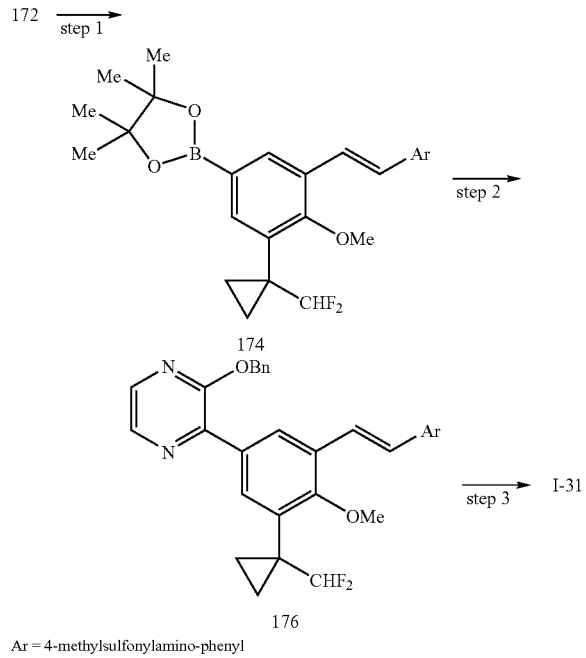

Ar = 4-methylsulfonylamino-phenyl step 1—A suspension of 172 (0.215 g, 0.455 mmol), bis-(pinacolato)diboron (0.127 g, 0.501 mmol), KOAc (0.134 g, 1.37 mmol), Pd(dppf)Cl₂·CH₂Cl₂ (0.011 g, 0.0137 mmol), dppf (0.008 g, 0.0137 mmol) and dioxane (3 mL) were stirred overnight at 100° C. The reaction mixture was cooled to RT and quenched with H₂O and extracted with EtOAc. The organic extract was dried (MgSO₄), filtered and concentrated in vacuo. The crude product was purified by SiO₂ chromatography eluting with an EtOAc/hexane gradient (10 to 50% EtOAc) to afford 255 mg (95%) of 174 as a colorless oil which contained about 7% of bis-(pinacolato)diboron.

step 2—A microwave vial was charged with 174 (0.236 g, 0.454 mmol), 2-benzyloxy-3-chloro-pyrazine (0.110 g, 0.50 mmol), Pd(PPh₃)₄ (26 mg, 0.0227 mmol), Na₂CO₃ (96 mg, 0.909 mmol), MeOH (2 mL) and DCM (0.5 mL), sealed and irradiated in a microwave synthesizer ant 115° C. for 0.5 h. An addition aliquot of the pyrazine (40 mg) was added and heated continued for another 20 min. The reaction mixture was cooled to RT, diluted with DCM and sequentially washed with H₂O and brine. The aqueous phase was back extracted with DCM. The combined DCM extracts were dried (MgSO₄), filtered and concentrated in vacuo. The crude product was purified by SiO₂ chromatography eluting with an EtOAc/hexane gradient (10 to 50% EtOAc) to afford 190 mg (60%) of 176 as a white foam.

step 3—To a solution of 176 (0.190 g, 0.329 mmol) and HOAc (3 mL) was added 48% HBr (0.11 mL) and the resulting solution was stirred and heated to 52° C. for 1.5 h. The mixture was cooled to RT and carefully added to sat'd. aq. NaHCO₃. The mixture was diluted with EtOAc which resulted in the formation of a precipitate in the organic layer that was filtered and twice washed with sat'd. aq. NaHCO₃. The filtrated was concentrated to afford a yellow solid which was triturated with EtOAc. The solids were combined to afford 0.111 g (85%) of I-31 as a yellow solid.

Example 20

N-(4-{(E)-2-[3-tert-Butyl-5-(2-chloro-6-oxo-1,6-dihydro-pyrimidin-5-yl)-2-methoxy-phenyl]-vinyl}-phenyl)-methanesulfonamide (I-32)

Palladium-catalyzed coupling of 2-chloro-4-(phenylmethoxy)-5-(4,4,5,5-tetramethyl-1,3,2-dioxaborolan-2-yl)-pyrimidine (149, CASRN 1073354-22-9) and 84c was carried out in accord with the procedure described in example 14 to afford N-(4-{(E)-2-[5-(4-benzyloxy-2-chloro-pyrimidin-5-yl)-3-tert-butyl-2-methoxy-phenyl]-vinyl}-phenyl)-methanesulfonamide. Cleavage of the benzyl group was carried out in accord with the procedure in step 3 of example 19. The crude product was purified on a preparative SiO₂ plate developed with 5% MeOH/DCM to afford I-32.

N-(4-{(E)-2-[3-tert-Butyl-5-(2-dimethylamino-6-oxo-1,6-dihydro-pyrimidin-5-yl)-2-methoxy-phenyl]-vinyl}-phenyl)-methanesulfonamide (I-33) was prepared analogously except in step 1,4-benzyloxy-2-chloro-pyrimidin-5-yl boronic acid was replaced with 4-benzyloxy-2-dimethylamino-pyrimidin-5-yl boronic acid (CASRN 205672-21-5).

N-(4-{(E)-2-[3-tert-Butyl-2-methoxy-5-(2-methoxy-6-oxo-1,6-dihydro-pyrimidin-5-yl)-phenyl]-vinyl}-phenyl)methanesulfonamide (I-34) was prepared analogously except in step 1,4-benzyloxy-2-chloro-pyrimidin-5-yl boronic acid was replaced with 2,4-dimethoxy-pyrimidin-5-yl boronic acid (CASRN 89641-18-9).

Example 21

N-(4-{(E)-2-[3-tert-Butyl-2-methoxy-5-(6-oxo-1,6-dihydro-[1,2,4]triazin-5-yl)-phenyl]-vinyl}-phenyl)-methanesulfonamide (I-36)

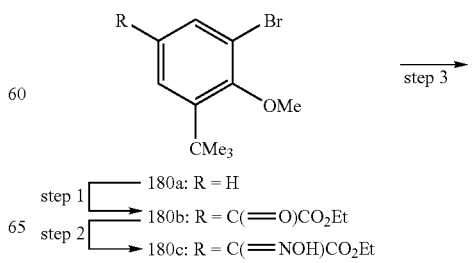

180a: R = H
180b: R = C(=O)CO₂Et
180c: R = C(=NOH)CO₂Et

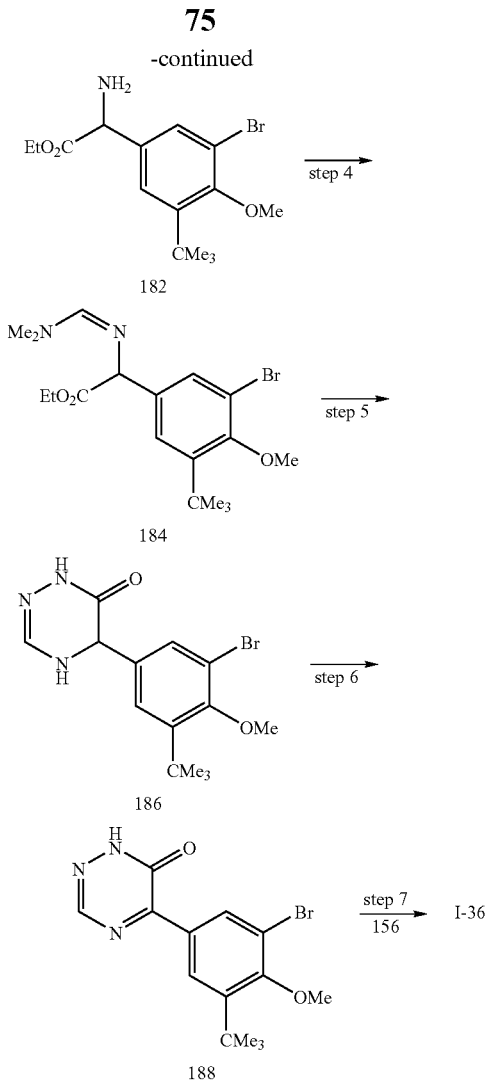

step 1—To a suspension of AlCl$_3$ (4.19 g, 31 mmol) and DCM (25 mL) cooled to 0° C. and maintained under nitrogen was added was added dropwise over 10 min ethyl chloroformate (4.24 g, 31 mmol) and the resulting solution was stirred for an additional 15 min. To the resulting solution was added dropwise over 15 min via syringe 180a (4.0 g, 16.5 mmol, CASRN 1007375-07-6). The resulting solution was allowed to warm to RT and stirring was continued for 1.5 h. The solution was poured into a mixture of ice (150 g) and con HCl (50 mL) and the resulting mixture extracted with DCM (3×50 mL). The combined organic extracts were washed with dilute NaOH, then twice with brine, dried (Na$_2$SO$_4$), filtered and concentrated in vacuo. The crude product was purified by SiO$_2$ chromatography eluting with 10% EtOAc/hexane to afford 4.22 g (74%) of 180b step 2—A solution of 180b (4.2 g, 12.2 mmol), hydroxylamine hydrochloride (1.36 g, 19.6 mmol), NaOAc (1.1 g, 14.5 mmol) and EtOH (65 mL) was heated to reflux for 3 h, cooled, concentrated and partitioned between EtOAc and H$_2$O. The EtOAc extract was washed with brine, dried (Na$_2$SO$_4$), filtered and concentrated in vacuo to afford 4.5 g (99%) of 180c as a white solid.

step 3—A solution of 180c (4.4 g, 12.3 mmol) and MeOH (25 mL)/H$_2$O (15 mL)/HCO$_2$H (15 mL) cooled in an ice-water bath was added portion wise over 1 h, Zn dust 1.61 g, 24.6 mmol). (S. Kukolja, et al., *J. Med. Chem.* 1985 28:1886) The solution was stirred at 0° C. for 7 h, removed from the ice bath and stirred an addition 2 h. TLC analysis of the mixture indicated only partial transformation occurred and another aliquot of Zn (0.8 g, 1, eq.) was added and the reaction stirred for 40 h at RT. The mixture was filtered through CELITE and the pad washed with MeOH. The filtrate was concentrated, dilute HCl was added and the solution was extracted with EtOAc. The EtOAc layer was washed with 1N NaOH, dried (Na$_2$SO$_4$), filtered and concentrated in vacuo. The crude product was purified by SiO$_2$ chromatography eluting with an EtOAc/hexane gradient (75 to 100% EtOAc) to afford 2.9 g (67%) of 182 as a white solid.

step 4—To a solution of 182 (2.7 g, 8.0 mmol) and DMF (50 mL) was added dimethoxymethyl-dimethyl-amine (1.42 g, 12 mmol) and the resulting solution stirred overnight at RT. The reaction mixture was concentrated in vacuo and finally subjected to a high vacuum for 2 h to afford 184 which used without additional purification.

step 5—To a solution of 184 (3.2 g, 8.0 mmol) and EtOH (25 mL) was added hydrazine (0.5 mL, 15.9 mmol) and the resulting solution was heated to reflux for 2 h. The solution was cooled to RT and concentrated in vacuo and purified by SiO$_2$ chromatography eluting with an EtOAc/hexane gradient (50 to 100% EtOAc) to afford 1.7 g (63%) of 186 as a white solid.

step 6—To a solution of 186 (1.0 g, 2.9 mmol) in CHCl$_3$ (7.5 mL) and MeOH (7.5 mL) was added NaOAc (0.29 g, 3.5 mmol) and the resulting solution cooled in an ice/MeOH bath. To this solution was added bromine (0.34 g, 2.2 mol) dropwise over 1 to 2 min. After approximately 1 min, starting material appeared to have been consumed (TLC) and the reaction was quenched with aq. Na$_2$CO$_3$ and extracted with CHCl$_3$. The combined extracts were dried (Na$_2$SO$_4$), filtered and concentrated in vacuo. The crude product was purified by SiO$_2$ chromatography eluting with an EtOAc/hexane gradient (50 to 100% EtOAc) to afford 0.58 g (77%) of 188 as a yellow solid.

step 7—Palladium-catalyzed coupling of 188 and 156 was carried out in accord with the procedure described in step 6 of example 16 except Pd(PPh$_3$)$_4$ was replaced with 1,1'-bis(di-tert-butylphosphino)ferrocene palladium dichloride. The crude product was purified by SiO$_2$ chromatography eluting with an EtOAc/hexane gradient (0 to 100% EtOAc) to afford I-36.

Example 22

N-{6-[3-tert-Butyl-2-methoxy-5-(6-oxo-1,6-dihydro-[1,2,4]triazin-5-yl)-phenyl]-naphthalen-2-yl}-methanesulfonamide (I-37)

A microwave tube was charged with 186 (0.064 g, 0.19 mmol), N-[6-(4,4,5,5-tetramethyl-1,3,2-dioxaborolan-2-yl)-2-naphthalenyl]-methanesulfonamide (0.13 g, 0.37 mmol, CASRN 1132940-88-5), Pd(PPh$_3$)$_4$ (0.005 g, 0.004 mmol), Na$_2$CO$_3$ (0.020 g, 0.19 mmol), PhMe (1 mL) and MeOH (1 mL) and irradiated at 115° C. for 1 h. The reaction was cooled and the crude product suspended in CHCl$_3$ and adsorbed on a SiO$_2$ column and eluted with an EtOAc/hexane gradient (50 to 100% EtOAc to a solution of 1% HOAc/EtOAc) which afforded a solid which was triturated with Et₂O/hexane and filtered to afford 8 mg of I-37.

Example 23

N-(4-{(E)-2-[3-tert-Butyl-2-methoxy-5-(2-methoxy-6-oxo-1,6-dihydro-pyrimidin-5-yl)-phenyl]-vinyl}-3-methoxymethyl-phenyl)-methanesulfonamide (I-39)

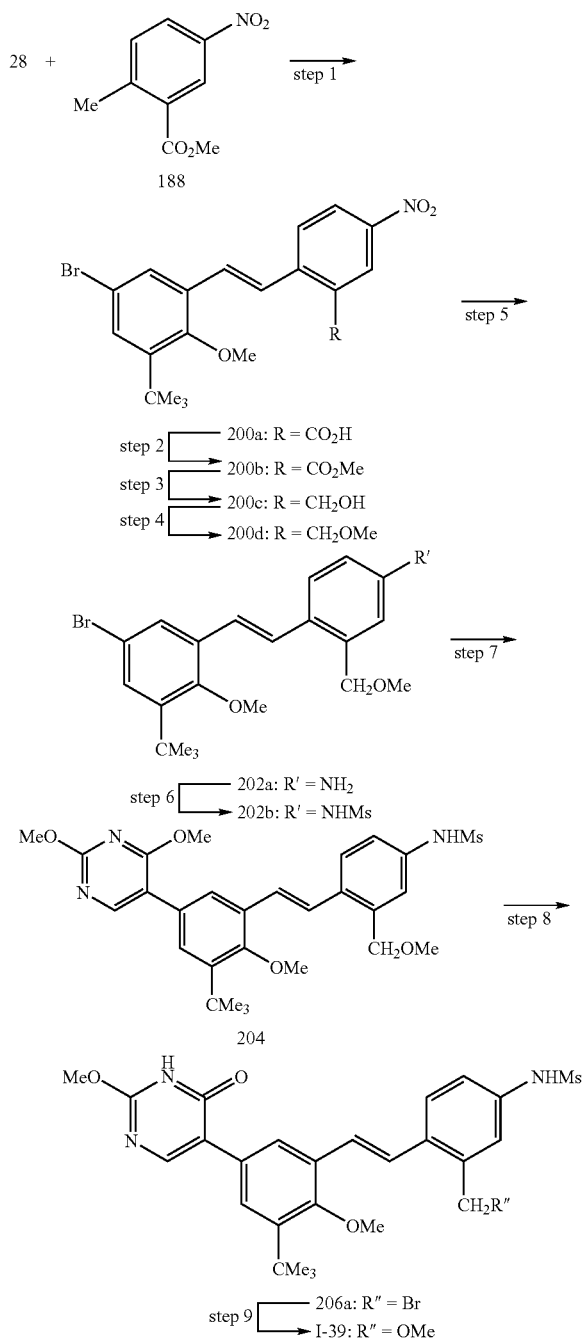

step 1—A solution of 28 (4.17 g, 15.39 mmol), 188 (2.00 g, 10.26 mmol), DBU (3.1 mL, 20.73 mmol) and DMSO (10 mL) was stirred overnight at RT then heated to 50° C. for 1 h. To the solution was added 1N NaOH and the resulting solid filtered. The filtrate was acidified with 6N HCl extracted with EtOAc and the combined extracts were dried (Na₂SO₄), filtered and evaporated to afford 2.51 g of 200a.

step 2—A solution of 200a (2.00 g, 4.608 mmol), iodomethane (1.05 mL, 16.87 mmol), K₂CO₃ (1.92 g, 13.89 mmol) and DMF (10 mL) was stirred overnight at RT. The resulting solution was filtered and the filtrate was diluted with EtOAc and washed with 1N HCl, H₂O and brine. The organic phase was dried (Na₂SO₄), filtered and concentrated in vacuo to afford 1.94 g (94%) of 200b.

step 3—To a solution of 200b (500 mg, 1.12 mmol) in THF (10 mL) cooled to 0° C., was added LiAlH₄ (1.7 mL, 1.7 mmol, 1.0 M solution in THF). The reaction was gradually warmed to RT over 45 min, then re-cooled to 0° C. and quenched with NaHSO₄ solution. The suspension was concentrated, diluted with EtOAc, and washed sequentially with 1N HCl and brine. The organic extract was dried (Na₂SO₄), filtered and concentrated in vacuo. The crude product was purified by SiO₂ chromatography eluting with an EtOAc/hexane gradient (5% to 10% EtOAc) to afford 129 mg (28%) of {2-[(E)-2-(5-bromo-3-tert-butyl-2-methoxy-phenyl)-vinyl]-5-nitro-phenyl}-methanol (200c) as a yellow oil.

step 4—To a solution of 200c (116 mg, 0.276 mmol) in DMF (5 mL) was added sodium hydride (0.022, 0.550 mmol, 60% mineral oil dispersion). After 20 min, methyl iodide (0.040 mL, 0.643 mmol) was added and the resulting suspension was stirred overnight. The reaction mixture was diluted with EtOAc, thrice washed with brine, dried (Na₂SO₄), filtered and concentrated in vacuo. The crude product was purified by SiO₂ chromatography eluting with an EtOAc/hexane gradient (5% to 15% EtOAc) to afford 81 mg (68%) of 200d as an orange oil.

Reduction of the nitro group (step 5) was carried out with SnCl₂.2H₂O in DMF/EtOAc in accord with the procedure described in step 2 of Example 1 to afford 202a. Sulfonylation of the amine to afford 202b (step 6) is carried out in accord with the procedure described in step 3 of example 1 step 7—A tube was charged with 202b (100 mg, 0.207 mmol), 2,4-dimethoxy-pyrimidin-5-yl boronic acid (207 mg, 0.261 mmol), Pd(PPh₃)₄ (27 mg, 0.023 mmol), Na₂CO₃ (61 mg, 0.576 mmol), MeOH (3 mL) and DCM (1 mL), sealed and irradiated in a microwave synthesizer at 115° C. for 30 min. The reaction mixture was concentrated, diluted with EtOAc, washed with brine, dried (Na₂SO₄), filtered and concentrated in vacuo. The crude product was purified by SiO₂ chromatography eluting with an EtOAc/hexane gradient (50 to 100% EtOAc) to afford 35 mg (31%) of 204 as a cream colored solid.

step 8—A solution of 204 (35 mg, 0.065 mmol), 48% HBr (0.05 mL, 0.436 mmol) in HOAc (3 mL) was heated at 60° C. overnight in a sealed tube. The reaction mixture was carefully poured into a mixture of sat'd. aq. NaHCO₃/ice which was extracted with EtOAc. The combined extracts were dried (Na₂SO₄), filtered and dried in vacuo to afford 206 which was used in the final step without addition purification.

step 9—A solution of 206 (0.065 mmol), sodium methoxide (10 mL, 5 mmol, 0.5M in methanol) and methanol (10 mL) was stirred at RT overnight. The reaction mixture was concentrated, diluted with EtOAc and acidified with 6N HCl. The combined EtOAc extracts were dried (Na₂SO₄), filtered and concentrated in vacuo. The crude product was purified on a preparatory SiO₂ plate developed with 2:1 EtOAc/hexane to afford 12 mg (34%) of I-39 as an off-white solid.

Example 24

N-(4-{(E)-2-[3-tert-Butyl-5-(2,4-dioxo-1,2,3,4-tetrahydro-pyrimidin-5-yl)-2-methoxy-phenyl]-vinyl}-3-methoxymethyl-phenyl)-methanesulfonamide (I-40)

A sealed tube was charged with 202b (100 mg, 0.207 mmol), 137 (45 mg, 0.289 mmol), Pd(PPh$_3$)$_4$ (24 mg, 0.21 mmol), Na$_2$CO$_3$ (57 mg, 0.537 mmol), MeOH (2 mL), DCM (1 mL) and DMF (1 mL), sealed and irradiated in a microwave synthesizer at 115° C. for 30 min. LCMS analysis indicated ca. 60% conversion and additional aliquots of 137 (52 mg, 0.334) and Pd(PPh$_3$)$_4$ (24 mg, 0.21 mmol) were added and irradiation continued at 115° C. for 30 min. The reaction mixture was concentrated, diluted with EtOAc, washed with brine, dried (Na$_2$SO$_4$), filtered and concentrated in vacuo. The crude product was purified on a preparative SiO$_2$ plate using sequential developments with 2:1 EtOAc/hexane and 3:1 EtOAc/hexane to afford 35 mg (33%) of I-40 as an off-white solid.

Example 25

N-(4-{(E)-2-[5-(2,4-Dioxo-1,2,3,4-tetrahydro-pyrimidin-5-yl)-2-methoxy-3-trifluoromethoxy-phenyl]-vinyl}-phenyl)-methanesulfonamide (I-42)

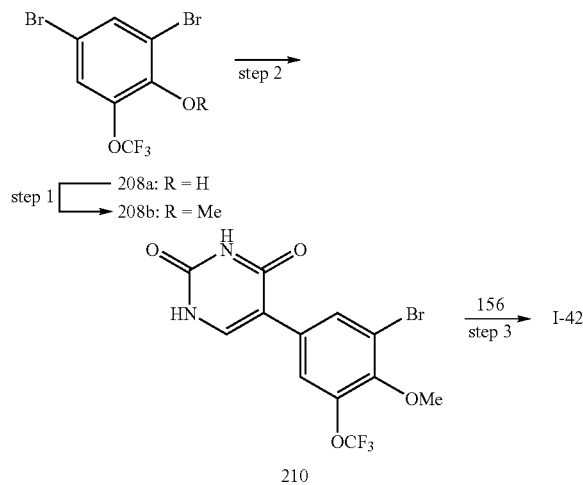

4,6-dibromo-2-trifluoromethoxy-phenol (208a) A solution of 2-trifluoromethoxy-phenol (1.0 g, 5.6 mmol, CASRN 32858-93-8), NBS (2.22 g, 12 mmol) and DMF (30 mL) were stirred overnight under a nitrogen atmosphere. The solution was partitioned between EtOAc and H$_2$O. The organic extract was dried and concentrated in vacuo to afford 208a which contained some DMF but was used with additional purification.

step 1—A solution of 208a (6.6 g, 19.37 mmol), iodomethane (3.35 g, 23.64 mmol), K$_2$CO$_3$ (8.17 g, 39.1 mmol) was warmed to 55° C. for 2 h cooled to RT, sealed and stirred at RT fro 72 h. The reaction mixture was diluted with H$_2$O and extracted with EtOAc. The combined extracts were twice washed with H$_2$O then with brine, dried (MgSO$_4$), filtered and concentrated in vacuo. The crude product was purified by SiO$_2$ chromatography eluting with hexanes to afford 5.03 g of 208b.

step 2-Palladium-catalyzed coupling of 208b (1.1 g, 3.15 mmol) and 137 (0.446 g, 0.286 mmol) was carried out in accord with the procedure described in example 14. The crude product was purified by SiO$_2$ chromatography eluting with 80% EtOAc/hexane to afford 0.577 g of 210 as a white solid.

step 3—Palladium-catalyzed coupling of 210 and 156 was carried out in accord with the procedure described in step 6 of example 16. The crude product was thrice triturated in hot H$_2$O, and the liquid decanted. The remaining white solid was filtered and dried to afford 46 mg of I-42.

Example 26

N-(4-{(E)-2-[3-tert-Butyl-5-(4-hydroxy-2-methyl-6-oxo-1,6-dihydro-pyrimidin-5-yl)-2-methoxy-phenyl]-vinyl}-phenyl)-methanesulfonamide (I-41)

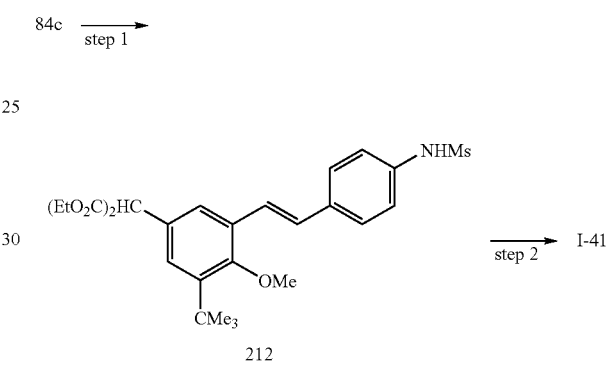

step 1—In a 25 mL round-bottomed flask 84c (400 mg, 912 mmol), 0.17 mL of diethyl malonate (183 mg, 174 µl, 1.14 mmol) and potassium phosphate (581 mg, 2.74 mmol) were combined in toluene (3 mL) under argon. To the mixture was added bis(tri-tert-butylphosphine)palladium(0) (18.7 mg, 36.5 µmol) to produce a yellow solution which was degassed by bubbling argon through the solution for ca.5 min. The reaction mixture was heated to 70° C. in an oil bath and stirred ca. 17 h under an inert atmosphere. The reaction mixture was diluted with EtOAc (25 mL) and poured into 0.4 M HCl (50 mL). The aqueous layer was extracted with EtOAc (1×25 mL). The organic layers were combined and washed with satd. aq. NaCl (1×75 mL). The organic layer was dried (MgSO$_4$), filtered and concentrated in vacuo to afford 600 mg of a bright yellow oil. The crude material was purified by SiO$_2$ chromatography eluting with an EtOAc/hexane gradient (5% to 20% to 40% EtOAc) to afford 212 as a clear oil.

step 2—A 25% solution of sodium methoxide in MeOH (1.5 mL) was added to acetamidine hydrochloride (70 mg, 0.74 mmol) in a 25 mL round-bottomed flask and the resulting mixture was stirred at RT for 10 min. A solution of 212 (110 mg, 0.21 mmol) in MeOH (0.3 mL) was added and the reaction was stirred at 50° C. for 12 h and then at RT for 48 hr. The reaction was concentrated in vacuo. The crude product was purified by SiO$_2$ chromatography elution with a MeOH/DCM gradient (4% to 10% MeOH) to afford I-41 as a white solid (15%): LCMS: (M+H)=484; (M−H)=482; $^1$H NMR (DMSO) δ 7.6 (m, 3H); 7.42 (s, br, 1H); 7.7 (m, 3H); 6.97 (d, br, 1H); 3.74 (s, OMe); 2.99 (s, 3H); 2.28 (s, 3H); 1.36 (s, t-Bu).

Example 27

N-(4-{(E)-2-[3-tert-Butyl-2-methoxy-5-(2-methyl-6-oxo-1,6-dihydro-pyrimidin-5-yl)-phenyl]-vinyl}-phenyl)-methanesulfonamide (I-43)

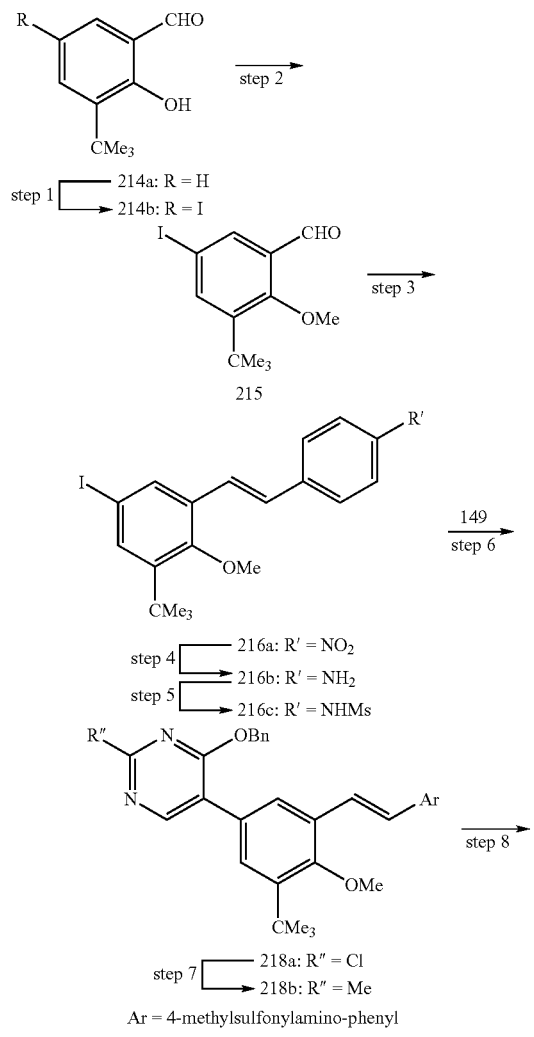

Ar = 4-methylsulfonylamino-phenyl step 1—To a solution of 214a (5 g, 28 mmol) and DMF (40 mL) was added in one portion N-iodosuccinimide (8.2 g, 36 mmol). The solution was stirred at RT for 1 h, diluted with H₂O and twice extracted with EtOAc. The combined organic extracts were washed sequentially with H₂O and brine, dried (Na₂SO₄), filtered and concentrated in vacuo to afford 214b as an oil which was used without further purification.

step 2—The product from step 1 was dissolved in DMF (25 mL) and iodomethane (3 mL) and K₂CO₃ (3 g) were added. The resulting mixture was heated at 60° C. for 2 h. The reaction mixture was cooled, diluted with H₂O and the resulting solid was collected by filtration and dried to afford 6 g of 215.

step 3—The condensation of 215 and diethyl (4-nitrobenzyl)phosphonate was carried out in accord with the procedure described in step 1 of example 1 to afford 1.8 g of 1-tert-butyl-5-iodo-2-methoxy-3-[(E)-2-(4-nitro-phenyl)-vinyl]-benzene (216a).

step 4—To a vigorously suspension of 216a (1.8 g) and DCM (50 mL) was added sequentially zinc dust (6 g) and HOAc (4 mL). The solution was stirred for 10 min then filtered through CELITE and the pad was washed with DCM. The filtrate was stirred over NaHCO₃, washed sequentially with H₂O and brine, dried, filtered and concentrated in vacuo to afford 1.5 g of 216b as a yellow solid.

Conversion of 216b into the sulfonamide was carried out in accord with the procedure described in step 3 of example 1 to afford 216c step 6—A microwave vial was charged with 216c (644 mg, 1.33 mmol), 149 (460 mg, 1.33 mmol), Pd(PPh₃)₄ (150 mg), Na₂CO₃ (425 mg, 4 mmol), dioxane (1.5 ml) and H₂O (1 mL), sealed and irradiated in a microwave synthesizer at 120° C. for 30 min. The reaction was cooled and diluted with EtOAc, washed sequentially with H₂O and brine, dried (Na₂SO₄), filtered and concentrated in vacuo. The crude product was purified by SiO₂ chromatography eluting with an EtOAc/hexane gradient (20 to 40% EtOAc) to afford 0.6 g of 218a.

step 7—A microwave vial was charged with 218a (644 mg, 1.33 mmol), Me₄Sn (200 mg, 1.33 mmol), Pd(PPh₃)₄ (100 mg) and THF (5 ml), sealed and irradiated in a microwave synthesizer at 150° C. for 30 min. The resulting solution was cooled, diluted with EtOAc and vigorously stirred with an aq. KF solution. The organic layer was separated, washed with brine, dried (Na₂SO₄), filtered and evaporated. The crude product was purified by SiO₂ chromatography eluting with an EtOAc/hexane gradient (0 to 20% EtOAc) to afford 80 mg of 218b.

step 8—Demethylation of 218b to afford was carried out in accord with the procedure in step 7 of example 1 to afford 28 mg of I-43.

Example 28

2-{(E)-2-[3-tert-Butyl-2-methoxy-5-(3-oxo-2,3-dihydro-pyridazin-4-yl)-phenyl]-vinyl}-5-methanesulfonylamino-benzoic acid (I-9)

215 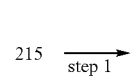

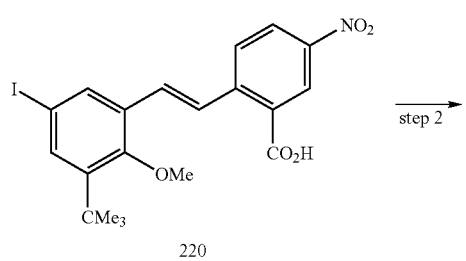

220

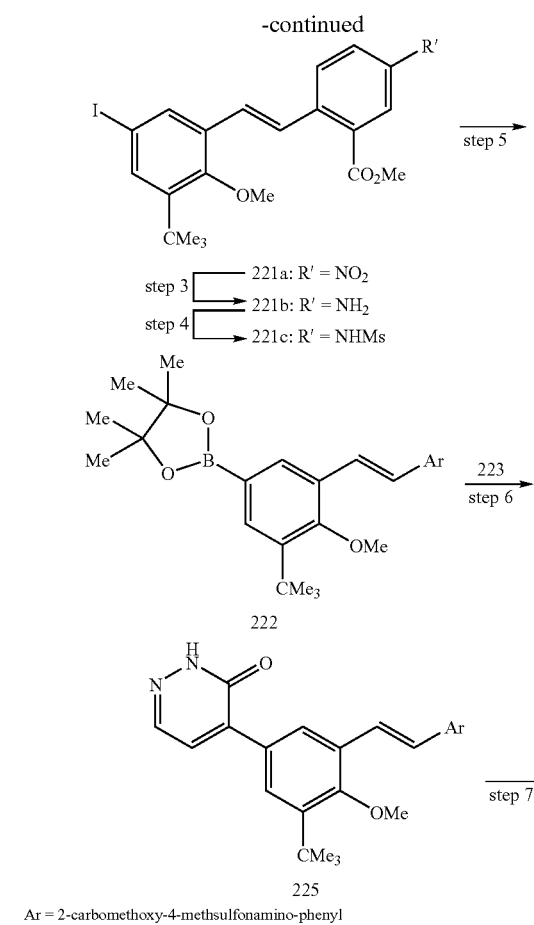

Ar = 2-carbomethoxy-4-methsulfonamino-phenyl step 1—A mixture of 215 (3.58 g, 0.011 mol), methyl 2-methyl-5-nitro-benzoate (2 g, 0.011 mol), DBU (3.8 g, 0.025 mol) and DMSO (30 mL) was heated at 50° C. for 1 h. The reaction mixture was diluted with H$_2$O and 4N NaOH (10 mL) was added. The mixture was twice extracted with EtOAc. The combined extracts were washed sequentially with 6 N HCl, H$_2$O, brine, dried (Na$_2$SO$_4$), filtered and concentrated in vacuo to afford 220 as a yellow solid which was dissolved in DMF and K$_2$CO$_3$ (13.5 g) and iodomethane (1 mL) were added and the resulting solution stirred at RT for 72 h. The solution was diluted with H$_2$O and extracted with EtOAc. The organic extract was washed with brine, dried (Na$_2$SO$_4$), filtered and concentrated in vacuo to afford 3.8 g of 221a.

steps 3 & 4—Reduction of the nitro group (step 3) is carried out in accord with the procedure in step 4 of example 27 to afford the amine 221b. Conversion of 221b into the sulfonamide was carried out in accord with the procedure described in step 3 of example 1 to afford 221c.

step 5—Palladium-catalyzed coupling of 221c and bis-(pinacolato)diboron was carried out in accord with the procedure described in step 1 of example 19 to afford 222. The borane ester was isolated by SiO$_2$ chromatography eluting with an EtOAc/hexane gradient (10 to 40% EtOAc) to afford a 222 contaminated with an additional material but which was sufficiently pure to use in the next step.

step 6 & 7—A microwave vial was charged with 222 (100 mg), 4-chloro-2H-pyridazin-3-one (25 mg), Pd$_2$(dba)$_3$ (5 mg), Xantphos (10 mg, CASRN 161265-03-8), Na$_2$CO$_3$ (50 mg), tert-BuOH and H$_2$O, sealed and irradiated at 150° C. in a microwave synthesizer for 30 min. The reaction was cooled and worked up. The crude product was purified by SiO$_2$ chromatography eluting with an EtOAc/DCM gradient (0 to 30% EtOAc) to afford 10 mg of N-(4-{(E)-2-[3-tert-butyl-2-methoxy-5-(3-oxo-2,3-dihydro-pyridazin-4-yl)-phenyl]-vinyl}-phenyl)-methanesulfonamide. The ester was saponified with LiOH in aqueous MeOH at 60° C. for 1 h, cooled and acidified with 6N HCl. The resulting precipitate was filtered and dried in a vacuum oven to afford 6 mg of I-9.

Example 29

N-(4-{(E)-2-[3-tert-Butyl-2-methoxy-5-(1-methyl-2,4-dioxo-1,2,3,4-tetrahydro-pyrimidin-5-yl)-phenyl]-vinyl}-phenyl)-methanesulfonamide (I-8)

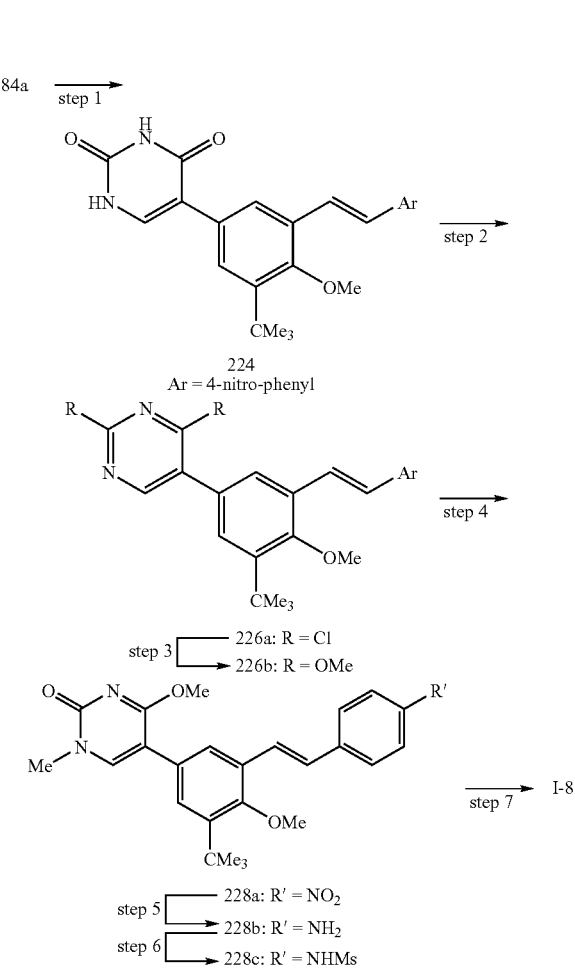

step 1—Palladium catalyzed condensation of 84a and 137 was carried out in accord with the procedure described example 14 to afford 224. The crude product was purified by recrystallization from THF/hexane.

step 2—A suspension of 224 (0.30 g) and POCl$_3$ (6 mL) was heated at 110° C. for 12.5 h. The solution was cooled to RT and poured into ice/H$_2$O and stirred which resulted in the formation of a yellow precipitate. The solid was filtered, dissolved in EtOAc, washed with brine, dried (Na$_2$SO$_4$), filtered and concentrated in vacuo. The crude product was purified by SiO$_2$ chromatography eluting with an EtOAc/hexane gradient (0 to 25% EtOAc over 45 min) to afford 226a.

step 3—A solution of 226a (0.74 g, 1.62 mmol) NaOMe (0.34 g), MeOH (20 mL) and MeCN (5 mL) was stirred at RT for 72 h. The resulting solution was partitioned between EtOAc and H₂O. The organic extracts were washed with brine, dried (Na₂SO₄), filtered and evaporated to afford 0.72 g of 226b which was used without additional purification.

step 4—A solution of 226b (0.112 g, 0.224 mmol), iodomethane (0.22 mL) and DCM (0.3 mL) was stirred at RT for 39 h. The volatile solvents were removed in vacuo and the crude product purified on a preparative SiO₂ TLC plate developed with 5% MeOH/DCM to afford 0.20 g of 228a as a yellow solid.

step 5—Reduction of 228a to 228b was carried out with iron powder in accord with the procedure described in step 5 of example 15.

step 6—Sulfonylation of 228b to afford 228c was carried out in accord with the procedure described in step 5 of example 2.

step 7—Demethylation of 228c to afford I-8 was carried out in accord with the procedure described in step 8 of example 2. The crude product was purified on a preparative TLC plate developed with 5% MeOH/DCM to afford the title compound as a yellow powder.

Example 30

N-(4-{(E)-2-[3-tert-Butyl-5-(2,4-dioxo-1,2,3,4-tetrahydro-pyrimidin-5-yl)-2-methoxy-phenyl]-vinyl}-3-fluoro-phenyl)-methanesulfonamide (I-7)

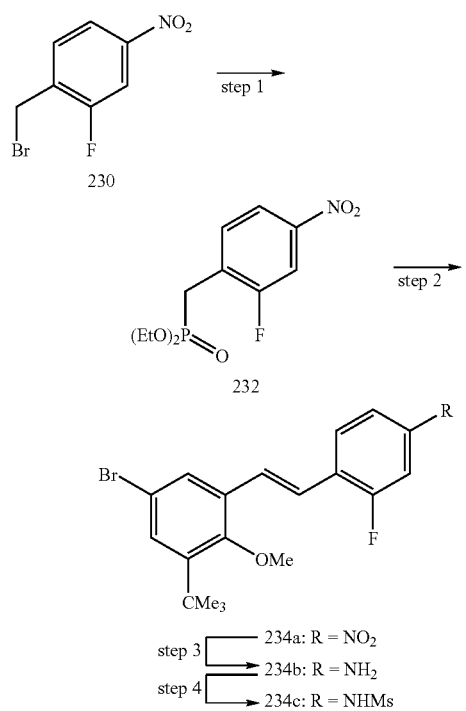

step 1—A mixture of 230 (13.35 g, 57 mmol) and triethyl phosphite (9.8 mL, 57.0 mmol) was heated to 150° C. for 3 h. The mixture was cooled and purified by SiO₂ chromatography to afford 12.4 g of 232 (containing 15% of an impurity).

step 2—Condensation of 232 and 28 was carried out in accord with the procedure in step 1 of example 1 to afford 234a. The product was purified by SiO₂ chromatography eluting with an EtOAc/hexane gradient (0 to 5% EtOAc).

step 3—Reduction of 234a to 234b was carried out with iron powder in accord with the procedure described in step 5 of example 15.

step 4—Sulfonylation of 234b to afford 234c was carried out in accord with the procedure described in step 5 of example 2.

step 5—A microwave vial was charged with 234c (136.8 mg, 0.3 mmol), 137 (56.2 mg, 0.36 mmol), Pd(PPh₃)₄ (34.7 mg, 0.03 mmol), Na₂CO₃ (79.5 mg, 0.75 mmol), MeOH (2 mL), DCM (1 mL) and DMF (1 mL), purged with Argon for 5 min, sealed and irradiated in a microwave synthesizer at 115° C. for 1 h. The reaction mixture was cooled, filtered through CELITE, the filtrate partitioned between EtOAc and brine. The organic layer was washed with brine, water, dried (Na₂SO₄), filtered and concentrated. The crude product was purified by SiO₂ chromatography eluting with an EtOAc/hexane gradient (50 to 100% EtOAc) to afford 77 mg of I-7 as a white solid.

Example 31

N-(4-{(E)-2-[5-(2,4-Dioxo-1,2,3,4-tetrahydro-pyrimidin-5-yl)-2-methoxy-3-(2,2,2-trifluoro-ethyl)-phenyl]-vinyl}-phenyl)-methanesulfonamide (I-38)

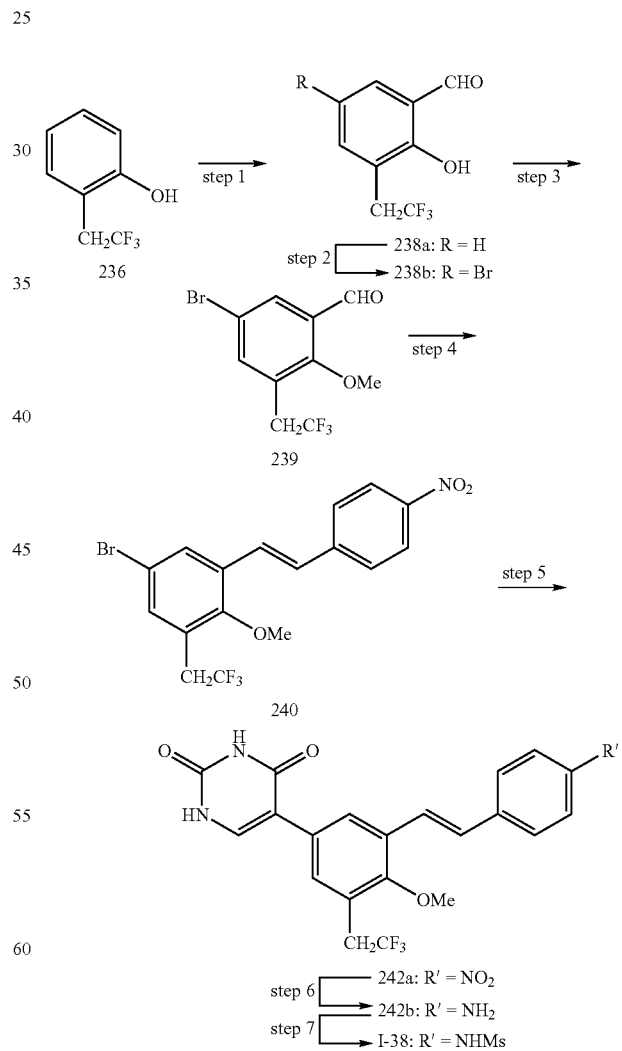

step 1—A mixture of 236 (2.10 g, 11.922 mmol, CASRN 440659-12-1), MgCl₂ (1.70 g, 17.88 mmol), paraformaldehyde (2.5 g, 83.45 mmol), TEA (6.7 mL, 47.69 mmol) and THF was heated at 60° C. overnight. The mixture was cooled and 2N HCl was added. The aqueous solution was extracted with EtOAc. The combined extracts were washed with brine, dried ($Na_2SO_4$), filtered and concentrated in vacuo. The crude product was purified by $SiO_2$ chromatography eluting with an EtOAc/hexane gradient to afford 1.678 g of 238a as oil that solidified on standing.

step 2—To a solution of 238a (1.678 g, 8.219 mmol) and HOAc (8.2 mL) at RT was added dropwise $Br_2$ (0.844 mL, 16.439 mmol). The reaction mixture was stirred at RT for 72 h. The mixture was diluted with DCM and 10% $Na_2S_2O_3$ was added and the mixture stirred for several min. The organic layer was washed with sat'd. aq. $NaHCO_3$, dried ($Na_2SO_4$), filtered and concentrated in vacuo. The crude product was purified by $SiO_2$ chromatography eluting with an EtOAc/hexane gradient (0 to 10% EtOAc) to afford 1.845 g of 238b as a yellow solid.

step 3—O-methylation of 238b was carried out in accord with the procedure described in step 9 of example 18. The crude product was purified by $SiO_2$ chromatography eluting with 10% EtOAc/hexane to afford 239.

step 4—Condensation of 239 with diethyl (4-nitro-benzyl)-phosphonate (step 4) was carried out in accord with the procedures in step 1 of example 1.

step 5—Palladium-catalyzed coupling of 240 (0.16 g, 0.364 mmol) and 137 (0.085 g, 0.546 mmol) was carried out in accord with the procedure described in example 14. The crude product was purified by $SiO_2$ chromatography eluting with 10% MeOH/DCM to afford 242a.

step 6—Reduction of the nitro moiety was carried out with iron in accord with the procedure in step 5 of example 15 and the crude product was purified by column chromatography to afford 242b.

step 7—Sulfonylation of the amine was carried out in accord with the procedure described in step 3 of example 1 to afford I-38. The crude product was purified by HPLC.

Example 32

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570n-Con1 at the end of the reaction was directly proportional to the amount of light emitted by the scintillant.

The HCV polymerase used in the enzymatic activity assay is a 21 amino acid C-terminal deletion of full-length HCV polymerase derived from HCV Con1 strain, genotype 1b (GenBank accession number AJ242654) (NS5B570n-Con1). The NS5B570n-Con1 was sub-cloned downstream to the T7 promoter of the plasmid expression construct pET17b and transformed into *E. coli* strain BL21(DE3) pLysS for protein expression. A single colony was used to start an innoculum for a 10 L culture in LB media supplemented with 100 μg/mL ampicillin at 37° C. Protein expression was induced by the addition of 0.25 mM isopropyl-β-D-thiogalactopyranoside (IPTG) when the optical density of the culture at 600 nM was 0.8. Induction of protein expression was carried out at 30° C. for 16 h after which the cells were harvested by centrifugation. NS5B570n-Con1 was purified to homogeneity using a three-column purification protocol including subsequent column chromatography on Ni-NTA, SP-Sepharose HP and Superdex 75 resins.

Enzymatic reactions in the presence of cIRES RNA template (see section 0004) contained 20 nM cIRES RNA, 20 nM NS5B570n-Con1 enzyme, 0.5 μCi of tritiated UTP (Perkin Elmer catalog no. TRK-412; specific activity: 30 to 60 Ci/mmol;), 1 μM each ATP, CTP, and GTP, 40 mM Tris-HCl pH 8.0, 40 mM NaCl, 4 mM DTT (dithiothreitol), 4 mM MgCl2, 5 μl of compound serial diluted in DMSO, and nuclease-free water to a final reaction volume of 50 μl. Enzymatic reactions in the presence of poly A RNA template (see section 0004) contained 20 nM Poly A:oligo(rU)16 premixed (see section 0004), 20 nM NS5B570n-Con1 enzyme, 1 μCi of tritiated UTP (Perkin Elmer catalog no. TRK-412; specific activity: 30 to 60 Ci/mmol), 40 mM Tris-HCl pH 8.0, 40 mM NaCl, 4 mM DTT (dithiothreitol), 4 mM MgCl2, 5 μl of compound serial diluted in DMSO, and nuclease-free water to a final reaction volume of 50 μl. Reaction mixtures were assembled in 96-well filter plates (cat #MADVN0B, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 μl of scintillant (Microscint 20, Perkin-Elmer) was added to each reaction well.

Two RNA templates were used to assay compounds described herein. The cIRES RNA template was 377 nucleotide long and consisted of a partial complementary sequence (36 nucleotides) of the core protein, followed by 341 nucleotide of the complementary sequence of the internal ribosome entry site. The poly A RNA template (GE Amersham catalog number 27-4110) was a homopolymeric RNA pre-annealed to a oligo(rU)16 primer at a molar ratio of 3-to-1 (primer-template).

The amount of light emitted from the scintillant was converted to counts per minute (CPM) on a Topcount® plate reader (Perkin-Elmer, Energy Range: Low, Efficiency Mode: Normal, Count Time: 1 min, Background Subtract: none, Cross talk reduction: Off).

Data was analyzed in Excel® (Microsoft) and ActivityBase® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50%

$$Y = \% \text{ Min} + \frac{(\% \text{ Max} - \% \text{ Min})}{\left[1 + \frac{X}{(IC_{50})^S}\right]} \quad (i)$$

($IC_{50}$) was calculated by fitting equation (i) to the data where "Y" corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

Example 33

HCV Replicon Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, EMBO 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using the *R. luciferase* Assay system (Promega cat no. E2820). All the reagents described in the following paragraph were included in the manufacturer's kit, and the manufacturer's instructions were followed for preparations of the reagents. The cells were washed once with 100 µL of phosphate buffered saline (pH 7.0) (PBS) per well and lysed with 20 µL of 1×*R. luciferase* Assay lysis buffer prior to incubation at room temperature for 20 min. The plate was then inserted into the Centro LB 960 microplate luminometer (Berthold Technologies), and 100 µL of *R. luciferase* Assay buffer was injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) was used for the cytotoxicity assay. Ten microliter of WST-1 reagent was added to each well of the transparent plates including wells that contain media alone as blanks. Cells were then incubated for 2 h at 37° C., and the OD value was measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

TABLE II

| Compound Number | HCV Replicon Activity $IC_{50}$ (µM) | Cytotoxic Activity $CC_{50}$ (µM) |
| --- | --- | --- |
| I-1 | 0.112 | 24.2 |
| I-4 | 0.347 | — |
| I-9 | 0.071 | — |
| I-13 | 0.001 | — |
| I-21 | 0.113 | — |
| I-22 | 0.025 | 23.2 |
| I-24 | 0.04 | 4.7 |

Example 34

Pharmaceutical compositions of the subject Compounds for administration via several routes were prepared as described in this Example.

Composition for Oral Administration (A)

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I wherein:

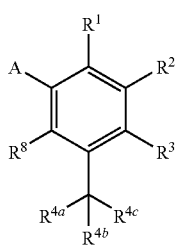

I

A is a heteroaryl radical selected from the group consisting of 6-oxo-1,6-dihydro-pyrimidin-5-yl and 4,6-dioxo-1,4,5,6-tetrahydro-pyrimidin-5-yl said heteroaryl being optionally substituted by halogen, $C_{1-6}$ alkyl, $C_{1-3}$ haloalkyl, $C_{1-3}$ dialkylamino or $C_{1-6}$ alkoxy;

$R^1$ is hydrogen, hydroxy, $C_{1-3}$ hydroxyalkyl, COX or cyano;

$R^2$ is (a) —$[C(R^6)_2]_p$—$Ar^1$, (b) $CR^{7a}$=$CR^{7b}Ar^1$, (c) naphthyl optionally substituted by one to three groups independently selected from the group consisting of $C_{1-6}$ alkoxy, $C_{1-6}$ alkyl, $C_{1-6}$ hydroxyalkyl, halogen, $(CH_2)_nNR^cR^d$, cyano, $C_{1-6}$ alkoxycarbonyl, and carboxyl (d) —$NR^5COAr^1$ or (e) $CONR^5Ar^1$;

$R^3$ is hydrogen, $C_{1-6}$ alkyl, $C_{1-6}$ haloalkyl, $C_{1-6}$ alkoxy, $C_{1-6}$ haloalkoxy, halogen or $R^3$ and $R^{4a}$ together are $CH_2$—O and together with atoms to which they are attached form a 2,3-dihydrobenzofuran;

$R^{4a}$, $R^{4b}$ and $R^{4c}$ (i) when taken independently are selected independently from $C_{1-3}$ alkyl, $C_{1-2}$ alkoxy, $C_{1-2}$ fluoroalkyl, hydroxy or halogen or (ii) when taken together, $R^{4a}$ and $R^{4b}$ together are $C_{2-4}$ alkylene and $R^{4c}$ is $C_{1-3}$ alkyl, $C_{1-2}$ alkoxy, $C_{1-2}$ fluoroalkyl or halogen, or (iii) either $R^8$ or $R^3$ and $R^{4a}$ together are $CH_2$—O and together with atoms to which they are attached for a 2,3-dihydro-benzofuran and $R^{4b}$ and $R^{4c}$ are $C_{1-3}$ alkyl, or (iv) $R^{4a}$ and $R^{4b}$ together are ethylene and $R^{4c}$ is hydrogen, or (v) $R^{4a}$, $R^{4b}$ and $R^{4c}$ together with the carbon to which they are attached are $C_{1-6}$ fluoroalkyl;

$R^8$ is hydrogen, fluorine or $R^8$ and $R^{4a}$ together are $CH_2$—O and together with atoms to which they are attached form a 2,3-dihydrobenzofuran;

$R^5$ is hydrogen or $C_{1-6}$ alkyl;

$R^6$ is independently in each occurrence hydrogen, $C_{1-6}$ alkyl, $C_{1-6}$ alkoxycarbonyl, carboxy or $C_{1-6}$ hydroxyalkyl;

$R^{7a}$ and $R^{7b}$ independently hydrogen or $C_{1-6}$ alkyl;

$Ar^1$ is phenyl or pyridinyl optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_nNR^cR^d$, cyano, $C_{1-6}$ alkoxycarbonyl, carbamoyl, N-alkylcarbamoyl, N,N-dialkylcarbamoyl and carboxyl;

$R^c$ and $R^d$ are independently in hydrogen, $C_{1-6}$ alkyl, $C_{1-6}$ haloalkyl, $C_{1-6}$ acyl, $C_{1-6}$ sulfonyl, sulfamoyl $C_{1-3}$ alkylsulfamoyl, $C_{1-3}$ dialkylsulfamoyl, carbamoyl, $C_{1-3}$ alkylcarbamoyl, or $C_{1-3}$ dialkylcarbamoyl;

X is OH, $C_{1-6}$ alkoxy or $NR^eR^f$;

$R^e$ and $R^f$ are independently hydrogen or $C_{1-6}$ alkyl;

n is zero or 1;

p is zero to three; or, a pharmaceutically acceptable salt thereof.

2. A compound according to claim 1 wherein A is optionally substituted 6-oxo-1,6-dihydro-pyrimidin-5-yl said heteroaryl being optionally substituted by halogen, $C_{1-6}$ alkyl, $C_{1-3}$ haloalkyl, $C_{1-3}$ dialkylamino or $C_{1-6}$ alkoxy.

3. A compound according to claim 2 wherein $R^1$ is hydrogen or hydroxy; $R^2$ is (a) $CR^{7a}$=$CR^{7b}Ar^1$ or (b) —$NR^5COAr^1$; $R^{4a}$, $R^{4b}$ and $R^{4c}$ are independently $C_{1-3}$ alkyl; $R^6$, $R^{7a}$ and $R^{7b}$ are hydrogen; and $Ar^1$ is phenyl or pyridinyl either optionally independently substituted with one to three substitutents selected from the group consisting of hydroxy, $C_{1-6}$ alkoxy, $C_{1-6}$ alkyl, $C_{1-6}$ hydroxyalkyl, halogen, and $(CH_2)_nNR^cR^d$.

4. A compound according to claim 1 wherein A is 4,6-dioxo-2-methyl-1,4,5,6-tetrahydro-pyrimidin-5-yl.

5. A compound according to claim 4 wherein $R^1$ is hydrogen; $R^2$ is $CR^{7a}$=$CR^{7b}Ar^1$; $R^{4a}$, $R^{4b}$ and $R^{4c}$ are independently $C_{1-3}$ alkyl; $R^6$, $R^{7a}$ and $R^{7b}$ are hydrogen; and $Ar^1$ is phenyl or pyridinyl optionally independently substituted with one to three substitutents selected from the group consisting of hydroxy, $C_{1-6}$ alkoxy, $C_{1-6}$ alkyl, $C_{1-6}$ hydroxyalkyl, halogen, and $(CH_2)_n NR^c R^d$.

6. A compound according to claim 1 which compound is selected from the group consisting of:

N-(4-{(E)-2-[3-tert-butyl-2-methoxy-5-(6-oxo-1,6-dihydro-pyrimidin-5-yl)-phenyl]-vinyl}-phenyl)-methane sulfonamide;

2-{(E)-2-[5-(2-benzyloxy-6-oxo-1,6-dihydro-pyrimidin-5-yl)-3-tert-butyl-2-methoxy-phenyl]-vinyl}-5-methanesulfonylamino-benzoic acid methyl ester;

N-(4-{(E)-2-[3-tert-butyl-5-(2-chloro-6-oxo-1,6-dihydro-pyrimidin-5-yl)-2-methoxy-phenyl]-vinyl}-phenyl)-methanesulfonamide;

N-(4-{(E)-2-[3-tert-butyl-2-methoxy-5-(2-methoxy-6-oxo-1,6-dihydro-pyrimidin-5-yl)-phenyl]-vinyl}-phenyl)-methanesulfonamide;

N-(4-{(E)-2-[3-tert-butyl-2-methoxy-5-(2-methoxy-6-oxo-1,6-dihydro-pyrimidin-5-yl)-phenyl]-vinyl}-3-methoxymethyl-phenyl)-methanesulfonamide;

N-(4-{(E)-2-[3-tert-butyl-5-(4-hydroxy-2-methyl-6-oxo-1,6-dihydro-pyrimidin-5-yl)-2-methoxy-phenyl]-vinyl}-phenyl)-methanesulfonamide; and, N-(4-{(E)-2-[3-tert-butyl-2-methoxy-5-(2-methyl-6-oxo-1,6-dihydro-pyrimidin-5-yl)-phenyl]-vinyl}-phenyl)-methanesulfonamide; or a pharmaceutically acceptable salt thereof.

7. A composition comprising a compound according to claim 1 admixed with at least one carrier, diluent or excipient.

* * * * *